(12) United States Patent
Schwarz et al.

(10) Patent No.: US 8,236,963 B2
(45) Date of Patent: Aug. 7, 2012

(54) TRICYCLIC SPIRO DERIVATIVES AS CRTH2 MODULATORS

(75) Inventors: Matthias Schwarz, Gland (VD) (CH); Eric Sebille, Le Poizat (FR); Christophe Cleva, La Tour (FR); Cedric Merlot, Collonges-sous-Saleve (FR); Dennis Church, Commugny (CH); Patrick Page, Saint-Julien-en-Genevois (FR); Jacqueline A. Macritchie, Saffron Walden (GB); John Frederick Atherall, Saffron Walden (GB); Stefano Crosignani, St. Genis-Pouilly (FR); Doris Pupowicz, Veyrier (CH)

(73) Assignee: Merck Serono SA, Vaud (CH)

( * ) Notice: Subject to any disclaimer, the term of this patent is extended or adjusted under 35 U.S.C. 154(b) by 677 days.

(21) Appl. No.: 11/919,471

(22) PCT Filed: May 23, 2006

(86) PCT No.: PCT/EP2006/062545
§ 371 (c)(1),
(2), (4) Date: Jan. 22, 2008

(87) PCT Pub. No.: WO2006/125784
PCT Pub. Date: Nov. 30, 2006

(65) Prior Publication Data
US 2009/0318486 A1 Dec. 24, 2009

Related U.S. Application Data

(60) Provisional application No. 60/688,631, filed on Jun. 8, 2005.

(30) Foreign Application Priority Data

May 24, 2005 (EP) .................... 05104428

(51) Int. Cl.
C07D 277/20 (2006.01)
C07D 271/06 (2006.01)
C07D 417/14 (2006.01)
C07D 487/10 (2006.01)
C07D 261/06 (2006.01)
A61K 31/44 (2006.01)
A61K 31/431 (2006.01)
A61K 31/4184 (2006.01)
A61K 31/4196 (2006.01)
A61K 31/41 (2006.01)

(52) U.S. Cl. ............. 548/147; 548/410; 548/300.7; 548/247; 548/131; 548/129; 548/15; 514/365; 514/278; 514/409; 514/390; 514/397; 514/364; 514/361

(58) Field of Classification Search ............ None
See application file for complete search history.

(56) References Cited

U.S. PATENT DOCUMENTS

| 4,386,100 A | 5/1983 | Brittain et al. |
| 4,478,847 A | 10/1984 | Brittain et al. |
| 5,948,807 A | 9/1999 | Efange et al. |

FOREIGN PATENT DOCUMENTS

| GB | 2 388 540 A | 11/2003 |
| WO | WO 2004/032848 A2 | 4/2004 |
| WO | WO 2004/035543 A1 | 4/2004 |
| WO | WO 2004/096777 A1 | 11/2004 |
| WO | WO 2004/106302 A1 | 12/2004 |
| WO | WO 2004/108692 A1 | 12/2004 |
| WO | WO 2004/108717 A1 | 12/2004 |
| WO | WO 2005/007094 A2 | 1/2005 |
| WO | WO 2005/102338 A1 | 11/2005 |

OTHER PUBLICATIONS

Bueyuekbingoel et al Farmaco (1995), 50(12), pp. 889-891. (Abstract only).*
R. A. Lewis et al.,"Prostaglandin D2 generation after activation of rat and human mast cells with anti-IgE" J. Immunol.(2002) 129, 1627-1631.
Matsuoka et al., "Prostaglandin D2 as a Mediator of Allergic Asthma" Science (2000) 287, 2013-2017.
Woodward et al., "Studies on the ocular pharmacology of prostaglandin D2" Invest Ophthalmol. Vis. Sci. (1990) 31, 138-146.
Woodward et al., "Further studies on ocular responses to DP receptor stimulation", Eur. J. Pharmacol. (1993) 230, 327-333.
Nagata et al., "Selective expression of a novel surface molecule by human Th2 cells in vivo", J. Immunol. (1999) 162, 1278-1286.
Hirai et al."Prostaglandin D2 selectively induces chemotaxis inEur. J. Immunol T helper type 2 cells . . . " J. exp. Med. (2001) 193, 255-261.
Cosmi et al., CRTH2 is the most reliable marker for the detection of circulating human type 2 Th and type 2 T cytotoxic cells . . . , Eur. J. Immunol. (2000) 30, 2972-2979.
Takeshita et al. "CRTH2 is a prominent effector in contact hypersensitivity-induced neutrophil inflammation" International Immunol. (2004) 16, 947-959.

(Continued)

*Primary Examiner* — Kamal Saeed
*Assistant Examiner* — Nyeemah A Grazier
(74) *Attorney, Agent, or Firm* — EMD Serono Research Institute

(57) ABSTRACT

The present invention is related to the use of spiro derivatives of Formula (I) for the treatment and/or prevention of allergic diseases, inflammatory dermatoses and other diseases with an inflammatory component. Specifically, the present invention is related to the use of spiro derivatives for the modulation of CRTH2 activity.

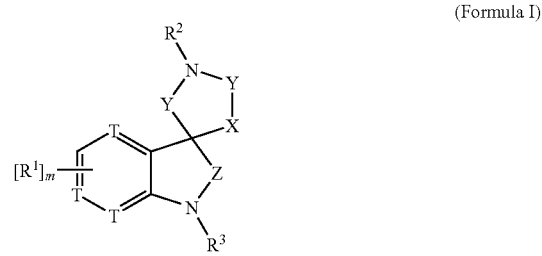

(Formula I)

22 Claims, No Drawings

OTHER PUBLICATIONS

Harrison et al., "The [35S]GTPgammaS binding assay: approaches and applications in pharmacology" Life Science (2003) 74, 489-508.

Sawyer et al., "Molecular pharmacology of the human prostaglandin D2 receptor, CRTH2", Br. J. Pharmacol. 137, (2002) 1163-1172.

Xu et al. "T cell populations primed by hapten sensitization in contact sensitivity are distinguished by polarized patterns . . ." J. Exp. Med. (1996) 183, 1001-1012.

"The Use of Indole-3-Acetic Acids as CRTH2 Receptor Agonists" Expert Opinion on Therapeutic Patents, Ashley Pub., GB, (2004) 14(1), 125-128.

Kumar et al., "A New Route to Spiropyrrolidinyl-oxindole Alkaloids via Iodine Ion . . ." Organic Letters, (2001) 3(26), 4193-4196.

Khalil, et al. "Synthesis of pharmacologically interesting derivatives of . . . ", Bulletin of the Faculty of Pharmacy (cairo University), (1990) 28(1), 39-42.

* cited by examiner

TRICYCLIC SPIRO DERIVATIVES AS CRTH2 MODULATORS

The present application is filed under 35 U.S.C. §371 as a U.S. national phase application of PCT application no. PCT/EP2006/062545, which was filed May 23, 2006. The aforementioned PCT application claimed benefit of priority of EP 05104428.7, which was filed May 24, 2005 and U.S. 60/688,631, which was filed Jun. 8, 2005. The entire text of each of the aforementioned applications is incorporated herein by reference.

FIELD OF THE INVENTION

The present invention relates to Spiro derivatives for use as pharmaceutical active compounds, as well as pharmaceutical formulations containing such Spiro derivatives. Said derivatives are useful for the treatment and/or prevention of allergic diseases and inflammatory dermatoses. Specifically, the present invention is related to the use of Spiro derivatives for the modulation of CRTH2 activity. The present invention furthermore relates to methods of the preparation of spiro derivatives.

BACKGROUND OF THE INVENTION

Prostaglandin D2 (PGD2) has long been associated with inflammatory and atopic conditions, specifically allergic diseases such as asthma, rhinitis and atopic dermatitis (Lewis et al. (1982) J. Immunol. 129, 1627). PGD2 belongs to a class of compounds derived from the 20-carbon fatty acid skeleton of arachidonic acid. In response to an antigen challenge, PGD2 is released in large amounts into the airway as well as to the skin during an acute allergic response. The DP receptor, which is a member of the G-protein coupled receptor (GPCRo) subfamily, has long been thought to be the only receptor of PGD2. DP's role in allergic asthma has been demonstrated with DP deficient mice (Matsuoka et al. (2000) Science 287, 2013-2017). However, despite intense interest in the role of PGD2 in the inflammatory response, a direct link between DP receptor activation and PGD2-stimulated eosinophil migration has not been established (Woodward et al. (1990) Invest. Ophthalomol. Vis. Sci. 31, 138-146; Woodward et al. (1993) Eur. J. Pharmacol. 230, 327-333).

More recently, another G-protein coupled receptor, referred to as "Chemoattractant Receptor-Homologous molecule expressed on T-Helper 2 cells" (CRTH2) (Nagata et al. (1999) J. Immunol. 162, 1278-1286, Hirai et al. (2001) J. Exp. Med. 193, 255-261) has recently been identified as a receptor for PGD2 and this discovery has begun to shed light on the mechanism of action of PGD2. CRTH2, which is also referred to as DP2, GPR44 or DLIR, shows little structural similarity with the DP receptor and other prostanoid receptors. However, CRTH2 possesses similar affinity for PGD2. Among peripheral blood T lymphocytes, human CRTH2 is selectively expressed on Th2 cells and is highly expressed on cell types associated with allergic inflammation such as eosinophils, basophiles and Th2 cells. In addition, CRTH2 mediates PGD2 dependent cell migration of blood eosinophils and basophiles. Furthermore, increased numbers of circulating T cells expressing CRTH2 have been correlated with the severity of atopic dermatitis (Cosmi et al. (2000) Eur. J. Immunol. 30, 2972-2979). The interaction of CRTH2 with PGD2 plays a critical role in the allergen-induced recruitment of Th2 cells in the target tissues of allergic inflammation. Compounds that inhibit the binding of CRTH2 and PGD2 should therefore be useful for the treatment of allergic diseases.

Allergic disease, like asthma, and inflammatory dermatoses represent a major class of complex, and typically chronic, inflammatory diseases that currently affect about 10% of the population and that number appears to be increasing (Bush, R. K., Georgitis J. W., Handbook of asthma and rhinitis. 1st ed. (1997), Abingdon: Blackwell Science. 270). Atopic dermatitis is a chronic skin disease, wherein the skin becomes extremely itchy. It accounts for 10 to 20 percent of all visits to dermatologists. The increasing incidence of allergic diseases and inflammatory dermatoses worldwide underscores the need for new therapies to effectively treat or prevent these diseases. Currently, numerous classes of pharmaceutical agents are widely used to treat these diseases, for example, antihistamines, decongestants, anticholinergics, methylxanthines, cromolyns, corticosteroids, and leukotriene modulators. However, the usefulness of these agents is often limited by side effects and low efficacy.

It has been reported recently that 3-sulphur-substituted indole derivatives (A) exhibit CRTH2 activity (WO 04/106302, AstraZeneca AB) and are potentially useful for the treatment of various respiratory diseases.

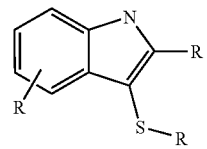

(A)

WO 04/096777 (Bayer Healthcare AG) relates to pyrimidine derivatives, which are useful for the treatment of diseases mediated by CRTH2.

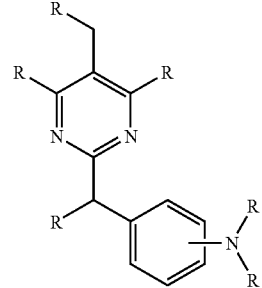

(B)

WO 04/035543 and WO 05/102338 (Warner-Lambert Company LLC) disclose tetrahydrochinoline derivatives as CRTH2 antagonists (C), which are also described to be effective in the treatment of neuropatic pain.

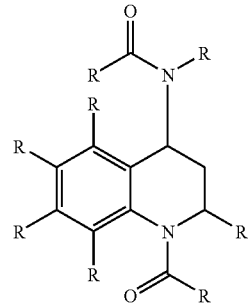

(C)

Specific tetrahydrochinoline derivatives as CRTH2 modulators are also provided by WO 04/032848 (Millennium Pharmaceutical Inc.) and WO 05/007094 (Tularik Inc.). These tetrahydrochinoline derivatives are said to be useful for treating disorders associated with allergic inflammation processes.

SUMMARY OF THE INVENTION

The invention provides in one aspect spiro derivatives according to Formula (I). Another aspect of the present invention consists in the use of spiro derivatives represented by the Formula (I) as pharmaceutical active compounds. Such compounds are suitable for the treatment and/or prevention of allergic disease and inflammatory dermatoses. Said compounds modulate CRTH2. Specifically, the invention relates to spiro derivatives of Formula (I):

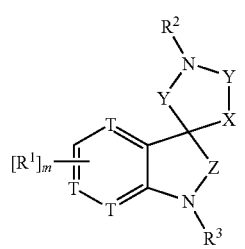

(I)

wherein $R^1$, $R^2$, $R^3$, T, X, Y, Z and m are defined as described in the detailed description below, for use as a medicament.

The invention further provides a pharmaceutical composition comprising a compound of Formula (I), together with a pharmaceutically acceptable excipient or carrier.

The invention further relates to the use of compounds of Formula I for the preparation of a medicament for the treatment and/or prevention of diseases selected from allergic diseases such as allergic asthma, allergic rhinitis, allergic conjunctivitis, and inflammatory dermatoses such as atopic dermatitis, contact hypersensitivity, allergic contact dermatitis, chronic urticaria/chronic idiopathic/autoimmune urticaria, drug-induced exanthems (e.g. toxic epidermal necrolysis or Lyell's syndrome/Stevens-Johnson syndrome/drug hypersensitivity syndrome), photodermatosis or polymorphous light eruption (e.g. photo-irritant contact dermatitis, photoallergic contact dermatitis, chronic actinic dermatitis), and myositis, neurodegenerative disorders such as neuropatic pain, and other diseases with an inflammatory component such as rheumatoid arthritis, multiple sclerosis, osteoarthritis, and inflammatory bowel disease (IBD) and other diseases and disorders associated with CTRH2 activity. Specifically the present invention is related to the use of compounds of Formula (I) for the modulation of CRTH2 activity.

The invention further relates to a method for treating and/or preventing a patient suffering from a disease selected from allergic diseases such as allergic asthma, allergic rhinitis, allergic conjunctivitis, and inflammatory dermatoses such as atopic dermatitis, contact hypersensitivity, allergic contact dermatitis, chronic urticaria/chronic idiopathic/autoimmune urticaria, drug-induced exanthems (e.g. toxic epidermal necrolysis or Lyell's syndrome/Stevens-Johnson syndrome/drug hypersensitivity syndrome), photodermatosis or polymorphous light eruption (e.g. photo-irritant contact dermatitis, photoallergic contact dermatitis, chronic actinic dermatitis), and myositis, neurodegenerative disorders such as neuropatic pain and other diseases with an inflammatory component such as rheumatoid arthritis, multiple sclerosis, osteoarthritis, and inflammatory bowel disease (IBD) and other diseases and disorders associated with CTRH2 activity, by administering a compound according to Formula (I).

The invention further relates to the use of compounds of Formula (I) for the preparation of a pharmaceutical composition.

The invention finally relates to novel compounds of Formula (I) as well as to methods to synthesize compounds of Formula (I).

DESCRIPTION OF THE INVENTION

The following paragraphs provide definitions of various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like. The aryl ring may be also fused to a heterocycloalkyl group. Such fused aryls include dihydrobenzimidazole-2-one, benzo[1,3]dioxole and the like.

"$C_1$-$C_6$-alkyl aryl" refers to $C_1$-$C_6$-alkyl groups having an aryl substituent, such as, for example, benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, 1,3,4-thiadiazolyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyridazinyl, pyrido[3,4-b]pyridyl, pyrido[3,2-b]pyridyl, pyrido[4, 3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl and the like.

"$C_1$-$C_6$-alkyl heteroaryl" refers to $C_1$-$C_6$-alkyl groups having a heteroaryl substituent, such as, for example, 2-furylmethyl, 2-thienylmethyl, 2-(1H-indol-3-yl)ethyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_3$-$C_8$-heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, 1,4-dioxane and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"$C_2$-$C_6$-alkenyl" refers to alkenyl groups preferably having from 2 to 6 carbon atoms and having one or more sites of alkenyl unsaturation. Preferred alkenyl groups include ethenyl (—CH=$CH_2$), n-2-propenyl (allyl, —$CH_2$CH=$CH_2$) and the like.

"$C_2$-$C_6$-alkynyl" refers to alkynyl groups preferably having from 2 to 6 carbon atoms and having one or more sites of alkynyl unsaturation. Preferred alkynyl groups include ethynyl (—C≡CH), propynyl (—$CH_2$C≡CH), and the like.

"Carboxy refers to the group —C(O)OR, where R includes hydrogen or "$C_1$-$C_6$-alkyl".

"Acyl" refers to the group —C(O)R where R includes "$C_1$-$C_6$-alkyl", "aryl", "heteroaryl", "$C_3$-$C_8$-cycloalkyl", "$C_3$-$C_8$-heterocycloalkyl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "hetero-aryl", "$C_1$-$C_6$-alkyl aryl" or "$C_1$-$C_6$-alkyl heteroaryl".

"Aryl acyl" refers to aryl groups having an acyl substituent, including 2-acetylphenyl and the like.

"Heteroaryl acyl" refers to heteroaryl groups having an acyl substituent, including 2-acetylpyridyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred alkoxy groups include by way of example, methoxy, ethoxy, phenoxy and the like.

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl hetero-aryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfinyl" refers to a group "—S(O)—R" wherein R is selected from H, "$C_1$-$C_6$-alkyl", "$C_1$-$C_6$-alkyl" substituted with halogens, e.g., an —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfanyl" refers to groups —S—R where R includes H, "$C_1$-$C_6$-alkyl", "$C_1$-$C_6$-alkyl" optionally substituted with halogens, e.g a —S—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered hetero-cycloalkyl ring.

"Substituted or unsubstituted": Unless otherwise constrained by the definition of the individual substituent, the above set out groups, like "alkyl", "alkenyl", "alkynyl", "alkoxy", "aryl" and "heteroaryl" etc. groups can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quaternary ammonium moieties, "acyl", "acyloxy", "acylamino", "aminocarbonyl", "alkoxycarbonyl", "aryl", "aryloxy", "heteroaryl", "heteroaryloxy", carboxyl, cyano, halogen, hydroxy, nitro, sulfanyl, sulphoxy, sulphonyl, sulfonamide, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides, but also acetals, thioacetals, aminals formed by ring closure for instance in an effort to obtain a protective group.

"Pharmaceutically acceptable cationic salts or complexes" is intended to define such salts as the alkali metal salts, (e.g. sodium and potassium), alkaline earth metal salts (e.g. calcium or magnesium), aluminium salts, ammonium salts and salts with organic amines such as with methylamine, 2-N-morpholinoethanol, dimethylamine, trimethylamine, ethylamine, triethylamine, morpholine, N-Me-D-glucamine, N,N'-bis(phenylmethyl)-1,2-ethanediamine, ethanolamine, diethanolamine, ethylenediamine, N-methylmorpholine, piperidine, benzathine (N,N'-dibenzylethylenediamine), choline, ethylene-diamine, benethamine (N-benzylphenethylamine), diethylamine, piperazine, thromethamine (2-amino-2-hydroxymethyl-1,3-propanediol), procaine as well as amines of formula —NRR'R" wherein R, R', R" is independently hydrogen, alkyl or benzyl.

"Pharmaceutically acceptable salts or complexes" refers to salts or complexes of the below-identified compounds of Formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disul-fonic acid, and poly-galacturonic acid. Said compounds can also be administered as pharmaceutically acceptable quaternary salts known by a person skilled in the art, which specifically include the quarternary ammonium salt of the Formula —NRR'R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that, upon administration to the recipient, is capable of providing directly or indirectly, the activity disclosed herein.

The invention provides in a first aspect spiro derivatives according to Formula (I) that are useful in the treatment and/or prevention of diseases selected from allergic diseases to such as allergic asthma, allergic rhinitis, allergic conjunctivitis, and inflammatory dermatoses such as atopic dermatitis, contact hypersensitivity, allergic contact dermatitis, chronic urticaria/chronic idiopathic/autoimmune urticaria, drug-induced exanthems (e.g. toxic epidermal necrolysis or Lyell's syndrome/Stevens-Johnson syndrome/drug hypersensitivity syndrome), photodermatosis or polymorphous light eruption (e.g. photo-irritant contact dermatitis, photo-allergic contact dermatitis, chronic actinic dermatitis), and myositis neurodegenerative disorders such as neuropatic pain and other diseases with an inflammatory component such as rheumatoid arthritis, multiple sclerosis, osteoarthritis, and inflammatory bowel disease (IBD).

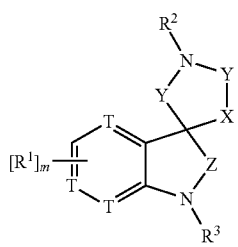

(I)

In one embodiment the compounds according to Formula (I) are suitable as modulators of CRTH2. Therefore, the compounds of the present invention are also particularly useful for the treatment and/or prevention of disorders, which are mediated by CRTH2 activity. Said treatment involves the modulation of CRTH2 in mammals and particular in humans. The modulators of CRTH2 are selected from the group consisting of an inverse agonist, an antagonist, a partial agonist and an agonist of CRTH2.

In one embodiment, the modulators of CRTH2 are inverse agonists of CRTH2.

In another embodiment, the modulators of CRTH2 are antagonists of CRTH2.

In another embodiment, the modulators of CRTH2 are partial agonists of CRTH2.

In another embodiment, the modulators of CRTH2 are agonists of CRTH2.

The compounds according to Formula (I) are suitable for use as a medicament.

Compounds of Formula (I) include also their geometrical isomers, their optically active forms as enantiomers, diastereomers, its racemate forms, as well as pharmaceutically acceptable salts thereof, wherein:

R$^1$ is selected from the group consisting of hydrogen, substituted or unsubstituted C$_1$-C$_6$-alkyl, substituted or unsubstituted C$_1$-C$_6$-alkoxy, substituted or unsubstituted halo-C$_1$-C$_6$-alkyl, substituted or unsubstituted halo-C$_1$-C$_6$-alkoxy, halogen, substituted or unsubstituted aryl and substituted or unsubstituted heteroaryl, and m is an integer selected from 0, 1, 2, 3 or 4.

According to one embodiment, R' is either halogen or halo-C$_1$-C$_6$-alkoxy.

In a preferred embodiment, R' is chloro or fluoro.

In another preferred embodiment, R' is trifluoromethoxy.

R$^2$ is either C$_1$-C$_6$-alkyl or A.

A is selected from the group consisting of A1, A2, A3, A4, A5 and A6:

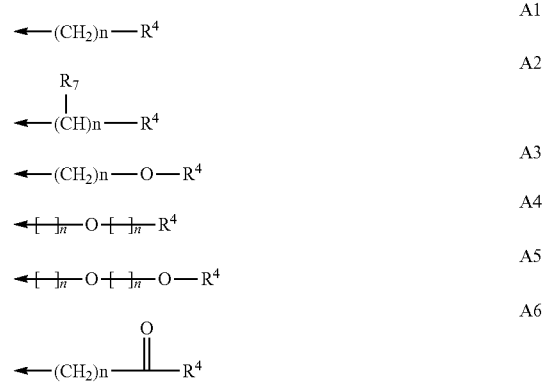

with each n being an integer independently selected from 1, 2, 3 or 4;

wherein, R$^4$ is selected from the group consisting of substituted or unsubstituted C$_1$-C$_6$-alkyl, substituted or unsubstituted C$_2$-C$_6$-alkenyl, substituted or unsubstituted C$_2$-C$_6$-alkynyl, substituted or unsubstituted C$_3$-C$_8$-cycloalkyl, substituted or unsubstituted C$_3$-C$_8$heterocycloalkyl, substituted or unsubstituted aryl, substituted or unsubstituted heteroaryl, substituted or unsubstituted sulfonylamine, substituted or unsubstituted amine, substituted or unsubstituted halo-C$_1$-C$_6$-alkyl, substituted or unsubstituted hydroxylamine and hydroxyl.

Examples of R$^4$ include methyl, ethyl, propyl, isopropyl, ethynyl, propynyl, cyclopropyl, cyclobutyl, cyclopentyl, cyclohexyl, pyrrolidinyl, pyrazolidinyl, piperidinyl, piperazinyl, morpholinyl, dioxinyl, optionally substituted and/or fused dioxinyl derivatives (e.g. 2,3-dihydro-benzo[1,4]dioxine), phenyl, naphthyl, pyridyl, imidazolidinyl, pyrrolyl, pyrimidyl, quinolizinyl, furyl, thienyl, imidazolyl, fused imidazolyl derivatives (e.g. imidazopyridine), oxazolyl, isoxazolyl, thiazolyl, isothiazolyl, carbazolyl, 1,2,3-triazolyl, 1,2,4-triazolyl, 1,2,3-oxadiazolyl, 1,2,4-oxadiazolyl, 1,3,5-oxadiazolyl, 1,3,4-oxadiazolyl, tetrazolyl, 1,3,4-triazinyl, 1,2,3-triazinyl, benzofuryl, isobenzofuryl, benzothienyl, benzotriazolyl, isobenzothienyl, indolyl, isoindolyl, optionally substituted isoindolyl derivatives (e.g. isoindole-1,3-dione), 3H-indolyl, benzimidazolyl, benzothiazolyl, benzoxazolyl, oxolanyl, pyrrolidinyl, optionally substituted pyrrolidinyl derivatives (e.g. pyrrolidine-2,5-dione), pyrazolidinyl, piperidinyl, piperazinyl, pyridyl, imidazolidinyl, 1,2,4-oxadiazolidinyl, 1,2,5-oxadiazolidinyl, 1,3,4-oxadiazolidinyl, isoxazolidinyl, quinazolinyl, pthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, xanthenyl, or benzoquinolyl.

In one embodiment, $R^2$ is A1 with n being an integer selected from 1, 2, 3 or 4.

In a further embodiment, $R^2$ is A1 with n=1.

In another embodiment, $R^2$ is A5 with each n being an integer selected from 1, 2, 3 or 4.

In still a further embodiment, $R^2$ is A5 with each n=2.

In still a further embodiment, $R^4$ is a substituted or unsubstituted aryl.

In still a further embodiment, $R^4$ is a substituted or unsubstituted phenyl or a substituted or unsubstituted naphthyl.

In another embodiment, $R^4$ is a substituted or unsubstituted heteroaryl.

In still a further embodiment, $R^4$ is a thiazolyl, substituted or unsubstituted pyridine or substituted or unsubstituted quinolyl.

Each $R^4$ may optionally be substituted independently with one or more groups $R^6$. $R^3$ is either $C_1$-$C_6$-alkyl or B.

B is:

with n being an integer independently selected from 1, 2, 3 or 4; wherein $R^5$ is carboxy.

According to one embodiment, $R^3$ is B, with n being an integer selected from 1, 2, 3, or 4.

In still a further embodiment, $R^3$ is B with n=1, and wherein $R^5$ is carboxy.

In still a further embodiment, $R^3$ is B with n=3, and wherein $R^5$ is carboxy.

In another embodiment, $R^3$ is $C_1$-$C_6$-alkyl.

In still a further embodiment, $R^3$ is methyl.

In still a further embodiment, $R^3$ is ethyl.

Each $R^6$ is independently selected from the group consisting of $C_1$-$C_6$-alkyl, alkoxy, alkoxycarbonyl, substituted or unsubstituted aryl, substituted or unsubstituted aryl $C_1$-$C_6$-alkyl, substituted or unsubstituted heteroaryl, substituted or unsubstituted heteroaryl $C_1$-$C_6$-alkyl, substituted or unsubstituted $C_3$-$C_8$-cycloalkyl, substituted or unsubstituted $C_3$-$C_8$-heterocycloalkyl, carboxyl, cyano, halogen, hydroxy, amino, aminocarbonyl, acylamino, nitro, sulfoxy, sulfonyl, sulfonylamine, aminosulfonyl and trihalo-$C_1$-$C_6$-alkyl;

In one embodiment $R^6$ is independently selected from the group of $C_1$-$C_6$-alkyl, $C_3$-$C_8$-cycloalkyl, acylamino, aminocarbonyl, aryl, heteroaryl, cyano, halogen, sulfonyl, alkoxy, and trihalomethyl.

$R^7$ is either hydrogen or $C_1$-$C_6$-alkyl;

T is either CH or N;

X is either $CH_2$ or NH;

each Y is independently either C(O) or $CH_2$; and

Z is either C(O) or $CHR^7$;

In one embodiment, T is CH. In another embodiment, X is CH. In another embodiment, at least one Y is C(O). In another embodiment, Z is $CHR^7$.

In a preferred embodiment, T and X are CH, Y is C(O) and Z is $CHR^7$, wherein $R^7$ is hydrogen.

In another preferred embodiment, T and X are CH, at least one Y is C(O) and Z is C(O).

In one embodiment the compounds of the invention have the Formula (I'),

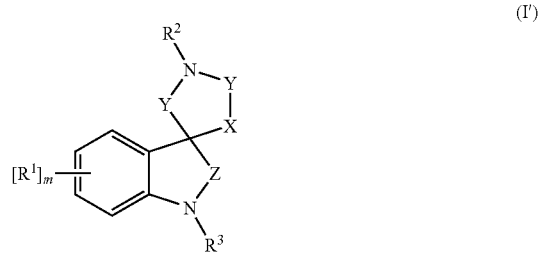

wherein

R' is selected from the group consisting of hydrogen, substituted or unsubstituted $C_1$-$C_6$-alkyl, substituted or unsubstituted $C_1$-$C_6$-alkoxy, substituted or unsubstituted halo-$C_1$-$C_6$-alkyl, substituted or unsubstituted halo-$C_1$-$C_6$-alkoxy, halogen, substituted or unsubstituted aryl and substituted or unsubstituted heteroaryl; and m is an integer selected from 0, 1, 2, 3 or 4.

In a preferred embodiment m is either 1 or 2.

According to one embodiment, R' is either halogen or halo-$C_1$-$C_6$-alkoxy.

In a preferred embodiment, $R^1$ is chloro or fluoro.

In another preferred embodiment, R' is trifluoromethoxy.

$R^2$ is either $C_3$-$C_6$-alkyl or A.

A is selected from the group consisting of A1, A2, A3, A4, A5 and A6:

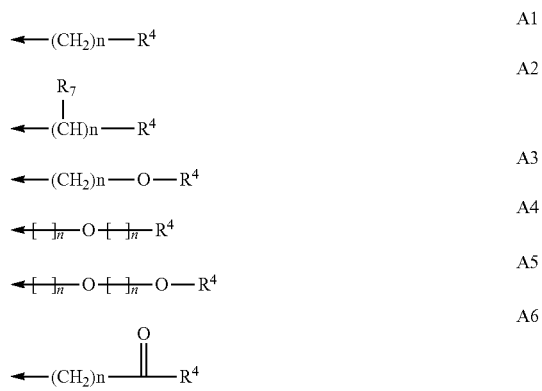

with each n being an integer independently selected from 1, 2, 3, or 4;

wherein $R^4$ is selected from the group consisting of substituted or unsubstituted $C_2$-$C_6$ alkyl, substituted or unsubstituted $C_2$-$C_6$ alkynyl, substituted or unsubstituted $C_3$-$C_8$-cycloalkyl, substituted or unsubstituted $C_3$-$C_8$- heterocycloalkyl, substituted or unsubstituted aryl and substituted or unsubstituted heteroaryl.

Preferred aryls are a substituted phenyl, or substituted or unsubstituted naphthyl. The aryl ring may be also fused to a cycloalkyl or heterocycloalkyl group.

Preferred heteroaryls are monocyclic heteroaryls such as oxazolyl, oxadiazolyl, thiazolyl, thiadiazolyl, furyl, pyridyl, or bicyclic heteroaryl such as benzothiazolyl, naphthyl, quinolyl, indolyl, benzoimidazolyl, imidazolpyridyl or benzotriazolyl.

In one embodiment, $R^2$ is A1 with n being selected from 1, 2, 3, or 4.

In a further embodiment, $R^2$ is A1 with n=1.

In another embodiment, $R^2$ is A5 with each n being an integer selected from 1, 2, 3, or 4.

In still a further embodiment, $R^2$ is A5 with each n=2.

In still a further embodiment, $R^4$ is a substituted phenyl.

In another embodiment, $R^4$ is a substituted or unsubstituted heteroaryl.

In one embodiment A is A1 with n being selected from 1, 2 or 3 and $R^4$ is selected from the group of substituted or unsubstituted $C_2$-$C_6$ alkynyl, substituted or unsubstituted $C_3$-$C_8$-cycloalkyl, substituted or unsubstituted $C_3$-$C_8$-heterocycloalkyl, substituted or unsubstituted aryl and substituted or unsubstituted heteroaryl.

In another embodiment A is selected from A2, A3, A4, A5 and A6, with n being selected from 1, 2 and 3 and $R^4$ is selected from the group consisting of substituted or unsubstituted $C_2$-$C_6$ alkyl, substituted or unsubstituted $C_2$-$C_6$ alkynyl, substituted or unsubstituted $C_3$-$C_8$-cycloalkyl, substituted or unsubstituted $C_3$-$C_8$-heterocycloalkyl, substituted or unsubstituted aryl and substituted or unsubstituted heteroaryl.

Each $R^4$ may optionally be substituted independently with one or more groups $R^6$.

Each $R^6$ is independently selected from the group consisting of $C_1$-$C_6$-alkyl, alkoxy, alkoxycarbonyl, substituted or unsubstituted aryl, substituted or unsubstituted aryl $C_1$-$C_6$-alkyl, substituted or unsubstituted heteroaryl, substituted or unsubstituted heteroaryl $C_1$-$C_6$-alkyl, substituted or unsubstituted $C_3$-$C_8$-cycloalkyl, substituted or unsubstituted $C_3$-$C_8$ leterocycloalkyl, carboxyl, cyano, halogen, hydroxy, amino, aminocarbonyl, acylamino, nitro, sulfoxy, sulfonyl, sulfonylamine, aminosulfonyl and trihalo-$C_1$-$C_6$-alkyl;

In one embodiment $R^6$ is independently selected from the group of $C_1$-$C_6$-alkyl, $C_3$-$C_8$-cycloalkyl, acylamino, aminocarbonyl, aryl, heteroaryl, cyano, halogen, sulfonyl, alkoxy, and trihalomethyl.

$R^7$ is either hydrogen or $C_1$-$C_6$-alkyl;

$R^3$ is B, wherein

B is:

with n being an integer independently selected from 1, 2, 3, 4; wherein $R^5$ is carboxy.

According to one embodiment, $R^3$ is B, with n being an integer selected from 1, 2, 3 or 4.

In still a further embodiment, $R^3$ is B with n=1, and wherein $R^5$ is carboxy.

In still a further embodiment, $R^3$ is B with n=3, and wherein $R^5$ is carboxy.

X is either $CH_2$ or NH;

each Y is independently either C(O) or $CH_2$; and

Z is either C(O) or $CHR^7$;

In another embodiment, X is CH. In another embodiment, at least one Y is C(O). In another embodiment, Z is $CHR^7$.

In a preferred embodiment, X is CH, Y is C(O) and Z is $CHR^7$, wherein $R^7$ is hydrogen.

In another preferred embodiment, X is CH, at least one Y is C(O) and Z is C(O).

Compounds of Formula (I') include also their geometrical isomers, their optically active forms as enantiomers, diastereomers, its racemate forms, as well as pharmaceutically acceptable salts thereof.

A specific sub-group of Formulae (I) and (I') are compounds having Formula (Ia), wherein R', $R^2$, $R^3$ are defined as in Formulae (I) and (I') above.

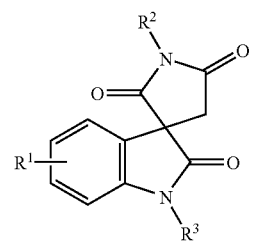

(Ia)

Another sub-group of Formula (Ia) are compounds having Formulae (Ia-1) and (Ia-2), whereby R', $R^2$, $R^3$ are defined as above.

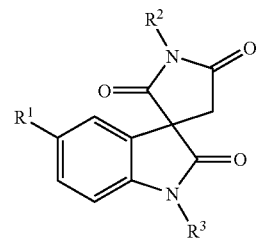

(Ia-1)

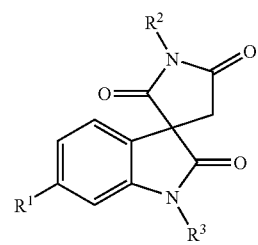

(Ia-2)

Compounds of Formulae (Ia-1) and (Ia-2) exist as enantiomers as shown below.

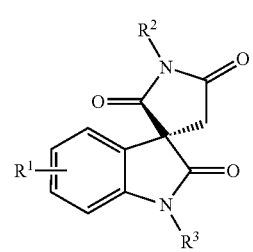

Enantiomer A

Enantiomer B

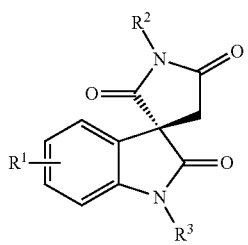
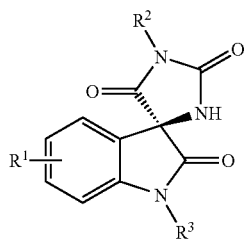

Another specific sub-group of Formulae (I) and (I') are compounds having Formula (Ib), whereby R', R², R³ are defined as for Formulae (I) and (I') above.

Another specific sub-group of Formulae (I) and (I') are compounds having Formula (Ic), whereby R', R², R³ are defined as for Formulae (I) and (I') above.

(Ib)

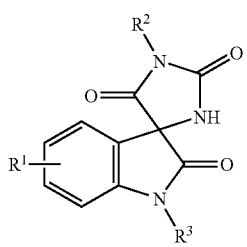

(Ic)

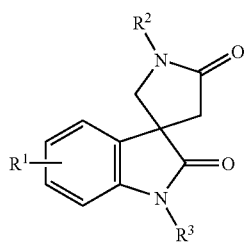

A sub-group of Formula (Ib) are compounds having Formulae (Ib-1) and (Ib-2), whereby R¹, R², R³ are defined as above.

A sub-group of Formula (Ic) are compounds having Formulae (Ic-1) and (Ic-2), whereby R¹, R², R³ are defined as above.

(Ib-1)

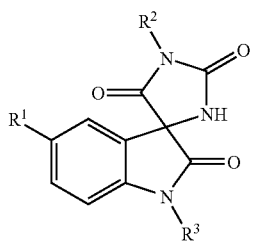

(Ic-1)

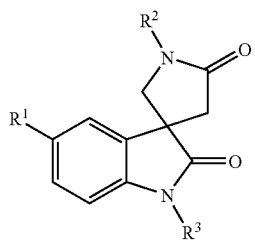

(Ib-2)

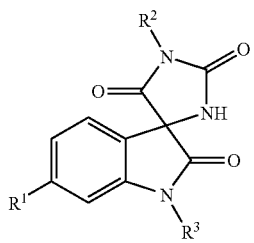

(Ic-2)

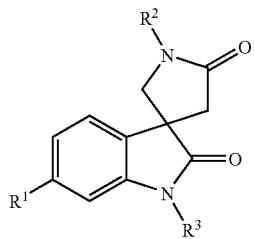

Compounds of Formulae (Ib-1) and (Ib-2) exist as enantiomers as shown below.

Compounds of Formulae (Ic-1) and (Ic-2) exist as enantiomers as shown below.

Enantiomer A

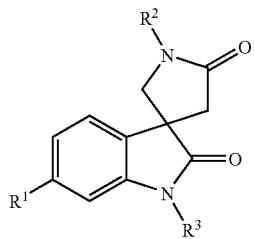
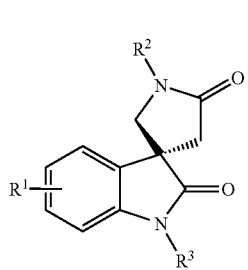

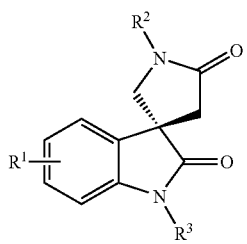
Enantiomer B

Another specific sub-group of Formulae (I) and (I') are compounds having Formula (Id), whereby R', R², R³ are defined as for Formulae (I) and (I') above.

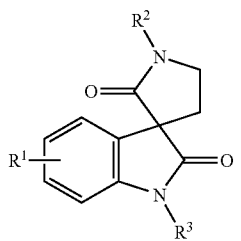
(Id)

A sub-group of Formula (Id) are compounds having Formulae (Id-1) and (Id-2), whereby R', R², R³ are defined as above.

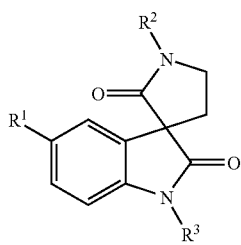
(Id-1)

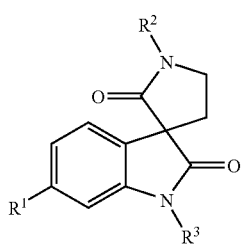
(Id-2)

Compounds of Formulae (Id-1) and (Id-2) exist as enantiomers as shown below.

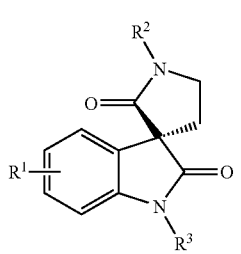
Enantiomer A

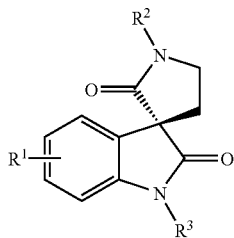
Enantiomer B

Pure enantiomers as well as racemic mixtures of compounds of Formulae (Ia-1) and (Ia-2), (Ib-1) and (Ib-2), (Ic-1) and (Ic-2) and (Id-1) and (Id-2), are within the scope of the invention. Diasteroisomeres of the same are also within the scope of the present invention.

Preferred compounds of Formulae (I') are compounds selected from the list of:
[5-chloro-1'-[(2-methyl-1,3-thiazol-4-yl)methyl]-2,2',5'-trioxospiro[indole-3,3'-pyrrolidin]-1(2H)-yl]acetic acid
[5-chloro-1'-(2,4-dichlorobenzyl)-2,2',5'-trioxospiro[indole-3,3'-pyrrolidin]-1(2H)-yl]acetic acid
[5-chloro-2,2',5'-trioxo-1'-(quinolin-2-ylmethyl)spiro[indole-3,3'-pyrrolidin]-1(2H)-yl]acetic acid
[5-chloro-1'-(4-cyanobenzyl)-2,2',5'-trioxospiro[indole-3,3'-pyrrolidin]-1(2H)-yl]acetic acid
[5-chloro-1'-(3-chlorobenzyl)-2,2',5'-trioxospiro[indole-3,3'-pyrrolidin]-1(2H)-yl]acetic acid
[5-chloro-1'-(3,4-dichlorobenzyl)-2,2',5'-trioxospiro[indole-3,3'-pyrrolidin]-1(2H)-yl]acetic acid
[5-chloro-1'-(2-fluorobenzyl)-2,2',5'-trioxospiro[indole-3,3'-pyrrolidin]-1(2H)-yl]acetic acid
[5-chloro-1'-(4-fluorobenzyl)-2,2',5'-trioxospiro[indole-3,3'-pyrrolidin]-1(2H)-yl]acetic acid
[5-chloro-1'-(1-naphthylmethyl)-2,2',5'-trioxospiro[indole-3,3'-pyrrolidin]-1(2H)-yl]acetic acid
[5-chloro-2,2',5'-trioxo-1'-(3-phenoxybenzyl)spiro[indole-3,3'-pyrrolidin]-1(2H)-yl]acetic acid
[5-chloro-1'-(3-fluorobenzyl)-2,2',5'-trioxospiro[indole-3,3'-pyrrolidin]-1(2H)-yl]acetic acid
(1'-benzyl-5-chloro-2,2',5'-trioxospiro[indole-3,3'-pyrrolidin]-1(2H)-yl)acetic acid
[5-chloro-1'-(4-chlorobenzyl)-2,2',5'-trioxospiro[indole-3,3'-pyrrolidin]-1(2H)-yl]acetic acid
[5-chloro-1'-(4-methoxybenzyl)-2,2',5'-trioxospiro[indole-3,3'-pyrrolidin]-1(2H)-yl]acetic acid
[5-chloro-1'-(3-methoxybenzyl)-2,2',5'-trioxospiro[indole-3,3'-pyrrolidin]-1(2H)-yl]acetic acid
[5-chloro-1'-(2,3-dihydro-1,4-benzodioxin-2-ylmethyl)-2,2',5'-trioxospiro[indole-3,3'-pyrrolidin]-1(2H)-yl]acetic acid
[5-chloro-2,2',5'-trioxo-1'-(pyridin-2-ylmethyl)spiro[indole-3,3'-pyrrolidin]-1(2H)-yl]acetic acid
[5-chloro-2,2',5'-trioxo-1'-{[5-(trifluoromethyl)-2-furyl]methyl}spiro[indole-3,3'-pyrrolidin]-1(2H)-yl]acetic acid
[5-chloro-1'-(4-methylbenzyl)-2,2',5'-trioxospiro[indole-3,3'-pyrrolidin]-1(2H)-yl]acetic acid
[5-chloro-2,2',5'-trioxo-1'-[3-(trifluoromethyl)benzyl]spiro[indole-3,3'-pyrrolidin]-1(2H)-yl]acetic acid
[5-chloro-1'-(2-naphthylmethyl)-2,2',5'-trioxospiro[indole-3,3'-pyrrolidin]-1(2H)-yl]acetic acid
[5-chloro-2,2',5'-trioxo-1'-(1-phenylethyl)spiro[indole-3,3'-pyrrolidin]-1(2H)-yl]acetic acid
[5-chloro-2,2',5'-trioxo-1'-(2-phenylethyl)spiro[indole-3,3'-pyrrolidin]-1(2H)-yl]acetic acid

[5-chloro-1'-(imidazo[1,2-a]pyridin-2-ylmethyl)-2,2',5'-trioxospiro[indole-3,3'-pyrrolidin]-1(2H)-yl]acetic acid

[5-chloro-2,2',5'-trioxo-1'-[(2E)-3-phenylprop-2-en-1-yl]spiro[indole-3,3'-pyrrolidin]-1(2H)-yl]acetic acid

[5-chloro-2,2',5'-trioxo-1'-[4-(trifluoromethyl)benzyl]spiro[indole-3,3'-pyrrolidin]-1(2H)-yl]acetic acid 4-(1'-benzyl-6-chloro-2,2',5'-trioxospiro[indole-3,3'-pyrrolidin]-1(2H)-yl)butanoic acid

[5-chloro-1'-(2-ethoxyethyl)-2,2',5'-trioxospiro[indole-3,3'-pyrrolidin]-1(2H)-yl]acetic acid

[1'-[2-(benzyloxy)ethyl]-5-chloro-2,2',5'-trioxospiro[indole-3,3'-pyrrolidin]-1(2H)-yl]acetic acid

[5-chloro-2,2',5'-trioxo-1'-(2-phenoxyethyl)spiro[indole-3,3'-pyrrolidin]-1(2H)-yl]acetic acid

[5-chloro-2,2',5'-trioxo-1'-(3-phenylprop-2-yn-1-yl)spiro[indole-3,3'-pyrrolidin]-1(2H)-yl]acetic acid

[5-chloro-1'-[(1-methyl-1H-imidazol-2-yl)methyl]-2,2',5'-trioxospiro[indole-3,3'-pyrrolidin]-1(2H)-yl]acetic acid 4-[5-chloro-1'-(4-fluorobenzyl)-2,2',5'-trioxospiro[indole-3,3'-pyrrolidin]-1(2H)-yl]butanoic acid 4-[5-chloro-1'-(4-chlorobenzyl)-2,2',5'-trioxospiro[indole-3,3'-pyrrolidin]-1(2H)-yl]butanoic acid 4-[5-chloro-2,2',5'-trioxo-1'-[4-(trifluoromethyl)benzyl]spiro[indole-3,3'-pyrrolidin]-1(2H)-yl]butanoic acid

[1'-benzyl-2,2',5'-trioxo-5-(trifluoromethoxy)spiro[indole-3,3'-pyrrolidin]-1(2H)-yl]acetic acid

[1'-(4-methoxybenzyl)-2,2',5'-trioxo-5-(trifluoromethoxy)spiro[indole-3,3'-pyrrolidin]-1(2H)-yl]acetic acid

[1'-(3-fluorobenzyl)-2,2',5'-trioxo-5-(trifluoromethoxy)spiro[indole-3,3'-pyrrolidin]-1(2H)-yl]acetic acid

[1'-(2-fluorobenzyl)-2,2',5'-trioxo-5-(trifluoromethoxy)spiro[indole-3,3'-pyrrolidin]-1(2H)-yl]acetic acid

[2,2',5'-trioxo-5-(trifluoromethoxy)-1'-[3-(trifluoromethyl)benzyl]spiro[indole-3,3'-pyrrolidin]-1(2H)-yl]acetic acid

[1'-(1-naphthylmethyl)-2,2',5'-trioxo-5-(trifluoromethoxy)spiro[indole-3,3'-pyrrolidin]-1(2H)-yl]acetic acid

[1'-(4-chlorobenzyl)-2,2',5'-trioxo-5-(trifluoromethoxy)spiro[indole-3,3'-pyrrolidin]-1(2H)-yl]acetic acid

[1'-(4-fluorobenzyl)-2,2',5'-trioxo-5-(trifluoromethoxy)spiro[indole-3,3'-pyrrolidin]-1(2H)-yl]acetic acid 4-[5-chloro-1'-(4-methoxybenzyl)-2,2',5'-trioxospiro[indole-3,3'-pyrrolidin]-1(2H)-yl]butanoic acid 4-[5-chloro-1'-(2-fluorobenzyl)-2,2',5'-trioxospiro[indole-3,3'-pyrrolidin]-1(2H)-yl]butanoic acid

[(3S)-1'-benzyl-5-chloro-2,2',5'-trioxospiro[indole-3,3'-pyrrolidin]-1(2H)-yl]acetic acid

[(3R)-1'-benzyl-5-chloro-2,2',5'-trioxospiro[indole-3,3'-pyrrolidin]-1(2H)-yl]acetic acid

[6-chloro-1'-(2-fluorobenzyl)-2,2',5'-trioxospiro[indole-3,3'-pyrrolidin]-1(2H)-yl]acetic acid

[6-chloro-1'-(3-fluorobenzyl)-2,2',5'-trioxospiro[indole-3,3'-pyrrolidin]-1(2H)-yl]acetic acid

[6-chloro-1'-(4-fluorobenzyl)-2,2',5'-trioxospiro[indole-3,3'-pyrrolidin]-1(2H)-yl]acetic acid 4-[5-chloro-2,2',5'-trioxo-1'-(2-phenylethyl)spiro[indole-3,3'-pyrrolidin]-1(2H)-yl]butanoic acid

[5-chloro-1'-(3,5-dichlorobenzyl)-2,2',5'-trioxospiro[indole-3,3'-pyrrolidin]-1(2H)-yl]acetic acid

[5-chloro-2,2',5'-trioxo-1'-(4-phenoxybenzyl)spiro[indole-3,3'-pyrrolidin]-1(2H)-yl]acetic acid

[5-chloro-1'-(2-methoxybenzyl)-2,2',5'-trioxospiro[indole-3,3'-pyrrolidin]-1(2H)-yl]acetic acid

[5-chloro-1'-[4-(methylsulfonyl)benzyl]-2,2',5'-trioxospiro[indole-3,3'-pyrrolidin]-1(2H)-yl]acetic acid

[1'-[4-(aminocarbonyl)benzyl]-5-chloro-2,2',5'-trioxospiro[indole-3,3'-pyrrolidin]-1(2H)-yl]acetic acid

[5-chloro-1'-(3-cyanobenzyl)-2,2',5'-trioxospiro[indole-3,3'-pyrrolidin]-1(2H)-yl]acetic acid

[5-chloro-1'-[(5-methylisoxazol-3-yl)methyl]-2,2',5'-trioxospiro[indole-3,3'-pyrrolidin]-1(2H)-yl]acetic acid

[1'-(1,3-benzothiazol-2-ylmethyl)-5-chloro-2,2',5'-trioxospiro[indole-3,3'-pyrrolidin]-1(2H)-yl]acetic acid

[5-chloro-1'-[(5-chloro-2-thienyl)methyl]-2,2',5'-trioxospiro[indole-3,3'-pyrrolidin]-1(2H)-yl]acetic acid

[5-chloro-1'-[(5-chloro-1,2,4-thiadiazol-3-yl)methyl]-2,2',5'-trioxospiro[indole-3,3'-pyrrolidin]-1(2H)-yl]acetic acid

[5-chloro-2,2',5'-trioxo-1'-[(2-phenyl-1,3-thiazol-4-yl)methyl]spiro[indole-3,3'-pyrrolidin]-1(2H)-yl]acetic acid

[5-chloro-1'-(2-chloro-4-fluorobenzyl)-2,2',5'-trioxospiro[indole-3,3'-pyrrolidin]-1(2H)-yl]acetic acid

[5-chloro-1'-(2,5-dichlorobenzyl)-2,2',5'-trioxospiro[indole-3,3'-pyrrolidin]-1(2H)-yl]acetic acid

[1'-[4-(acetylamino)benzyl]-5-chloro-2,2',5'-trioxospiro[indole-3,3'-pyrrolidin]-1(2H)-yl]acetic acid

[5-chloro-1'-[(6-chloropyridin-3-yl)methyl]-2,2',5'-trioxospiro[indole-3,3'-pyrrolidin]-1(2H)-yl]acetic acid

[5-chloro-1'-(1H-indol-3-ylmethyl)-2,2',5'-trioxospiro[indole-3,3'-pyrrolidin]-1(2H)-yl]acetic acid

[5-chloro-1'-(5-chloro-2-fluorobenzyl)-2,2',5'-trioxospiro[indole-3,3'-pyrrolidin]-1(2H)-yl]acetic acid

[5-chloro-2,2',5'-trioxo-1'-(1,3-thiazol-4-ylmethyl)spiro[indole-3,3'-pyrrolidin]-1(2H)-yl]acetic acid

[5-chloro-1'-[(4-chloropyridin-3-yl)methyl]-2,2',5'-trioxospiro[indole-3,3'-pyrrolidin]-1(2H)-yl]acetic acid

[5-chloro-2,2',5'-trioxo-1'-(pyridin-3-ylmethyl)spiro[indole-3,3'-pyrrolidin]-1(2H)-yl]acetic acid

[5-chloro-1'-[(3,5-dimethylisoxazol-4-yl)methyl]-2,2',5'-trioxospiro[indole-3,3'-pyrrolidin]-1(2H)-yl]acetic acid

[1'-[(5-tert-butyl-1,2,4-oxadiazol-3-yl)methyl]-5-chloro-2,2',5'-trioxospiro[indole-3,3'-pyrrolidin]-1(2H)-yl]acetic acid

[5-chloro-1'-[(5-cyclopropyl-1,3,4-thiadiazol-2-yl)methyl]-2,2',5'-trioxospiro[indole-3,3'-pyrrolidin]-1(2H)-yl]acetic acid

[5-chloro-1'-[(4-methoxy-3,5-dimethylpyridin-2-yl)methyl]-2,2',5'-trioxospiro[indole-3,3'-pyrrolidin]-1(2H)-yl]acetic acid

[5-chloro-1'-[(4,6-dichloropyridin-3-yl)methyl]-2,2',5'-trioxospiro[indole-3,3'-pyrrolidin]-1(2H)-yl]acetic acid

[5-chloro-2,2',5'-trioxo-1'-(2-thienylmethyl)spiro[indole-3,3'-pyrrolidin]-1(2H)-yl]acetic acid

[5-chloro-1'-[(3,4-dimethoxypyridin-2-yl)methyl]-2,2',5'-trioxospiro[indole-3,3'-pyrrolidin]-1(2H)-yl]acetic acid

[5-chloro-1'-(isoquinolin-1-ylmethyl)-2,2',5'-trioxospiro[indole-3,3'-pyrrolidin]-1(2H)-yl]acetic acid

[5-chloro-2,2',5'-trioxo-1'-[(5-phenyl-1,2,4-oxadiazol-3-yl)methyl]Spiro[indole-3,3'-pyrrolidin]-1(2H)-yl]acetic acid 1'-benzyl-5-chloro-1-(1H-tetrazol-5-ylmethyl)-2'H,5'H-spiro[indole-3,3'-pyrrolidine]-2,2',5'(1H)-trione (3R)-[5-chloro-1'-(3-chlorobenzyl)-2,2',5'-trioxospiro[indole-3,3'-pyrrolidin]-1(2H)-yl]acetic acid (3S)-[5-chloro-1'-(3-chlorobenzyl)-2,2',5'-trioxospiro[indole-3,3'-pyrrolidin]-1(2H)-yl]acetic acid (3R)-[5-chloro-1'-(3-methoxybenzyl)-2,2',5'-trioxospiro[indole-3,3'-pyrrolidin]-1(2H)-yl]acetic acid (3S)-[5-chloro-1'-(3-methoxybenzyl)-2,2',5'-trioxospiro[indole-3,3'-pyrrolidin]-1(2H)-yl]acetic acid

[5-chloro-1'-(2,4-difluorobenzyl)-2,2',5'-trioxospiro[indole-3,3'-pyrrolidin]-1(2H)-yl]acetic acid

[5-chloro-1'-(1,3-oxazol-2-ylmethyl)-2,2',5'-trioxospiro[indole-3,3'-pyrrolidin]-1(2H)-yl]acetic acid

[5-chloro-1'-[(4-methoxy-3-methylpyridin-2-yl)methyl]-2, 2',5'-trioxospiro[indole-3,3'-pyrrolidin]-1(2H)-yl]acetic acid
[5-chloro-1'-{[2-(4-chlorophenyl)-1,3-thiazol-4-yl]methyl}-2,2',5'-trioxospiro[indole-3,3'-pyrrolidin]-1(2H)-yl]acetic acid
[5-chloro-1'-{[5-(4-methoxyphenyl)-1,2,4-oxadiazol-3-yl]methyl}-2,2',5'-trioxospiro[indole-3,3'-pyrrolidin]-1(2H)-yl]acetic acid
[5-chloro-1'-[(1-methyl-1H-1,2,3-benzotriazol-5-yl)methyl]-2,2',5'-trioxospiro[indole-3,3'-pyrrolidin]-1(2H)-yl]acetic acid
[5-chloro-1'-(3-furylmethyl)-2,2',5'-trioxospiro[indole-3,3'-pyrrolidin]-1(2H)-yl]acetic acid
[5-chloro-1'-(2-chloro-5-fluorobenzyl)-2,2',5'-trioxospiro[indole-3,3'-pyrrolidin]-1(2H)-yl]acetic acid
[5-chloro-1'-(2,5-difluorobenzyl)-2,2',5'-trioxospiro[indole-3,3'-pyrrolidin]-1(2H)-yl]acetic acid
[5-chloro-1'-(2,3-difluorobenzyl)-2,2',5'-trioxospiro[indole-3,3'-pyrrolidin]-1(2H)-yl]acetic acid
[5-chloro-1'-(3,5-difluorobenzyl)-2,2',5'-trioxospiro[indole-3,3'-pyrrolidin]-1(2H)-yl]acetic acid
[5-chloro-1'-(3,4-difluorobenzyl)-2,2',5'-trioxospiro[indole-3,3'-pyrrolidin]-1(2H)-yl]acetic acid
[5-chloro-1'-[(1-methyl-1H-benzimidazol-2-ylmethyl]-2,2',5'-trioxospiro[indole-3,3'-pyrrolidin]-1(2H)-yl]acetic acid
[5-chloro-1'-(3-fluoro-4-methoxybenzyl)-2,2',5'-trioxospiro[indole-3,3'-pyrrolidin]-1(2H)-yl]acetic acid
[5-chloro-1'-(3-chloro-5-fluorobenzyl)-2,2',5'-trioxospiro[indole-3,3'-pyrrolidin]-1(2H)-yl]acetic acid
[5-chloro-1'-[(5-methyl-3-phenylisoxazol-4-yl)methyl]-2,2',5'-trioxospiro[indole-3,3'-pyrrolidin]-1(2H)-yl]acetic acid
[5-chloro-1'-[(3-methyl-5-phenylisoxazol-4-yl)methyl]-2,2',5'-trioxospiro[indole-3,3'-pyrrolidin]-1(2H)-yl]acetic acid
[5-chloro-1'-{[2-(3-chlorophenyl)-1,3-thiazol-4-yl]methyl}-2,2',5'-trioxospiro[indole-3,3'-pyrrolidin]-1(2H)-yl]acetic acid
[5-chloro-1'-(2-fluorobenzyl)-2,2',5'-trioxospiro[indole-3,3'-pyrrolidin]-1(2H)-yl]acetic acid
[5'-chloro-1-(5-chloro-2-fluorobenzyl)-2,2',5-trioxospiro[imidazolidine-4,3'-indol]-1'(2'H)-yl]acetic acid
[5'-chloro-1-[(5-methyl-3-phenylisoxazol-4-yl)methyl]-2,2',5-trioxospiro[imidazolidine-4,3'-indol]-1'(2'H)-yl]acetic acid
(1-benzyl-5'-chloro-2,2',5-trioxospiro[imidazolidine-4,3'-indol]-1'(2'H)-yl)acetic acid
[5'-chloro-1-(2-fluorobenzyl)-2,2',5-trioxospiro[imidazolidine-4,3'-indol]-1'(2'H)-yl]acetic acid
(3R)-[5-chloro-1'-(2-fluorobenzyl)-2,2',5'-trioxospiro[indole-3,3'-pyrrolidin]-1(2H)-yl]acetic acid
(3S)-[5-chloro-1'-(2-fluorobenzyl)-2,2',5'-trioxospiro[indole-3,3'-pyrrolidin]-1(2H)-yl]acetic acid
(3S)-[5-chloro-1'-(2-fluoro-5-chlorobenzyl)-2,2',5'-trioxospiro[indole-3,3'-pyrrolidin]-1(2H)-yl]acetic acid
(3R)-[5-chloro-1'-(2-fluoro-5-chlorobenzyl)-2,2',5'-trioxospiro[indole-3,3'-pyrrolidin]-1(2H)-yl]acetic acid
(1'-benzyl-5-chloro-2,5'-dioxospiro[indole-3,3'-pyrrolidin]-1(2H)-yl)acetic acid
[5-chloro-1'-[(3-methyl-5-phenylisoxazol-4-yl)methyl]-2,5'-dioxospiro[indole-3,3'-pyrrolidin]-1(2H)-yl]acetic acid
[5-chloro-1'-(2-fluorobenzyl)-2,5'-dioxospiro[indole-3,3'-pyrrolidin]-1(2H)-yl]acetic acid
[5-chloro-1'-(5-chloro-2-fluorobenzyl)-2,5'-dioxospiro[indole-3,3'-pyrrolidin]-1(2H)-yl]acetic acid
[5-chloro-1'-[(5-methyl-3-phenylisoxazol-4-yl)methyl]-2,2'-dioxospiro[indole-3,3'-pyrrolidin]-1(2H)-yl]acetic acid Preferred pharmaceutically acceptable cationic salts or complexes of compounds of Formulae (I) and (I'), and compounds of sub-groups of Formulae (Ia, Ib, Ic, Id) containing for example a carboxylic residue are salts formed with pharmaceutically alkali metal salts, alkaline earth metal salts, aluminium salts, ammonium salts and salts with organic amines.

In a second aspect, the invention provides spiro derivatives of Formulae (I) or (I') for use as a medicament. In a preferred embodiment these spriro derivatives are compounds of sub-Formulae (Ia), (Ib), (Ic), (Id). In another preferred embodiment the compounds have Formulae (Ia-1), (Ia-2), (Ib-1), (Ib-2), (Ic-1), (Ic-2), (Id-1) or (Id-2).

In another embodiment the Spiro derivative for use as a medicament is selected from the compounds selected from the list given above and the following compounds: (1'-benzyl-5-fluoro-2,2',5'-trioxospiro[indole-3,3'-pyrrolidin]-1(2H)-yl)acetic acid
4-(1'-allyl-5-chloro-2,2',5'-trioxospiro[indole-3,3'-pyrrolidin]-1(2H)-yl)butanoic acid
[5-chloro-1'-(2-methoxyethyl)-2,2',5'-trioxospiro[indole-3,3'-pyrrolidin]-1(2H)-yl]acetic acid
4-(1'-benzyl-5-chloro-2,2',5'-trioxospiro[indole-3,3'-pyrrolidin]-1(2H)-yl)butanoic acid
(1'-benzyl-5-methoxy-2,2',5'-trioxospiro[indole-3,3'-pyrrolidin]-1(2H)-yl)acetic acid
[5-fluoro-1'-[(2-methoxyethoxy)methyl]-2,2',5'-trioxospiro[indole-3,3'-pyrrolidin]-1(2H)-yl]acetic acid
4-(1'-allyl-5-fluoro-2,2',5'-trioxospiro[indole-3,3'-pyrrolidin]-1(2H)-yl)butanoic acid
4-(1'-benzyl-5-fluoro-2,2',5'-trioxospiro[indole-3,3'-pyrrolidin]-1(2H)-yl)butanoic acid, and
[5-chloro-1'-[2-(dimethylamino)-2-oxoethyl]-2,2',5'-trioxospiro[indole-3,3'-pyrrolidin]-1(2H)-yl]acetic acid.

In a third aspect, the invention provides the use of a Spiro derivative according to Formula (I), (I') or its sub-Formulae (Ia, Ib, Ic, Id), for the preparation of a medicament for the treatment and/or prevention of a disease selected from allergic diseases such as allergic asthma, allergic rhinitis, allergic conjunctivitis, and inflammatory dermatoses such as atopic dermatitis, contact hypersensitivity, allergic contact dermatitis, chronic urticaria/chronic idiopathic/autoimmune urticaria, drug-induced exanthems (e.g. toxic epidermal necrolysis or Lyell's syndrome/Stevens-Johnson syndrome/drug hypersensitivity syndrome), photodermatosis or polymorphous light eruption (e.g. photo-irritant contact dermatitis; photoallergic contact dermatitis; chronic actinic dermatitis), and myositis, neurodegenerative disorders such as neuropatic pain and other diseases with an inflammatory component such as rheumatoid arthritis, multiple sclerosis, osteoarthritis, and inflammatory bowel disease (IBD) and other diseases and disorders associated with CTRH2 activity. In a preferred embodiment the spiro derivative is selected from Formulae (Ia-1), (Ia-2), (Ib-1), (Ib-2), (Ic-1), (Ic-2), (Id-1) or (Id-2).

In a forth aspect, the invention provides a method for treating and/or preventing a patient suffering from a disease selected from allergic diseases such as allergic asthma, allergic rhinitis, allergic conjunctivitis, and inflammatory dermatoses such as atopic dermatitis, contact hypersensitivity, allergic contact dermatitis, chronic urticaria/chronic idiopathic/autoimmune urticaria, drug-induced exanthems (e.g. toxic epidermal necrolysis or Lyell's syndrome/Stevens-Johnson syndrome/drug hypersensitivity syndrome), photodermatosis or polymorphous light eruption (e.g. photo-irritant contact dermatitis, photoallergic contact dermatitis, chronic actinic dermatitis), and myositis, neurodegenerative disorders such as neuropatic pain and other diseases with an inflammatory component such as rheumatoid arthritis, multiple sclerosis, osteoarthritis, and inflammatory bowel disease (IBD) and other diseases and disorders associated with CTRH2 activity, by administering a spiro derivative according to Formula (I), (I') or its sub-Formulae (Ia, Ib, Ic, Id). In a preferred embodiment the spiro derivative is selected from Formulae (Ia-1), (Ia-2), (Ib-1), (Ib-2), (Ic-1), (Ic-2), (Id-1) or (Id-2).

The term "preventing", as used herein, should be understood as partially or totally preventing, inhibiting, alleviating, or reversing one or more symptoms or cause(s) of allergic disease or inflammatory dermatitis.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

In a fifth aspect, the invention provides a pharmaceutical composition comprising a Spiro derivative according to Formulae (I), (I') or its sub-Formulae (Ia), (Ib), (Ic), (Id). In a preferred embodiment the pharmaceutical composition comprises a Spiro derivative of (Ia-1), (Ia-2), (Ib-1), (Ib-2), (Ic-1), (Ic-2), (Id-1) or (Id-2), together with a pharmaceutically acceptable excipient or carrier.

The compounds of the invention are typically administered in form of a pharmaceutical composition. Such compositions can be prepared in a manner well known in the pharmaceutical art and comprise at least one active compound. Generally, the compounds of this invention are administered in a pharmaceutically effective amount.

The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the substituted methylene amide derivative according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate buffered saline or other injectable carriers known in the art. As above mentioned, spiro derivatives of Formula (I) in such compositions is typically a minor component, frequently ranging between 0.05 to 10% by weight with the remainder being the injectable carrier and the like.

The above-described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In a sixth aspect, the invention provides a method of synthesis of a compound according to Formulae (I) or (I') or its sub-Formulae (Ia, Ib, Ic, Id). In a preferred embodiment the Spiro derivative is selected from Formulae (Ia-1), (Ia-2), (Ib-1), (Ic-1), (Ic-2), (Id-1) or (Id-2).

The Spiro derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approaches for obtaining compounds of Formula (Ia) are depicted in Schemes 1a-1c. Therein, spiro-indolinone derivatives according to the general formula Ia, whereby the substituents R', $R^2$ and $R^3$ are as above defined, may be prepared in 6 chemical steps, from custom made or commercially available isatin VIII following in one case two different synthetic protocols highlighted as route A and B or from custom made or commercially available oxoindole XIX, as outlined in the schemes 1a to 1c and 2 to 6 here below.

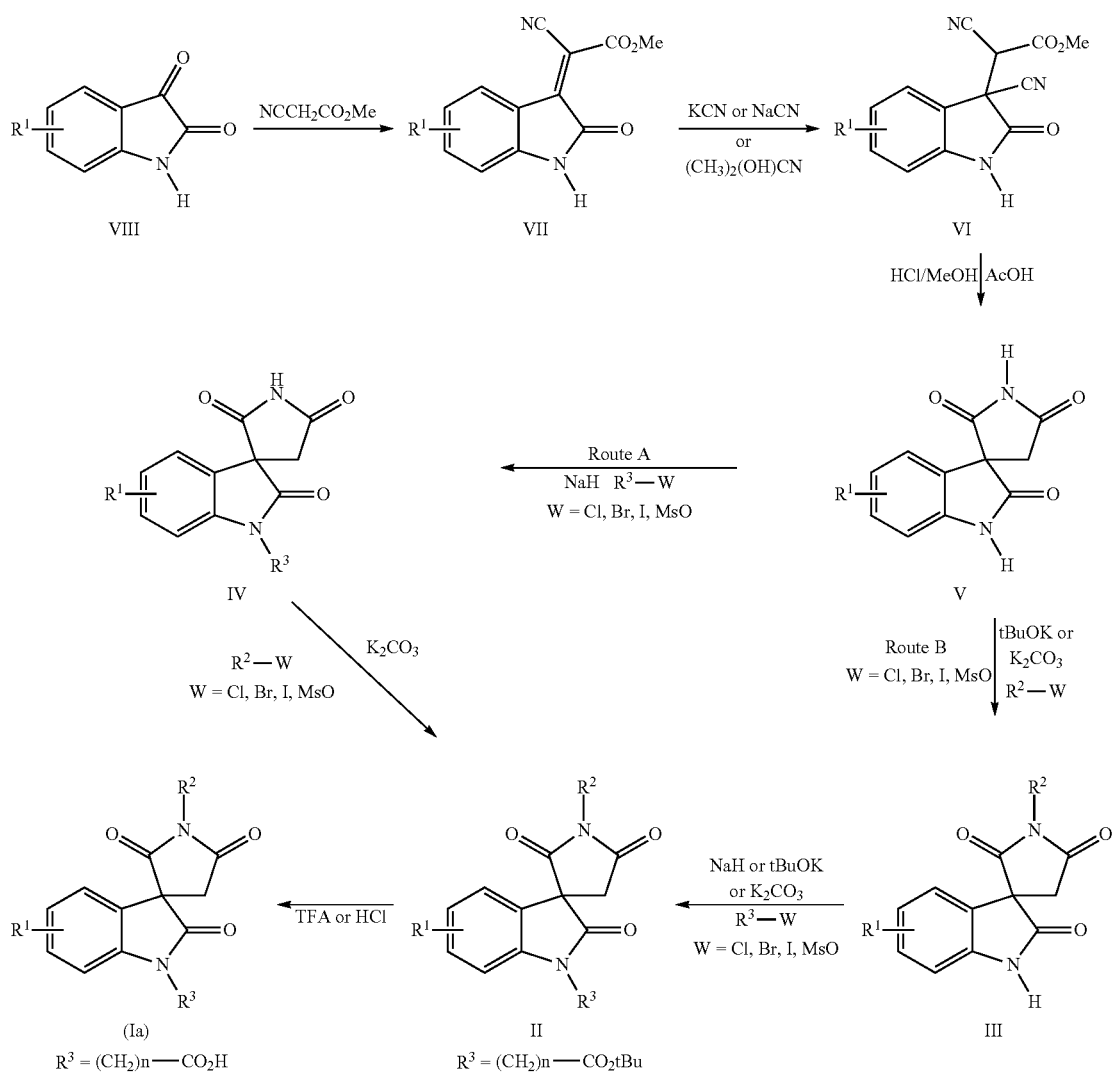

Scheme 1a

According to the first approach, the isatin derivatives VIII wherein R' is defined as above are reacted with methylcyanoacetate to undergo a Knoevenagel reaction, in presence of a suitable base (e.g. piperidine) and under refluxing conditions, to give the corresponding indolinone derivatives VII. The intermediate compounds VI were obtained after treatment of indolinone derivatives VII with a suitable cyanide, e.g. potassium cyanide, sodium cyanide or acetone cyanohydrine at room temperature overnight or under refluxing conditions within a shorter period in methanol as solvent. Both steps can equally be carried out sequential or combined to a one-pot process. The spiroindolinone derivatives V were isolated after cyclisation of intermediate compounds VI under acidic conditions, preferably in a mixture of hydrogen chloride and methanol. This reaction may be performed in solvents like methanol, ethanol or isopropanol at room temperature over time depending on the intrinsic reactivity of compounds VI, and also required the need of traditional thermic heating method, using standard conditions well known to the person skilled in the art as shown in Scheme 2, below:

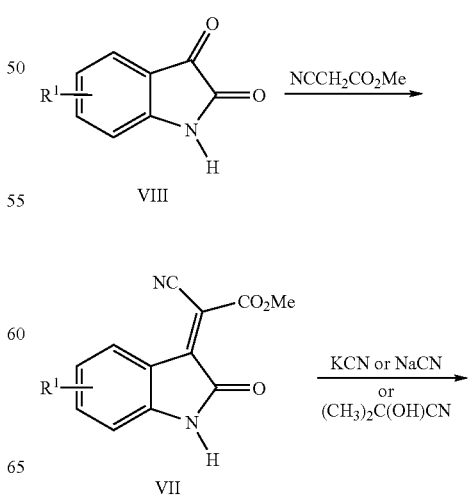

Scheme 2

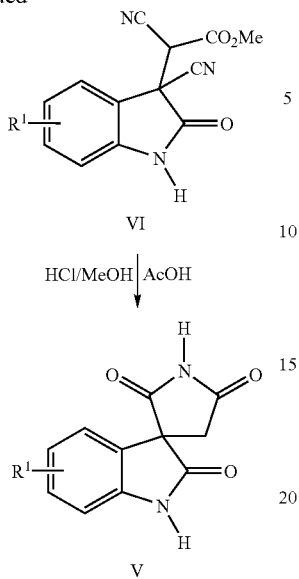

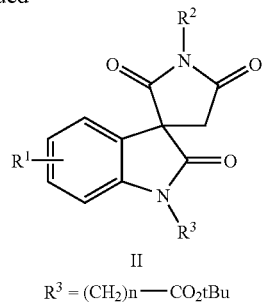

The second method consists in route B as shown in Scheme 4, starting from spiroindolinone derivatives V, the spiroindolinone compounds II were isolated following sequential alkylations. The alkylation exclusively occurs on the nitrogen of the succinimide ring first using a suitable base, preferentially potassium carbonate in DMF in presence of alkylating agents such as alkyl chlorides, bromides, iodides or mesylates, wherein $R^2$ is defined as above, allowing to obtain the intermediate spiroindolinone compounds III. In a following step, the spiroindolinone intermediates III, may be treated with various nucleophiles, e.g. alkyl chlorides, bromides, iodides or mesylates in presence of a base such as potassium carbonate, potassium tert-butoxide or sodium hydride in solvents such as anhydrous N,N-dimethylformamide or tetrahydrofuran, preferentially at room temperature. Following this 2-step procedure the spiroindolinone derivatives II were isolated, using standard conditions well known to the person skilled in the art as shown in the Scheme 4, below. Both steps can be equally be run as one-pot process.

The spiroindolinone derivatives II are obtained following two different methods. The first method consists in route A as shown in Scheme 3, starting from spiroindolinone derivatives V, the spiroindolinone compounds II were isolated following sequential alkylations. The alkylation occurs on the nitrogen of the indolinone ring first using a suitable base, e.g. sodium hydride in DMF in presence of a suitable alkylating agent such as alkyl chlorides, bromides, iodides or mesylates, wherein $R^3$ is defined as above, allowing to obtain the intermediate Spiro indolinone compounds IV. In a subsequent step, the spiroindolinone intermediates IV were treated with an alkylating agent such as alkyl chlorides, bromides, iodides or mesylates, wherein $R^2$ is defined as above, in presence of a suitable base, e.g. potassium carbonate as a base in a suitable solvent, e.g. N,N-dimethylformamide, at room temperature, by traditional thermic method or using microwave technology. Following this 2-step process the spiroindolinone derivatives II were isolated, using standard conditions well known to the person skilled in the art as shown in the Scheme 3, below.

Scheme 4

Route B

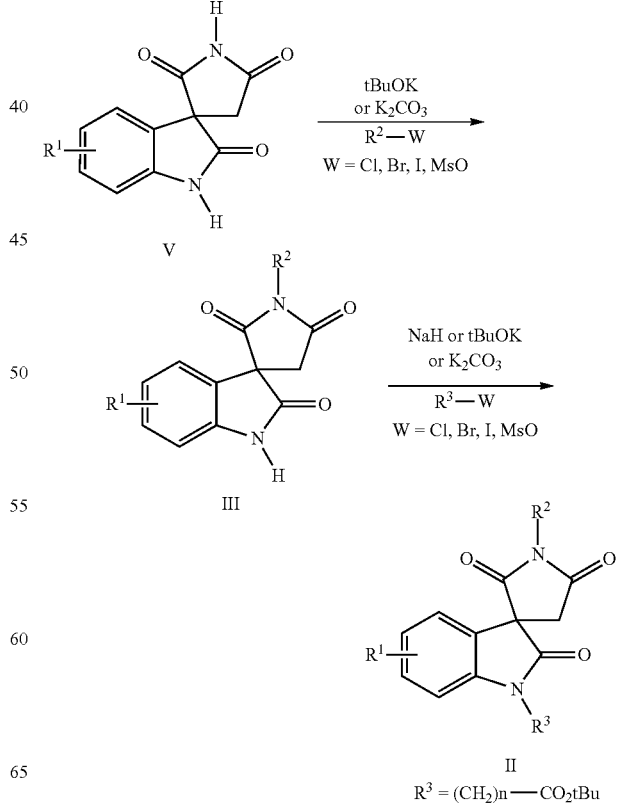

Scheme 3

Route A

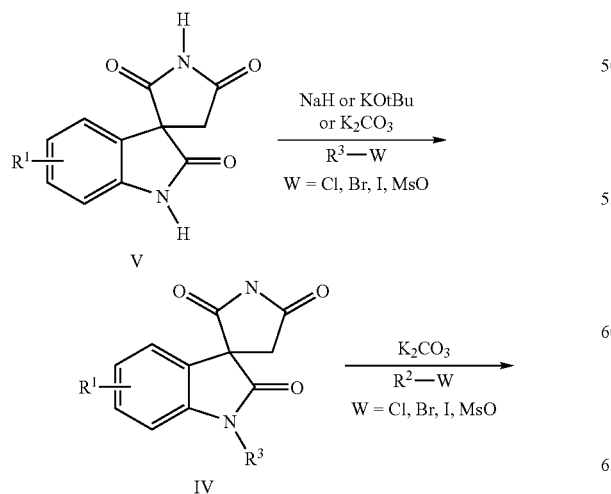

One additional aspect relative to route B consists in obtaining spiroindolinone derivatives II using tert-butyl acrylate as the alkylating agent. In this specific step, the spiroindolinone intermediates III, may be treated with tert-butyl acrylate in presence of suitable bases, e.g. sodium hydride, potassium tert-butoxide or potassium carbonate in anhydrous solvents, such as tetrahydrofuran or DMF at room temperature, allowing to isolate the spiroindolinone derivatives II after flash chromatography purification techniques, using standard conditions well known to the person skilled in the art as shown in the Scheme 5, below.

e.g. trifluoro acetic acid or hydrogen chloride, to deprotect the tert-butyl ester derivatives II, and to give the expected spiroindolinone derivatives Ia. This reaction can be performed at various temperatures and in various solvents e.g. dichloromethane, dioxane or tetrahydrofuran, using standard conditions well known to the person skilled in the art.

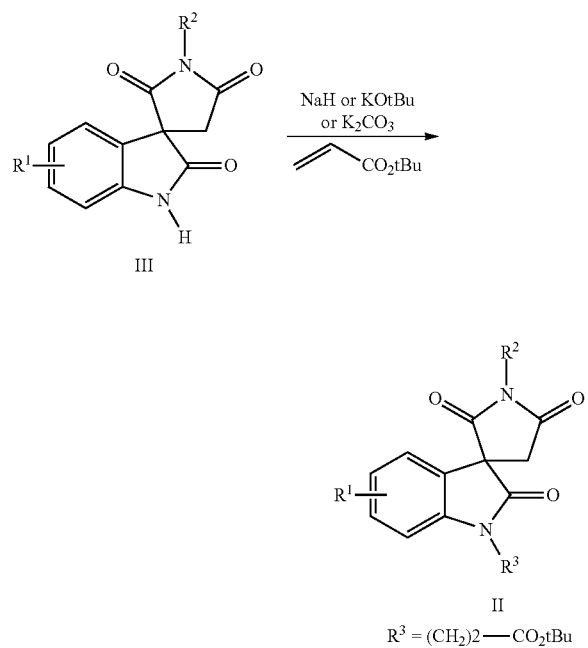

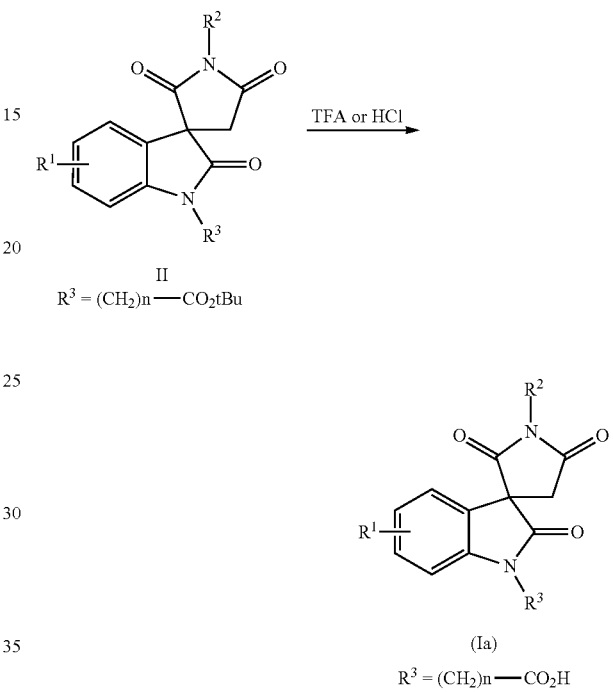

In a final step, as shown in Scheme 6, the spiroindolinone derivatives of formula Ia, may be treated with various acids, A second general approach for obtaining compounds of Formula (Ia) is depicted in Scheme 1b. Therein, spiroindolinone derivatives according to the general formula Ia, whereby the substituents $R^1$, $R^2$ and $R^3$ are as above defined, may equally be prepared in 6 chemical steps, from custom made or commercially available isatin VIII following the synthetic protocols outlined in scheme 1b here below.

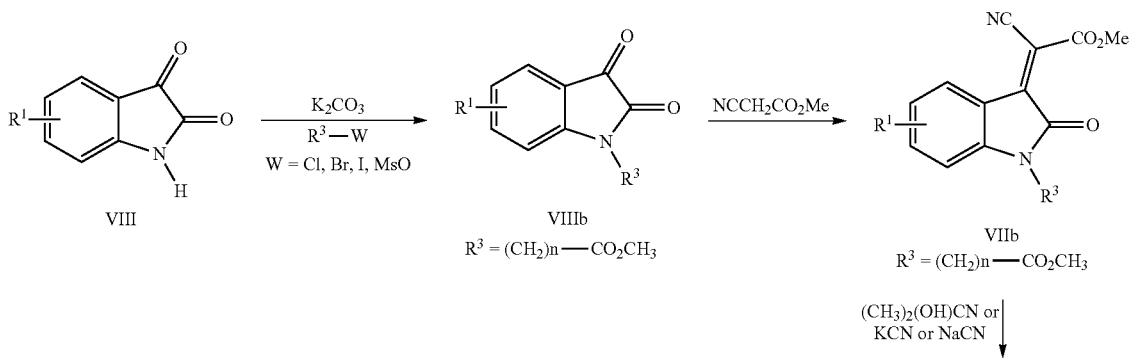

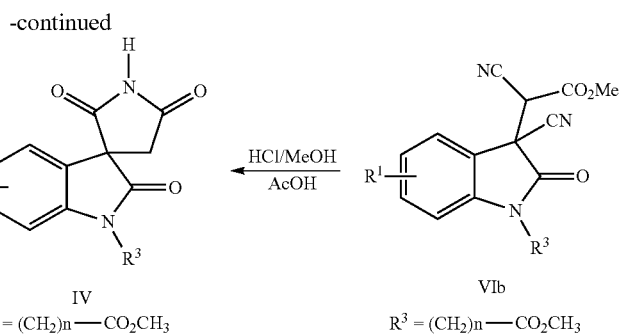

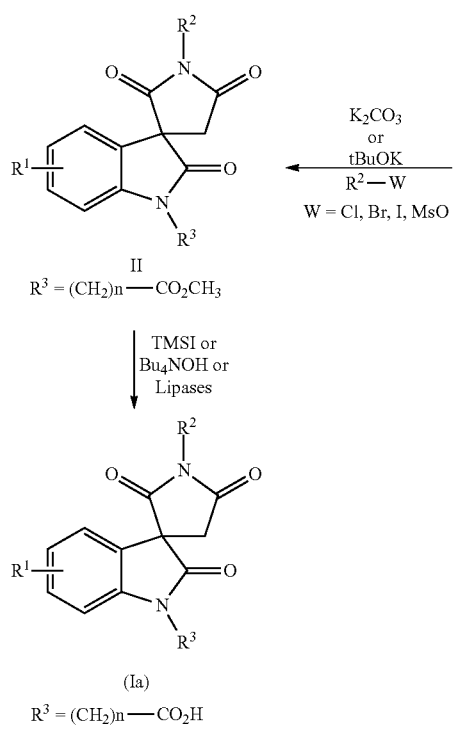

In a more specific method, the isatin derivatives VIII wherein $R^1$ is defined as above are alkylated using a suitable base, preferentially potassium carbonate in DMF in presence of suitable alkylating agents such as alkyl chlorides, bromides, iodides or mesylates, wherein $R^3$ is defined as above to give the corresponding isatin derivatives VIIIb. The indolinone compounds VIIb were obtained after Knoevenagel condensation with methylcyanoacetate in presence of a suitable base (e.g. piperidine) under refluxing conditions. The intermediate derivatives VIb were isolated after treatment of the indolinone compounds VIIb preferentially with acetone cyanohydrine in presence of a suitable base such as potassium carbonate in solvents like tetrahydrofuran or methanol using traditional thermic methods. Inorganic cyanides such as potassium or sodium cyanides may equally be used under refluxing conditions in methanol as solvent. The spiroindolinone derivatives IV were obtained after cyclization of intermediate derivatives VIb under acidic conditions, preferably in a mixture of hydrogen chloride and methanol applying traditional thermic methods well known to the person skilled in the art. Alkylation of spiroindolinone derivatives IV was achieved using a suitable base, e.g. potassium carbonate or potassium tert-butoxide in DMF in presence of a suitable alkylating agent such as alkyl chlorides, bromides, iodides or mesylates, wherein $R^2$ is defined as above, allowing to isolate the intermediate spiroindolinone compounds II.

In a final step, as shown in Scheme 1b, the spiroindolinone derivatives of Formula (Ia), may be obtained after treatment of the alkyl ester derivatives II with either Lewis acids, such as trimethylsilyl iodide, bases, e.g. tetrabutylammonium hydroxide or under enzymatic conditions well known to the person skilled in the art.

A third general approach for obtaining compounds of Formula (Ia) is depicted in Scheme 1c. Therein, spiro-indolinone derivatives according to the general formula Ia, whereby the substituents R', $R^2$ and $R^3$ are as above defined, may equally be prepared in 6 to 7 chemical steps, from custom made or commercially available oxoindole XIX as outlined in scheme 1c here below.

Scheme 1c

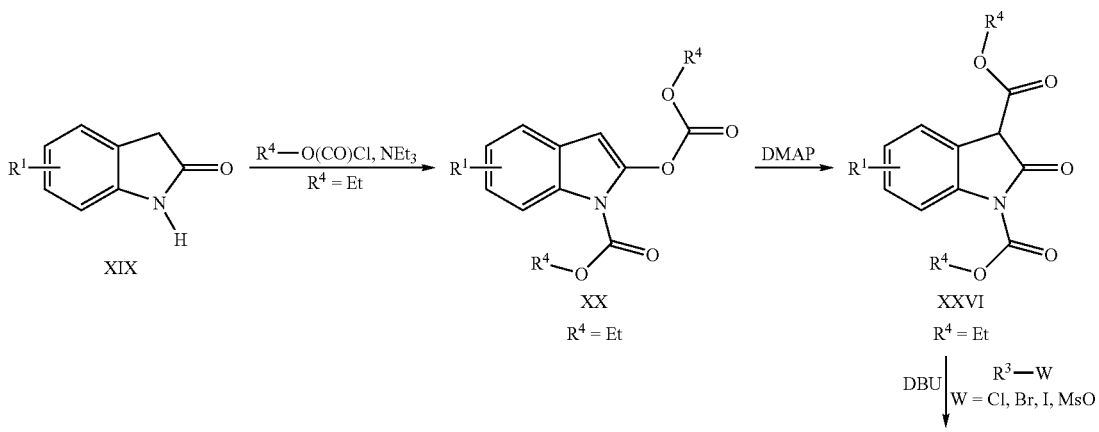

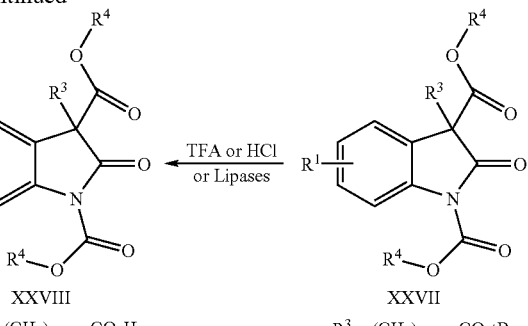
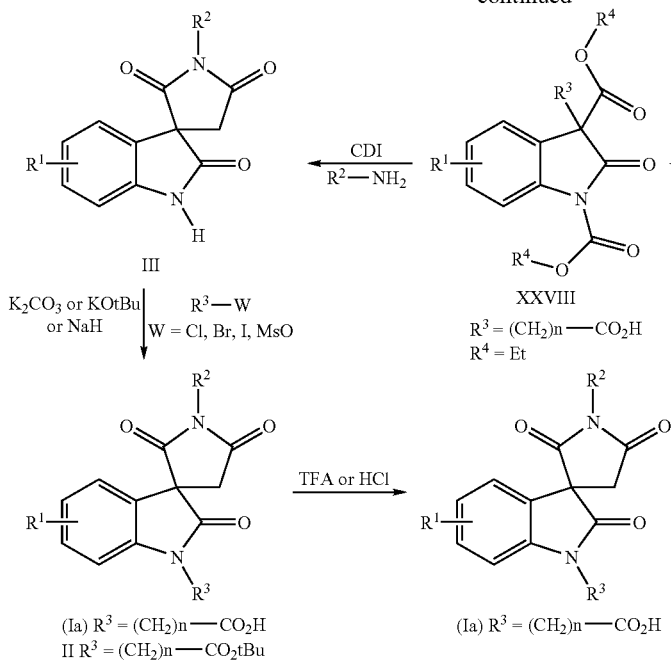

In a more specific method, the oxoindole derivatives XIX wherein R' is defined as above are reacted with ethyl chloroformate in presence of a suitable base such as triethylamine to give the corresponding derivatives XX. Further treatment with DMAP in DMF allowed for rearrangement of the carbonate to give the corresponding derivatives XXVI. Alkylation at position 3 of derivatives XXVI was achieved using a suitable base, perferentially DBU in N,N-dimethylformamide or tetrahydrofuran in presence of suitable alkylating agents such as alkyl chlorides, bromides, iodides or mesylates, wherein $R^3$ is defined as above to give the double-alkylated indolinone derivatives XXVII at room temperature or under refluxing conditions. Treatment with various acids, e.g. trifluoroacetic acid or hydrogen chloride, allowed for the deprotection of the tert-butyl ester derivatives XXVII to isolate the corresponding intermediate carboxylic acids XXVIII. This reaction can be performed at various temperatures and in various solvents, e.g. dichloromethane, dioxane or tetrahydrofuran under standard conditions well known to the person skilled in the art. Alternatively, deprotection may be achieved using lipases well known to the person skilled in the art. Formation of the spiroindolinone system III was achieved by reaction of the carboxylic acids XXVIII with 1,1'-carbonyldiimidazole in tetrahydrofuran in presence of suitable primary alkyl amines wherein $R^2$ is defined as above at room temperature or under refluxing conditions. In a following step, the spiroindolinone intermediates III, may be treated with various nucleophiles, e.g. alkyl chlorides, bromides, iodides or mesylates wherein $R^3$ is defined as above, in presence of a base such as potassium carbonate, potassium tert-butoxide or sodium hydride in solvents such as anhydrous N,N-dimethylformamide or tetrahydrofuran, preferentially at room temperature, by traditional thermic methods or using microwave technology to obtain the spiroindolinone derivatives Ia or II. In a final step, as shown in Scheme 1c, the tert-butylester derivatives II may be treated with various acids, such as trifluoroacetate or hydrogen chloride to achieve deprotection and to give the expected spiroindolinone derivatives Ia. This reaction can be carried out at various temperatures and in various solvents e.g. dichloromethane, dioxane or tetrahydrofuran, using standard conditions well known to the person skilled in the art.

Several other general synthetic approaches for obtaining compounds of Formula (Ib) are depicted in Schemes 7a and 7b. Therein, spiro-indolinone derivatives according to the general formula Ib, whereby the substituents R', $R^2$ and $R^3$ are as above defined, may be prepared in 4 chemical steps, from custom made or commercially available isatin VIII following the synthetic protocols outlined in the schemes 7a and 7b here below.

In a more specific method, the isatin derivatives VIII wherein R' is defined as above is reacted with ammonium carbonate and potassium cyanide to undergo formation of the hydantoin derivatives IX, in presence of ethanol/water as solvents. The spiroindolinone compounds XI were isolated following sequential alkylations. Selective alkylation was possible in this case due to the greater acidity of the imide-type NH compared to either amide, using a suitable base such as potassium tert-butoxide or potassium carbonate in DMF in presence of alkylating agents such as alkyl chlorides, bromides, iodides or mesylates, wherein $R^2$ is defined as above, allowing to obtain the intermediate spiroindolinone compounds X. In a following step, the spiroindolinone intermediates X, may be treated with various electrophiles, e.g. alkyl chlorides, bromides, iodides or mesylates in presence of a base such as potassium tert-butoxide, potassium carbonate or sodium hydride in solvents such as anhydrous N,N-dimethylformamide or tetrahydrofuran, at room temperature, by traditional thermic method or using microwave technology. Following this 2-step process the spiroindolinone derivatives XI were isolated, using standard conditions well known to the person skilled in the art as shown in the Scheme 7a, below.

In a final step, as shown in Scheme 7a, the spiroindolinone derivatives of formula Ib, may be treated with various acids, e.g. trifluoroacetic acid or hydrogen chloride, to deprotect the tert-butyl ester derivatives XI, and to give the expected spiroindolinone derivatives Ib. This reaction can be performed at various temperatures and in various solvents e.g. dichloromethane, dioxane or tetrahydrofurane, using standard conditions well known to the person skilled in the art.

Scheme 7a

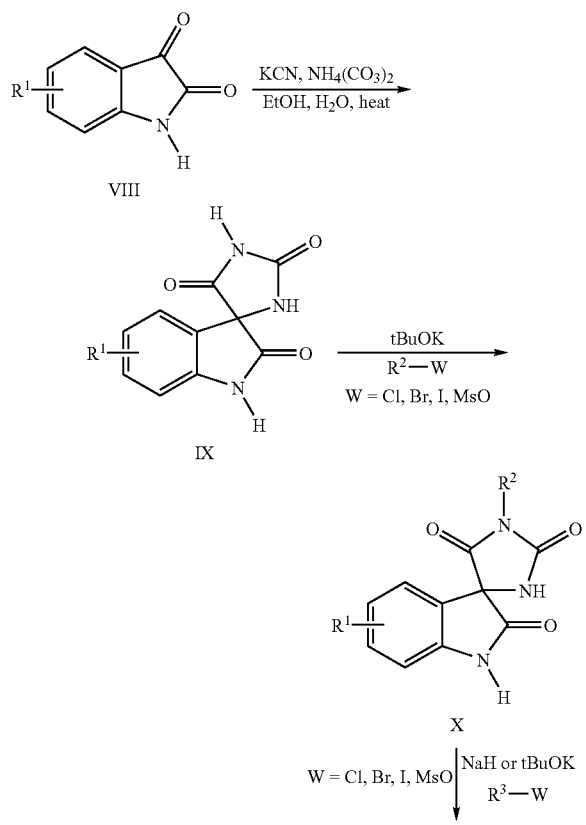

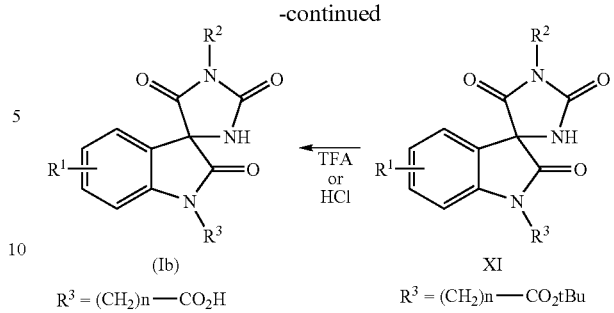

Alternatively, the isatin derivatives VIII wherein $R^1$ is defined as above are alkylated using a suitable base, preferentially potassium carbonate in DMF in presence of suitable alkylating agents such as alkyl chlorides, bromides, iodides or mesylates, wherein $R^3$ is defined as above to give the corresponding isatin derivatives VIIIb. The isatin derivatives VIIIb are further reacted with ammonium carbonate and potassium cyanide to undergo formation of the hydantoin derivatives IXb, in presence of ethanol/water as solvents. The spiroindolinone compounds XI were isolated after alkylation using a suitable base, preferentially potassium carbonate in DMF in presence of alkylating agents such as alkyl chlorides, bromides, iodides or mesylates, wherein $R^2$ is defined as above.

In a final step, as shown in Scheme 7b, the spiroindolinone derivatives of formula Ib, may be treated with various acids, e.g. trifluoroacetic acid or hydrogen chloride, to deprotect the tert-butyl ester derivatives XI, and to give the expected spiroindolinone derivatives Ib. This reaction can be performed at various temperatures and in various solvents e.g. dichloromethane, dioxane or tetrahydrofuran, using standard conditions well known to the person skilled in the art.

Scheme 7b

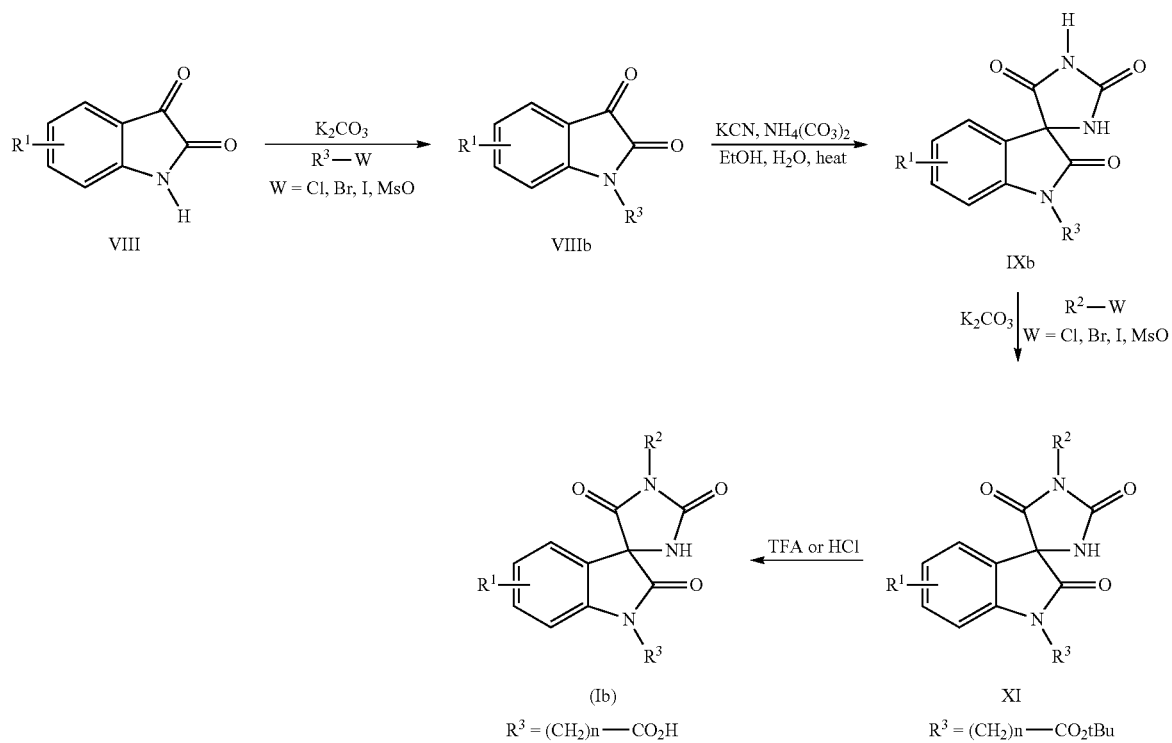

Another general synthetic approach for obtaining compounds of Formula (Ic) is depicted in Scheme 8. Therein, spiro-indolinone derivatives according to the general formula Ic, whereby the substituents R', $R^2$ and $R^3$ are as above defined, may be prepared in 8 chemical steps, from custom made derivatives VII (Scheme 1, 2) following the synthetic protocols outlined in the schemes 8 here below.

In a more specific method, the derivatives VII wherein R' is defined as above is reacted with nitromethane, in presence of piperidine as base, to give the corresponding derivatives XII. The spiroindolinone compounds XIV were isolated following a two sequential steps process. Hydrolysis of the ester derivatives XII with sodium or potassium hydroxide in methanol gave the intermediate of synthesis XIII, which were further decarboxylated by heating at 160 degrees in high boiling point solvents such as dimethylformamide. The derivatives XIV were isolated after precipitation and washings processes as described in the experimental section. Further treatment of derivatives XIV with palladium dichloride with a large excess of acetamide in a mixture of solvents tetrahydrofurane-water gave the corresponding primary amide derivatives XV. Formation of the pyrrolidinone ring was achieved by reaction of primary amide derivatives XV with zinc in acetic acid leading to reduction of the nitro moiety to primary amine followed by spontaneous cyclisation to give the tricyclic derivatives XVI. The spiroindolinone compounds XVIII were isolated following sequential alkylations. The alkylation occurs on the nitrogen of the indolinone ring first using a suitable base, e.g. potassium tert-butoxide in DMF in presence of a suitable alkylating agent such as alkyl chlorides, bromides, iodides or mesylates, wherein $R^3$ is defined as above, allowing to obtain the intermediate spiro indolinone compounds XVII. In a subsequent step, the spiroindolinone intermediates XVII were treated with an alkylating agent such as alkyl chlorides, bromides, iodides or mesylates, wherein $R^2$ is defined as above, in presence of a suitable base, e.g. sodium hydride or potassium tert-butoxide as a base in a suitable solvent, e.g. N,N-dimethylformamide or tetrahydrofuran, at room temperature, by traditional thermic method or using microwave technology. Following this 2-step process the spiroindolinone derivatives XVIII were isolated, using standard conditions well known to the person skilled in the art as shown in the Scheme 8, below.

In a final step, as shown in Scheme 8, the spiroindolinone derivatives of formula Ic, may be treated with various acids, e.g. trifluoro acetic acid or hydrogen chloride, to deprotect the tert-butyl ester derivatives XVIII, and to give the expected spiroindolinone derivatives Ic. This reaction can be performed at various temperatures and in various solvents e.g. dichloromethane, dioxane or tetrahydrofurane, using standard conditions well known to the person skilled in the art.

Scheme 8

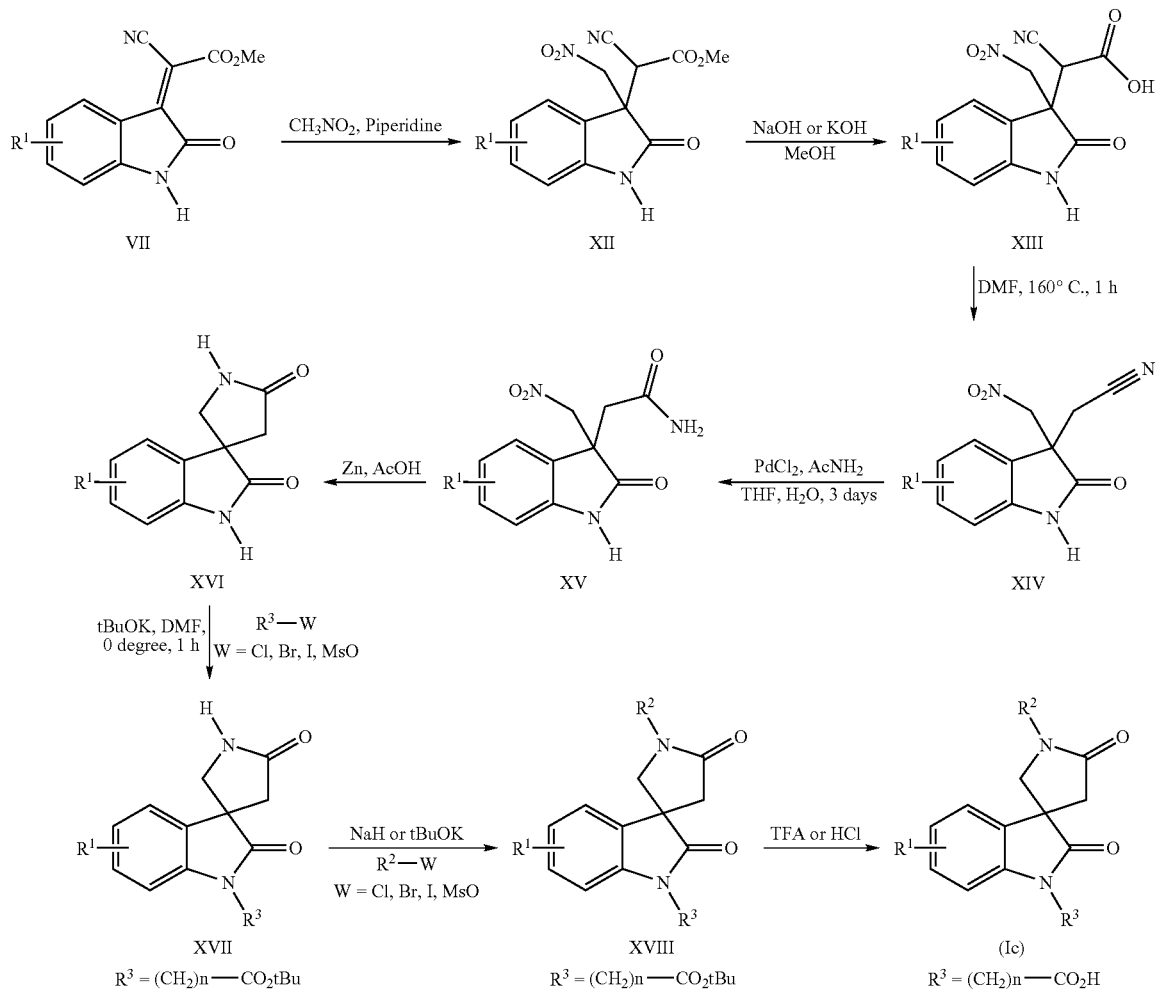

Another general synthetic approach for obtaining compounds of Formula (Id) is depicted in Scheme 9. Therein, spiro-indolinone derivatives according to the general formula Id, whereby the substituents R', $R^2$ and $R^3$ are as above defined, may be prepared in 7 chemical steps, from commercial 2-oxindole derivatives XIX following the synthetic protocols outlined in the schemes 9 here below.

In a more specific method, the derivatives XIX wherein $R^1$ is defined as above is reacted with ethyl or benzyl chloroformate, in presence of triethylamine as base, to give the corresponding derivatives XX. Further treatment with ammonia in methanol allowed deprotection of the carbonate to give the corresponding derivatives XXI. Formation of the pyrrolidinone ring was achieved by reaction of derivatives XXI with 2-bromoethyl isocyanate, in presence of sodium hydride, in dimethylformamide to give the tricyclic derivatives XXII. Cleavage of the carbamate protecting group was achieved with platinum oxide in dimethylfomamide under hydrogen pressure or with potassium hydroxide in ethanol-water, in the case of benzyl carbamate or ethyl carbamate respectively. Following these procedures the derivatives XIII were isolated. The spiroindolinone compounds XXV were isolated following sequential alkylations. The alkylation occurs on the nitrogen of the indolinone ring first using a suitable base, e.g. potassium tert-butoxide in DMF in presence of a suitable alkylating agent such as alkyl chlorides, bromides, iodides or mesylates, wherein $R^3$ is defined as above, allowing to obtain the intermediate spiro indolinone compounds XXIV. In a subsequent step, the spiroindolinone intermediates XXIV were treated with an alkylating agent such as alkyl chlorides, bromides, iodides or mesylates, wherein $R^2$ is defined as above, in presence of a suitable base, e.g. sodium hydride or potassium tert-butoxide as a base in a suitable solvent, e.g. N,N-dimethylformamide or tetrahydrofuran, preferentially at room temperature. Following this 2-step process the spiroindolinone derivatives XXV were isolated, using standard conditions well known to the person skilled in the art as shown in the Scheme 9, below.

In a final step, as shown in Scheme 9, the spiroindolinone derivatives of formula Id, may be treated with various acids, e.g. trifluoro acetic acid or hydrogen chloride, to deprotect the tert-butyl ester derivatives XXV, and to give the expected spiroindolinone derivatives Id. This reaction can be performed at various temperatures and in various solvents e.g. dichloromethane, dioxane or tetrahydrofurane, using standard conditions well known to the person skilled in the art.

Scheme 9

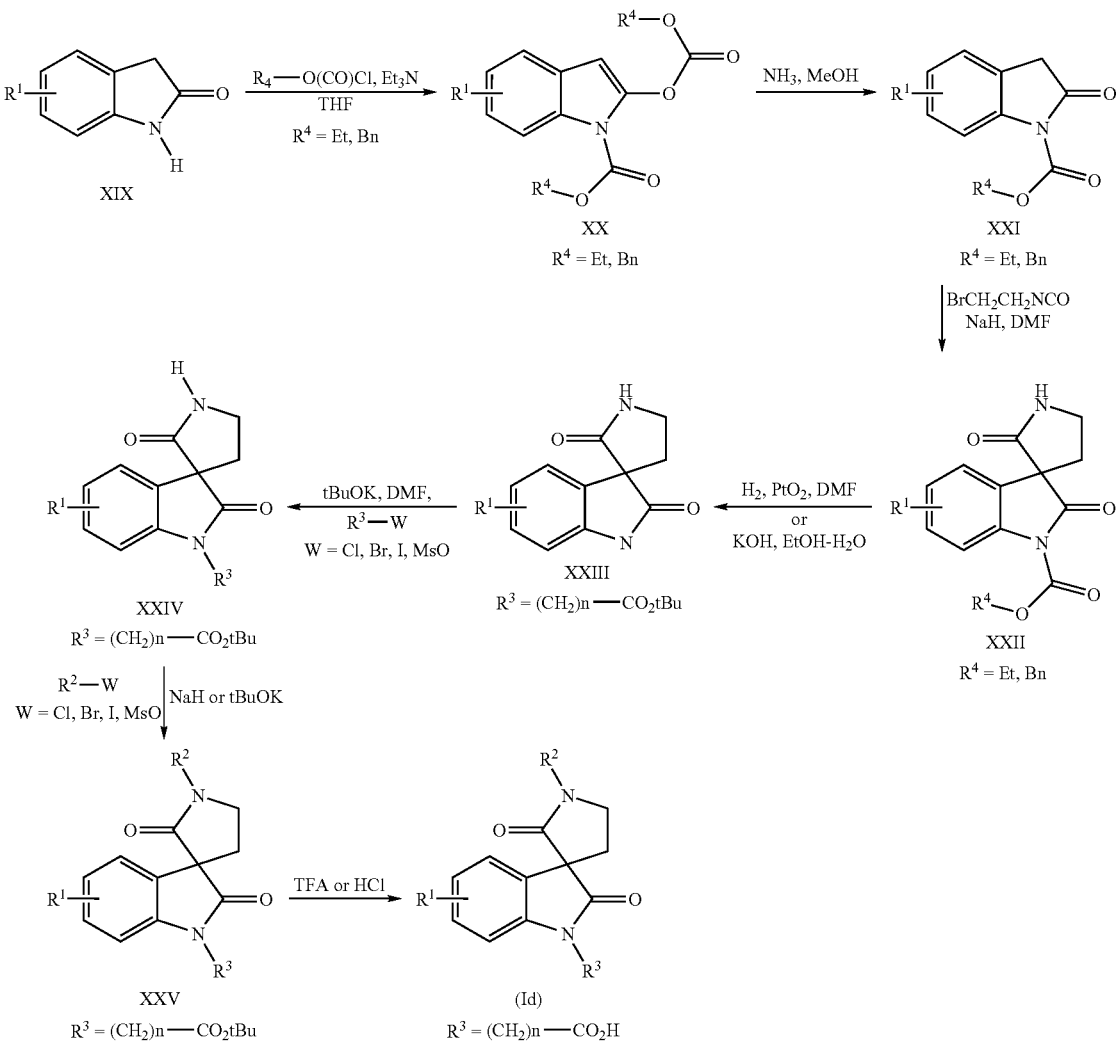

The following abbreviations refer to the abbreviations used below:

min (minute), hr (hour), g (gram), MHz (Megahertz), ml (milliliter), mmol (millimole), mM (millimolar), RT (room temperature), AcNH$_2$ (Acetamide), AcOH (Acetic acid), ATP (Adenoside Triphosphate), BSA (Bovine Serum Albumin), Bu$_4$NOH (Tetrabutylammonium hydroxide), CDI (1,1'-Carbonyldiimidazole), DBU (1,8-Dizabicyclo[5.4.0]undec-7-ene), DCM (Dichloromethane), DIPEA (di-isopropyl ethylamine), DMAP (4-Dimethylaminopyridine), DMSO (Dimethyl Sulfoxide), DMF (N,N-Dimethylformamide), CH$_3$NO$_2$ (Nitromethane), CsCO$_3$ (Cesium carbonate), cHex (Cyclohexanes), Et$_3$N (Triethylamine), EtOAc (Ethyl acetate), EtOH (Ethanol), HCl (hydrogen chloride), K$_2$CO$_3$ (Potassium Carbonate), NaI (Sodium Iodine), KCN, (Potassium cyanide), MeOH (Methanol), MgSO$_4$ (Magnesium sulfate), NH$_3$ (ammonia), NaH (Sodium hydride), NaHCO$_3$ (Sodium bicarbonate), NH$_4$Cl (Ammonium chloride), NH$_4$(CO$_3$)$_2$ (ammonium carbonate), TEA (Triethyl amine), TFA (Trifluoroacetic acid), THF (Tetrahydrofuran), tBuOK (Potassium tert-butoxide), PdCl$_2$ (Palladium dichloride), PetEther (Petroleum ether), PtO$_2$ (Platinium oxide), TBME (tert-Butyl Methyl Ether), TMSI (Trimethylsilyl iodide), Zn (Zinc powder), rt (room temperature). HPLC (High Performance Liquid Chromatography), FC (Flash Chromatography on silica gel), MS (Mass Spectrometry), NMR (Nuclear Magnetic Resonance), PBS (Phosphate Buffered Saline), SPA (Scintillation Proximity Assay), TLC (Thin Layer Chromatography), UV (Ultraviolet).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

EXPERIMENTAL PART

The HPLC, NMR and MS data provided in the examples described below are obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz. Chiral analytical HPLC are performed using a Chiralpak AD-H 250×4.6 mm column, mobile phase ethanol/formic acid 100:1.

The preparative HPLC purifications are performed with HPLC Waters Prep LC 4000 System equipped with columns Prep Nova-Pak®HR C186 μm 60 Å, 40×30 mm (up to 100 mg) or with XTerra® Prep MS C8, 10 mm, 50×300 mm (up to 1 g). All the purifications are performed with a gradient of MeCN/H$_2$O 0.09% TFA. The semi-preparative reverse-phase HPLC are performed with the Biotage Parallex Flex System equipped with columns Supelcosil™ ABZ+Plus (25 cm×21.2 mm, 12 μm); UV detection at 254 nm and 220 nm; flow 20 mL/min (up to 50 mg). TLC Analysis is performed on Merck Precoated 60 F$_{254}$ plates. Purifications by flash chromatography are performed on SiO$_2$ support, using cyclohexane/EtOAc or DCM/MeOH mixtures as eluents.

Intermediate 1: methyl (2Z)-(5-chloro-2-oxo-1,2-dihydro-3H-indol-3-ylidene)(cyano)acetate (cf. Schemes 1, 2, compound VII)

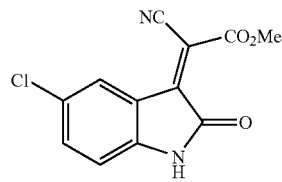

A stirred mixture of 5-chloro-1H-indole-2,3-dione, starting material VIII, (90.8 g, 0.5 mol) and methyl cyanoacetate (44.1 ml, 0.5 mol) in methanol (1000 ml) was treated with piperidine (2 ml) and heated under reflux for 5 hours before standing overnight at ambient temperature. The crude (5-chloro-2-oxo-1,2-dihydro-indol-3-ylidene)-cyanoacetic acid methyl ester was removed by filtration, washed with cold methanol (2×150 ml) and dried in vacuo to give 117.6 g (90%) of a dark purple solid. This was a 6.5:1 mixture of geometric isomers which was sufficiently pure by $^1$H NMR for subsequent reaction.

$^1$H NMR (400 MHz, DMSO); 4.12 and 4.18 (2s, 3H), 7.14 and 7.17 (2d, 1H), 7.65 and 7.75 (2m, 1H), 8.00 and 8.48 (2s, 1H), 11.35 and 11.45 (2br s, 1H). MS (ESI$^-$): 261.

Intermediate 2: methyl (2Z)-cyano(5-methoxy-2-oxo-1,2-dihydro-3H-indol-3-ylidene)acetate; (cf. Schemes 1, 2, compound VII)

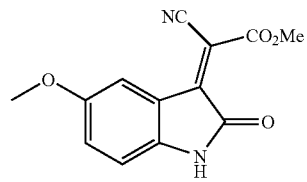

Following the general method as outlined for Intermediate 1, starting from 5-methoxy-1H-indole-2,3-dione and methyl cyanoacetate, the title compound was isolated, after evaporation, as a dark purple solid in 88% yield. This was a 4.5:1 mixture of geometric isomers (99% purity by HPLC).

¹H NMR (400 MHz, DMSO); 3.76 and 3.80 (2s, 3H), 3.92 and 4.00 (2s, 3H), 6.82 and 6.88 (2d, 1H), 7.12 (m, 1H), 7.40 and 7.78 (2s, 1H), 10.90 (br s, 1H). MS (ESI⁺): 259; MS (ESI⁻): 257.

Intermediate 3: methyl (2Z)-cyano[2-oxo-5-(trifluoromethoxy)-1,2-dihydro-3H-indol-3-ylidene]acetate, (cf. Schemes 1, 2, compound VII)

Following the general method as outlined for Intermediate 1, starting from 5-(trifluoromethoxy)-isatin and methyl cyanoacetate, the title compound was isolated, after evaporation, as a dark purple solid in 77% yield. This was a 7.5:1 mixture of geometric isomers.

¹H NMR (400 MHz, DMSO); 3.75 and 3.80 (2s, 3H), 6.82 and 6.88 (2d, 1H), 7.28 and 7.38 (2d, 1H), 7.58 and 8.12 (2s, 1H), 11.04 and 11.15 (2br s, 1H).

Intermediate 4: methyl (2Z)-(6-chloro-2-oxo-1,2-dihydro-3H-indol-3-ylidene)(cyano)-acetate (cf. Schemes 1, 2, compound VII)

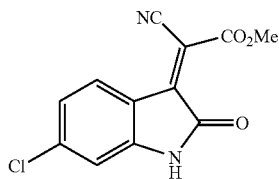

Following the general method as outlined for Intermediate 1, starting from 6-chloro isatin and methyl cyanoacetate, the title compound was isolated, after evaporation, as a dark brown solid in 84% yield. This was a 5.5:1 mixture of geometric isomers (98% purity by HPLC).

¹H NMR (400 MHz, DMSO); 3.76 and 3.82 (2s, 3H), 6.78 and 6.85 (2s, 1H), 7.00 and 7.10 (2d, 1H), 7.72 and 8.08 (2d, 1H), 11.00 and 11.14 (2br s, 1H). MS (ESI⁺): 263; MS (ESI⁻): 261.

Intermediate 5: (5-Chloro-3-cyano-2-oxo-2,3-dihydro-1H-indol-3-yl)-cyanoacetic acid methyl ester, (cf. Schemes 1, 2, compound VI)

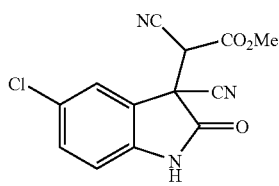

A stirred suspension of crude (5-chloro-2-oxo-1,2-dihydro-indol-3-ylidene)-cyanoacetic acid methyl ester, intermediate 1 (56.0 g, 0.21 mol) in methanol (750 ml) was treated, in portions, with potassium cyanide (13.8 g, 0.21 mol) followed by water (45 ml). The mixture was stirred at ambient temperature for 7 hours and the resultant black solution was left to stand overnight. The solvent was removed in vacuo, water (500 ml) was added and the mixture acidified by the addition of 2M hydrochloric acid [CAUTION: TRACES OF CYANIDE MAY STILL BE PRESENT!]. The mixture was extracted with dichloromethane (3×300 ml). The combined extracts were washed with water (2×300 ml) and dried (MgSO₄). The solvent was removed in vacuo to give the crude (5-chloro-3-cyano-2-oxo-2,3-dihydro-1H-indol-3-yl)-cyanoacetic acid methyl ester as a pale-brown solid (53.3 g, 86%). This was a mixture of diastereomers, which was sufficiently pure by ¹H NMR for subsequent reaction.

¹H NMR (400 MHz, DMSO); 3.62 (s, 3H), 5.72 and 5.82 (2s, 1H), 6.92 (m, 1H), 7.40 (m, 1H), 7.56 and 7.62 (2s, 1H), 11.60 and 11.64 (2s, 1H).

Intermediate 6: methyl cyano(3-cyano-5-methoxy-2-oxo-2,3-dihydro-1H-indol-3-yl)acetate (cf. Schemes 1, 2, compound VI)

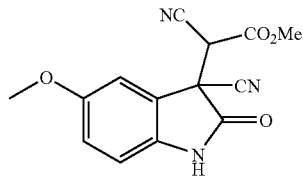

Following the general method as outlined for Intermediate 5, starting from methyl (2Z)-cyano(5-methoxy-2-oxo-1,2-dihydro-3H-indol-3-ylidene)acetate (intermediate 2) and potassium cyanide, the title compound was isolated, after evaporation, as a pale brown solid in 90% yield. This was a mixture of diastereomers.

¹H NMR (400 MHz, DMSO); 3.75, 3.77, 3.80 and 3.82 (4s, 6H), 5.80 and 5.88 (2s, 1H), 6.98 (m, 1H), 7.06 (m, 1H), 7.20 and 7.28 (2s, 1H), 11.42 (s, 1H).

Intermediate 7: methyl cyano[3-cyano-2-oxo-5-(trifluoromethoxy)-2,3-dihydro-1H-indol-3-yl]acetate, (cf. Schemes 1, 2, compound VI)

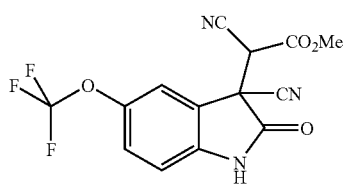

Following the general method as outlined for Intermediate 5, starting from methyl (2Z)-cyano[2-oxo-5-(trifluoromethoxy)-1,2-dihydro-3H-indol-3-ylidene]acetate (intermediate 3) and potassium cyanide, the title compound was isolated, after evaporation, as a pale brown solid in 90% yield. This was a mixture of diastereomers.

¹H NMR (400 MHz, DMSO); 3.76 (s, 3H), 5.88 and 5.98 (2s, 1H), 7.16 (m, 1H), 7.48-7.58 (m, 1H), 7.68 and 7.76 (2s, 1H), 11.78 and 11.82 (2s, 1H).

Intermediate 8: methyl (6-chloro-3-cyano-2-oxo-2,3-dihydro-1H-indol-3-yl)(cyano)acetate (cf. Schemes 1, 2, compound VI)

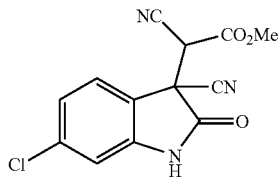

Following the general method as outlined for Intermediate 5, starting from methyl (2Z)-(6-chloro-2-oxo-1,2-dihydro-3H-indol-3-ylidene)(cyano)acetate (intermediate 4) and potassium cyanide, the title compound was isolated, after evaporation, as a light brown solid in 61% yield. This was a mixture of diastereomers.

¹H NMR (400 MHz, DMSO); 3.90 and 3.95 (2s, 3H), 6.00 and 6.05 (2s, 1H), 7.22 (s, 1H), 7.38-7.48 (m, 1H), 7.70 and 7.80 (2d, 1H), 11.90 (s, 1H).

Intermediate 9: 5-Chloro-1H-spiro[indole-3,3'-pyrrolidine]-2,2',5'-trione, (cf. Schemes 1, 2, 3, 4, compound V)

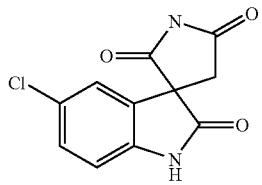

A stirred solution of the crude (5-chloro-3-cyano-2-oxo-2,3-dihydro-1H-indol-3-yl)-cyanoacetic acid methyl ester, intermediate 5 (53.3 g, 0.18 mol) in methanol (450 ml) was cooled in an ice-water bath and saturated with hydrogen chloride gas, keeping the temperature below 20° C. The resultant solution was left to stand at ambient temperature overnight and then heated cautiously under reflux for 5 hours to give a yellow suspension. The solvent was removed in vacuo to give a semi-solid residue, which was mixed with glacial acetic acid (375 ml) and heated under reflux, with stirring, for 16 hours. After cooling in an ice-water bath, the crude 5-chloro-1H-spiro[indole-3,3'-pyrrolidine]-2,2',5'-trione was removed by filtration, washed with cold glacial acetic acid (100 ml) followed by water (100 ml) and then diethyl ether (100 ml) and dried in vacuo to give an off-white solid. A second crop was obtained by removing the solvent in vacuo from the combined acetic acid filtrates and repeating the purification procedure to give a total of 30.5 g (66%). Sufficiently pure by ¹H NMR for subsequent reaction.

¹H NMR (400 MHz, DMSO); 3.00 (d, 1H), 3.20 (d, 1H), 6.92 (d, 1H), 6.35 (m, 1H), 7.75 (s, 1H), 11.00 (br s, 1H), 11.84 (br s, 1H). MS (ESI⁻): 249

Intermediate 10: 5-methoxy-2'H,5'H-spiro[indole-3, 3'-pyrrolidine]-2,2',5'(1H)-trione (cf. Schemes 1, 2, 3, 4, compound V)

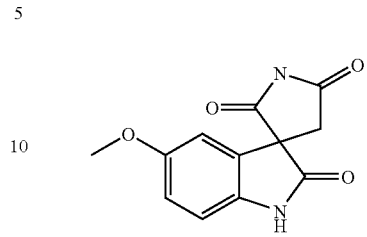

Following the general method as outlined for Intermediate 9, starting from methyl cyano(3-cyano-5-methoxy-2-oxo-2,3-dihydro-1H-indol-3-yl)acetate (intermediate 6) and in presence of hydrogen chloride in methanol, the title compound was isolated, after evaporation, as a pale brown solid in 46% yield (100% purity by HPLC).

¹H NMR (400 MHz, DMSO); 2.86 (d, 1H), 3.05 (d, 1H), 3.62 (s, 3H), 6.74 (m, 2H), 7.15 (s, 1H), 10.52 (s, 1H), 11.67 (br s, 1H). MS (ESI⁻): 245.

Intermediate 11: 5-(trifluoromethoxy)-2'H,5'H-spiro[indole-3,3'-pyrrolidine]-2,2',5'(1H)-trione, (cf. Schemes 1, 2, 3, 4, compound V)

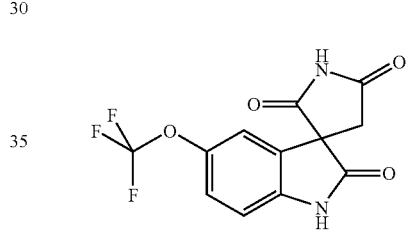

Following the general method as outlined for Intermediate 9, starting from methyl cyano[3-cyano-2-oxo-5-(trifluoromethoxy)-2,3-dihydro-1H-indol-3-yl]acetate (intermediate 7) and in presence of hydrogen chloride in methanol, the title compound was isolated, after evaporation, as an off-white solid in 30% yield (99% purity by HPLC).

¹H NMR (400 MHz, DMSO); 3.00 (d, 1H), 3.20 (d, 1H), 7.02 (d, 1H), 7.32 (m, 1H), 7.75 (d, 1H), 11.05 (br s, 1H), 11.60 (br s, 1H). MS (ESI⁻): 299.

Intermediate 12: 2-chloro-N-(3-chloropyrazin-2-yl) benzenesulfonamide, (cf. Schemes 1, 2, 3, 4, compound V)

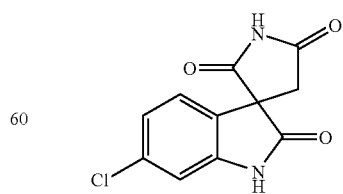

Following the general method as outlined for Intermediate 9, starting from methyl (6-chloro-3-cyano-2-oxo-2,3-dihydro-1H-indol-3-yl)(cyano)acetate (intermediate 8) and in presence of hydrogen chloride in methanol, the title compound was isolated, after evaporation, as an off-white solid in 22% yield (80% purity by HPLC).

$^1$H NMR (400 MHz, DMSO); 3.18 (d, 1H), 3.35 (d, 1H), 7.13 (s, 1H), 7.26 (d, 1H), 7.72 (d, 1H), 11.16 (br s, 1H), 12.00 (br s, 1H). MS (ESI$^-$): 249.

Intermediate 13: (5-Chloro-2,2',5'-trioxo-spiro[indole-3,3'-pyrrolidin]-1-yl)acetic acid tert-butyl ester, (cf. Schemes 1, 3, compound IV)

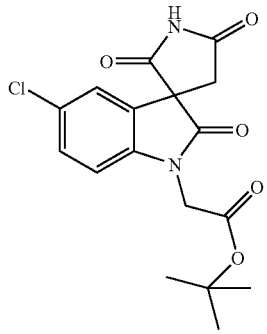

A stirred suspension of sodium hydride (60% dispersion in mineral oil, 1.68 g, 42 mmol) in anhydrous N,N-dimethylformamide (140 ml) was treated with the crude 5-chloro-1H-spiro[indole-3,3'-pyrrolidine]-2,2',5'-trione, intermediate 9 (5.0 g, 19.96 mmol). After stirring at ambient temperature for 40 min, the dark orange solution was cooled in an ice-bath and treated, over 30 min., with a solution of t-butyl bromoacetate (3.24 g, 2.26 ml, 18.96 mmol) in anhydrous N,N-dimethylformamide (46 ml). The resultant dark yellow mixture was allowed to come to ambient temperature and stirred for 4 hours. The resultant mixture was diluted with saturated aqueous ammonium chloride (500 ml) and extracted with ethyl acetate (3×200 ml). The combined extracts were dried (MgSO$_4$) and the solvent removed to give the crude (5-Chloro-2,2',5'-trioxo-spiro[indole-3,3'-pyrrolidin]-1-yl) acetic acid tert-butyl ester which was purified by flash chromatography (silica) eluting with petroleum ether (40-60) containing an increasing amount (0 to 80%) of ethyl acetate. This gave 4.76 g (95%) of a yellow solid.

$^1$H NMR (400 MHz, CDCl$_3$, TMS); 1.50 (s, 9H), 3.03 (d, 1H), 3.38 (d, 1H), 4.22 (d, 1H), 4.54 (d, 1H), 6.73 (d, 1H), 7.22 (d, 1H), 7.35 (m, 1H), 8.32 (br s, 1H). MS (ESI$^-$): 363.

Intermediate 14: 1'-Benzyl-5-chloro-1H-spiro[indole-3,3'-pyrrolidine]-2,2',5'-trione (cf. Schemes 1, 4, 5, compound III)

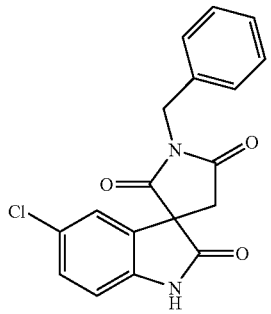

A stirred solution of the crude 5-chloro-1H-spiro[indole-3,3'-pyrrolidine]-2,2',5'-trione, intermediate 9 (800 mg, 3.19 mmol) in anhydrous N,N-dimethylformamide (6 ml) was treated with potassium tert-butoxide (377 mg, 3.19 mmol). After stirring at ambient temperature for 40 min, benzyl bromide (0.38 ml, 3.19 mmol) was added. The mixture was stirred for 2 hours and left to stand overnight. The resultant mixture was diluted with water (50 ml) and extracted with ethyl acetate (3×50 ml). The combined extracts were dried (MgSO$_4$) and the solvent removed in vacuo to give the crude 1'-benzyl-5-chloro-1H-spiro[indole-3,3'-pyrrolidine]-2,2', 5'-trione which was purified by flash chromatography (silica) eluting with petroleum ether (40-60) containing an increasing amount (0 to 75%) of ethyl acetate. This gave 789 mg (73%) of a yellow solid.

$^1$H NMR (400 MHz, CDCl$_3$, TMS); 2.97 (d, 1H), 3.35 (d, 1H), 4.78 (s, 2H), 6.85 (d, 1H), 6.98 (s, 1H), 7.25-7.48 (m, 6H), 8.06 (br s, 1H). MS (ESI$^-$): 339.

Intermediate 15: 3-(1'-Benzyl-5-chloro-2,2',5'-trioxo-spiro[indole-3,3'-pyrrolidin]-1-yl)-propionic acid tert-butyl ester, (cf. Scheme 5, compound II)

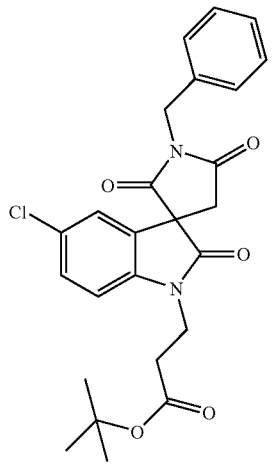

A stirred suspension of sodium hydride (60% dispersion in oil, 7 mg, 0.16 mmol) in anhydrous tetrahydrofuran (2 ml) was treated with 1'-benzyl-5-chloro-1H-spiro[indole-3,3'-pyrrolidine]-2,2',5'-trione, intermediate 14 (50 mg, 0.15 mmol). After stirring at ambient temperature for 30 minutes, tert-butyl acrylate (0.03 ml, 0.19 mmol) was added and the resultant mixture stirred for 2 hours and left to stand at ambient temperature for 18 hours. Water (15 ml) was added and the mixture extracted with ethyl acetate (3×15 ml). The combined extracts were washed with brine (15 ml), dried (MgSO$_4$) and the solvent removed in vacuo to give the crude 3-(1'-Benzyl-5-chloro-2,2',5'-trioxo-spiro[indole-3,3'-pyrrolidin]-1-yl)-propionic acid tert-butyl ester. This was purified by flash chromatography (silica) eluting with petroleum ether (40-60) containing an increasing amount (0 to 50%) of ethyl acetate to give a white solid (37 mg 54%). This was sufficiently pure by $^1$H NMR to take on to the final hydrolysis step.

$^1$H NMR (400 MHz, CDCl$_3$, TMS); 1.41 (s, 9H), 2.63 (t, 2H), 2.93 (d, 1H), 3.31 (d, 1H), 3.98 (t, 2H), 4.75 (s, 2H), 6.96 (m, 2H), 7.29-7.37 (m, 6H).

Intermediate 16: (1'-Benzyl-5-chloro-2,2',5'-trioxo-spiro[indole-3,3'-pyrrolidin]-1-yl)-acetic acid tert-butyl ester, (cf. Schemes 1, 3, 4, compound II)

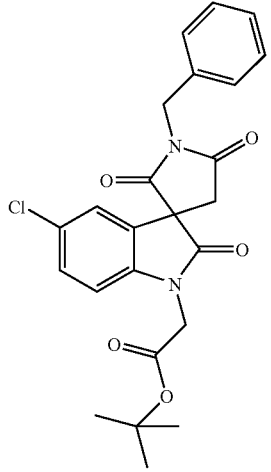

Route A:

A stirred solution of (5-Chloro-2,2',5'-trioxo-spiro[indole-3,3'-pyrrolidin]-1-yl)acetic acid tert-butyl ester, intermediate 13 (100 mg, 0.27 mmol) in anhydrous N,N-dimethylformamide (2.5 ml) was treated with potassium carbonate (114 mg, 0.82 mmol) followed by benzyl bromide (56 mg, 0.04 ml, 0.33 mmol) and heated for 18 hours at 50° C. Water (25 ml) was added and the mixture extracted with ethyl acetate (3×25 ml). The combined extracts were washed with brine (25 ml), dried (MgSO$_4$) and the solvent removed in vacuo to give the crude (1'-Benzyl-5-chloro-2,2',5'-trioxo-spiro[indole-3,3'-pyrrolidin]-1-yl)-acetic acid tert-butyl ester. This was purified by flash chromatography (silica) eluting with petroleum ether (40-60) containing an increasing amount (0 to 50%) of ethyl acetate to give a white solid (104 mg, 83%). This was sufficiently pure by $^1$H NMR to take on to the final hydrolysis step.

Route B:

A stirred suspension of sodium hydride (60% dispersion in oil [116 mg, 2.9 mmol]) in anhydrous tetrahydrofuran (30 ml) was treated with 1'-benzyl-5-chloro-1H-spiro[indole-3,3'-pyrrolidine]-2,2',5'-trione, intermediate 14 (900 mg, 2.64 mmol). After stirring at ambient temperature for 30 min, the clear solution was treated with tert-butyl bromoacetate (0.51 ml, 3.44 mmol). The resultant suspension was stirred for 3 hours and then left to stand overnight. Water (100 ml) was added and the mixture extracted with ethyl acetate (3×100 ml). The combined extracts were washed with brine (100 ml), dried (MgSO$_4$) and the solvent removed in vacuo to give the crude (1'-benzyl-5-chloro-2,2',5'-trioxo-spiro[indole-3,3'-pyrrolidin]-1-yl)-acetic acid tert-butyl ester. This was purified by flash chromatography (silica) eluting with petroleum ether (40-60) containing an increasing amount (0 to 50%) of ethyl acetate to give a white solid (1.088 g, 91%).

$^1$H NMR (400 MHz, CDCl$_3$, TMS); 1.44 (s, 9H), 2.97 (d, 1H), 3.35 (d, 1H), 4.21 (d, 1H), 4.53 (d, 1H), 4.76 (s, 2H), 6.72 (d, 1H), 7.00 (s, 1H), 7.30-7.37 (m, 6H). MS (ESI$^+$):399 (loss of $^t$Bu).

Intermediate 17: (1'-Benzyl-5-chloro-2,2',5'-trioxo-spiro[indole-3,3'-pyrrolidin]-1-yl)-acetic acid ethyl ester, (cf. Schemes 1, 3, 4, compound II)

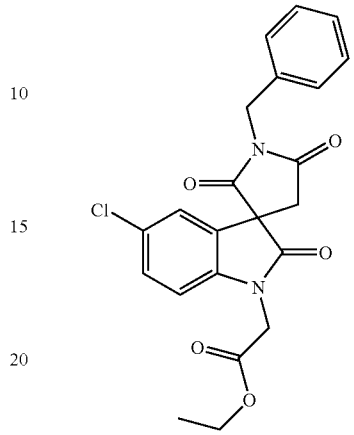

A stirred suspension of sodium hydride (60% dispersion in oil [39 mg, 0.969 mmol]) in anhydrous tetrahydrofuran (10 ml) was treated with 1'-benzyl-5-chloro-1H-spiro[indole-3,3'-pyrrolidine]-2,2',5'-trione, intermediate 14 (300 mg, 0.88 mmol). After stirring at ambient temperature for 30 min, the clear solution was treated with ethyl bromoacetate (0.13 ml, 1.16 mmol). The resultant suspension was stirred for 3 hours and then left to stand overnight. Water (50 ml) was added and the mixture extracted with ethyl acetate (3×50 ml). The combined extracts were washed with brine (50 ml), dried (MgSO$_4$) and the solvent removed in vacuo to give the crude (1'-benzyl-5-chloro-2,2',5'-trioxo-spiro[indole-3,3'-pyrroli-din]-1-yl)-acetic acid ethyl ester. Purification by flash chromatography (silica) eluting with petroleum ether (40-60) containing an increasing amount (0 to 50%) of ethyl acetate, followed by trituration with di-isopropyl ether gave a white solid (264 mg, 70%), m.pt. 143-144° C.

$^1$H NMR (400 MHz; CDCl$_3$; Me$_4$Si): 1.27 (t, 3H), 2.99 (d, 1H), 3.36 (d, 1H), 4.22 (q, 2H), 4.31 (d, 1H), 4.63 (d, 1H), 4.76 (s, 2H), 6.74 (d, 1H), 7.00 (d, 1H), 7.32 (m, 6H).

Intermediate 18

5'-chloro-2H,5H-spiro[imidazolidine-4,3'-indole]-2,2',5(1'H)-trione, (cf. Scheme 7a, compound IX)

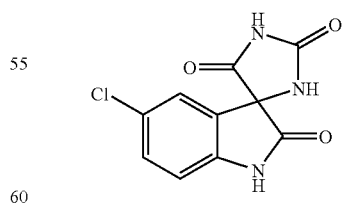

A mixture of 5-chloroisatin (5.00 g; 27.54 mmol), ammonium carbonate (21.14 g; 0.22 mol), and potassium cyanide (2.37 g; 36.35 mmol) in EtOH (130 ml) and water (70 ml) was heated under gentle reflux for 3 h. The mixture was poured into water (400 ml) and acidified with AcOH until a pH of 5. After removal of the organic solvents in vacuo, a solid precipitated and was filtered and dried to give the title compound with 58% yield (HPLC purity 94%). MS (ESI⁻): 250.0

Intermediate 19: 5'-chloro-1-(5-chloro-2-fluorobenzyl)-2H,5H-spiro[imidazolidine-4,3'-indole]-2,2',5 (1'H)-trione, (cf. Scheme7a, compound X)

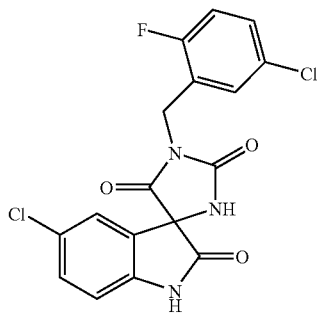

An ice-cold solution of 5'-chloro-2H,5H-spiro[imidazolidine-4,3'-indole]-2,2',5(1'H)-trione, intermediate 18 (500.00 mg; 1.99 mmol) in DMF (10 ml) was treated with potassium carbonate (274.62 mg; 1.99 mmol). The ice bath was removed and the reaction mixture was treated with 5-chloro-2-fluorobenzyl bromide (444.05 mg; 1.99 mmol). After 1.5 h, ethyl acetate was added and the organic phase was washed with water and brine, dried (MgSO₄) and the solvent removed in vacuo to give the crude product as a red solid, which was purified by chromatography (silica) eluting with cyclohexane containing increasing amounts of ethyl acetate (20 to 50%) to give the title compound in 26% yield (HPLC purity 94%). MS (ESI⁺): 394.1; MS (ESI⁻): 392.0

Intermediate 20: tert-butyl [5'-chloro-1-(5-chloro-2-fluorobenzyl)-2,2',5-trioxospiro-[imidazolidine-4,3'-indol]-1' (2'H)-yl]acetate, (cf. Schemes 7a and 7b, compound XI)

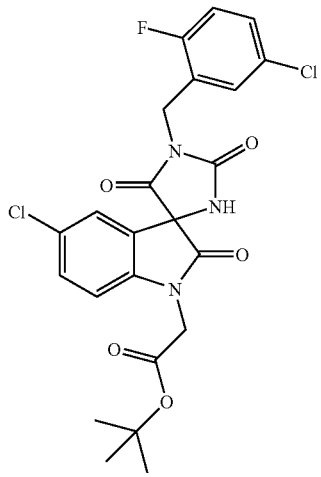

Method A:

An ice cold solution of 5'-chloro-1-(5-chloro-2-fluorobenzyl)-2H,5H-spiro[imidazolidine-4,3'-indole]-2,2',5(1'H)-trione, intermediate 19 (1.100 g; 2.79 mmol) in DMF (10 mL) was treated with sodium hydride (123.89 mg; 3.10 mmol) and stirred for 30 minutes. tert-Butyl bromoacetate (2.11 ml; 2.79 mmol) was added and reaction mixture was stirred at room temperature. Ethyl acetate was added and the organic phase was washed with water and brine, dried (MgSO₄) and the solvent removed in vacuo to give the crude product as a red solid, which was purified by chromatography (silica) eluting with cyclohexane containing increasing amounts of ethyl acetate (20 to 50%) to give the title compound in 12% yield (HPLC purity 98.8%). MS (ESI⁺): 510.2

Method B:

To a solution of tert-butyl (5'-chloro-2,2'5'-trioxospiro [imidazolidine-4,3'-indol]-1'(2'H)-yl)acetate, intermediate 54, (7.90 g, 21.59 mmol) in N,N-dimethylformamide (80 ml) potassium carbonate (3.58 g, 25.91 mmol) was added portionwise at 0-5° C. Stirring was continued at 0-5° C. for 45 minutes and additional 90 minutes at ambient temperature. The suspension was treated with 5-chloro-2-fluorobenzyl bromide and stirred for one hour at ambient temperature. The solid was filtered, the filtrate was partitioned between water (400 ml) and tert-butyl methyl ether (200 ml) and the product was extracted with tert-butyl methyl ether (3×150 ml). The combined extracts were washed with water (400 ml) and dried (MgSO₄) to give a pink residue. Recrystallization from toluene yielded the title compound (6.47 g, 59%) as slightly pink solid (HPLC purity: 96%).

Intermediate 21: 5'-chloro-1-[(5-methyl-3-phenylisoxazol-4-yl)methyl]-2H,5H-spiro[imidazolidine-4, 3'-indole]-2,2',5(1'H)-trione, (cf. Scheme7a, compound X)

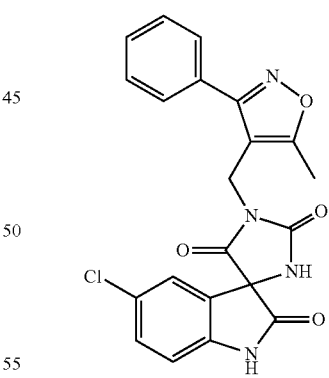

Following the general method as outlined for Intermediate 19, starting from 5'-chloro-2H,5H-spiro[imidazolidine-4,3'-indole]-2,2',5(1'H)-trione (intermediate 18) and 4-(bromomethyl)-5-methyl-3-phenylisoxazole, the title compound was isolated, after purification by chromatography (silica) eluting with cyclohexane containing increasing amounts of ethyl acetate (20 to 50%), as a white solid in 27% yield. MS (ESI⁺): 423.2; MS (ESI⁻): 423.1

Intermediate 22: tert-butyl [5'-chloro-1-[(5-methyl-3-phenylisoxazol-4-yl)methyl]-2,2',5-trioxospiro[imidazolidine-4,3'-indol]-1'(2'H)-yl]acetate, (cf. Schemes 7a and 7b, compound XI)

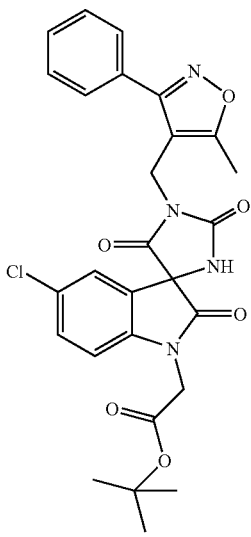

Following the general method as outlined for Intermediate 20 (method A), starting from 5'-chloro-1-[(5-methyl-3-phenylisoxazol-4-yl)methyl]-2H,5H-spiro[imidazolidine-4,3'-indole]-2,2',5(1'H)-trione (intermediate 21) and tert-Butyl bromoacetate, the title compound was isolated, after purification by chromatography (silica) eluting with cyclohexane containing increasing amounts of ethyl acetate (10 to 30%), as a white solid in 37% yield (HPLC purity 91%). MS (ESI$^+$): 537.3; MS (ESI$^-$): 535.6

Intermediate 23: (1-benzyl-5'-chloro)-2H,5H-spiro[imidazolidine-4,3'-indole]-2,2',5(1'H)-trione, (cf. Scheme7a, compound X)

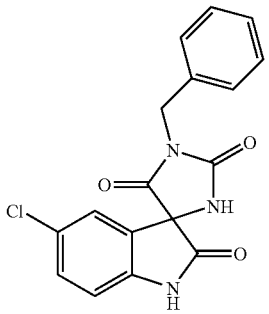

Following the general method as outlined for Intermediate 19, starting from 5'-chloro-2H,5H-spiro[imidazolidine-4,3'-indole]-2,2',5(1'H)-trione (intermediate 18) and benzyl bromide, the title compound was isolated, after trituration with diethyl ether, as a beige solid in 45% yield. MS (ESI$^-$): 340

Intermediate 24: tert-butyl[1-benzyl-5'-chloro)-2,2',5-trioxospiro[imidazolidine-4,3'-indol]-1'(2'H)-yl] acetate, (cf. Schemes 7a and 7b, compound XI)

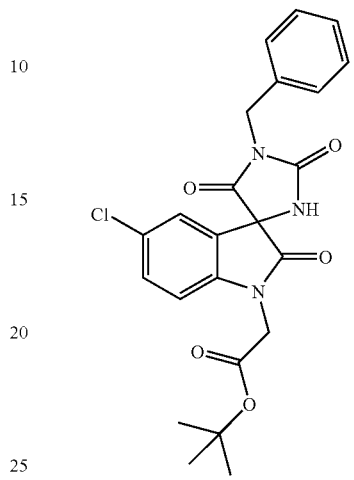

Following the general method as outlined for Intermediate 20 (method A), starting from (1-benzyl-5'-chloro)-2H,5H-spiro[imidazolidine-4,3'-indole]-2,2',5(1'H)-trione (intermediate 23) and tert-Butyl bromoacetate, the title compound was isolated, after purification by chromatography (silica) eluting with a 1:1 mixture of petroleum ether and ethyl acetate, as a colourless oil in 38% yield. MS (ESI$^-$): 454

Intermediate 25: 5'-chloro-1-(2-fluorobenzyl)-2H,5H-spiro[imidazolidine-4,3'-indole]-2,2',5(1'H)-trione, (cf. Scheme7a, compound X)

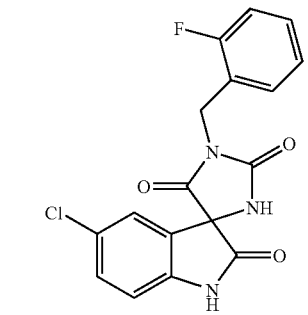

Following the general method as outlined for Intermediate 19, starting from 5'-chloro-2H,5H-spiro[imidazolidine-4,3'-indole]-2,2',5(1'H)-trione (intermediate 18) and 2-fluorobenzyl bromide, the title compound was isolated, after purification by chromatography (silica) eluting with petroleum ether containing increasing amounts of ethyl acetate (50 to 65%), as a white solid in 41% yield. MS (ESI$^-$): 358

Intermediate 26: tert-butyl [5'-chloro-1-(2-fluorobenzyl)-2,2',5-trioxospiro[imidazolidine-4,3'-indol]-1'(2'H)-yl]acetate, (cf. Schemes 7a and 7b, compound XI)

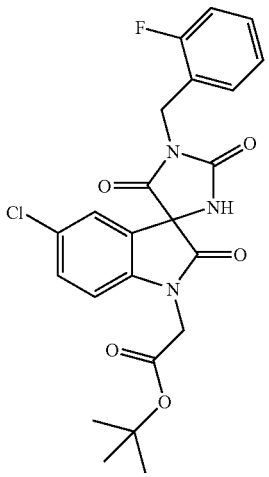

Following the general method as outlined for Intermediate 20 (method A), starting from (1-benzyl-5'-chloro)-2H,5H-spiro[imidazolidine-4,3'-indole]-2,2',5(1'H)-trione (intermediate 25) and tert-butyl bromoacetate, the title compound was isolated, after purification by chromatography (silica) eluting with petroleum ether containing increasing amounts of ethyl acetate (20 to 50%), as a white solid in 52% yield. MS (ESI$^-$): 454

Intermediate 27: methyl [5-chloro-3-(nitromethyl)-2-oxo-2,3-dihydro-1H-indol-3-yl](cyano)acetate, (cf. Scheme 8, compound XII)

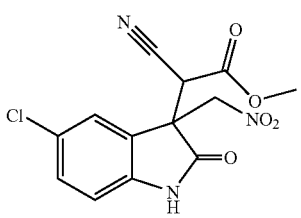

A suspension of methyl (2Z)-(5-chloro-2-oxo-1,2-dihydro-3H-indol-3-ylidene)(cyano)acetate, intermediate 1 (10.000 g; 38.1 mmol) in dry nitromethane (61 ml; 1.14 mol) was treated with piperidine (189 μl; 1.90 mmol). After stirring for 3 hours, the mixture was diluted with ethyl acetate and filtered through silica. Evaporation of the solvent gave methyl [5-chloro-3-(nitromethyl)-2-oxo-2,3-dihydro-1H-indol-3-yl](cyano)acetate as an oil (9.1 g, 73.8%). This was a mixture of diastereomers which was sufficiently pure for subsequent reaction (HPLC purity 97%). MS (ESI$^+$): 324.2; MS (ESI$^-$): 322.2

Intermediate 28: [5-chloro-3-(nitromethyl)-2-oxo-2,3-dihydro-1H-indol-3-yl](cyano)acetic acid, (cf. Scheme 8, compound XIII)

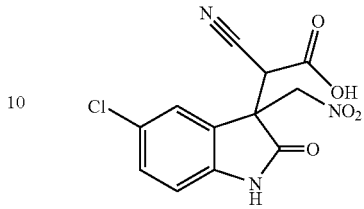

To a solution of methyl [5-chloro-3-(nitromethyl)-2-oxo-2,3-dihydro-1H-indol-3-yl](cyano)acetate, intermediate 27 (5.00 g; 15.45 mmol) in MeOH (150 ml) was added a potassium hydroxide solution in water (9.27 ml; 5.00 M; 46.34 mmol). After stirring for 2.5 l the solvent was evaporated. The residue was taken up with ethyl acetate and the organic phase extracted with 1N HCl, dried (MgSO$_4$) and the solvent removed in vacuo to give the crude [5-chloro-3-(nitromethyl)-2-oxo-2,3-dihydro-1H-indol-3-yl](cyano)acetic acid (4.89 g, quant.). This was a mixture of diastereomers, which was sufficiently pure for subsequent reaction (HPLC purity 93%).

Intermediate 29: [5-chloro-3-(nitromethyl)-2-oxo-2,3-dihydro-1H-indol-3-yl]acetonitrile (cf. Scheme 8, compound XIV)

A solution of [5-chloro-3-(nitromethyl)-2-oxo-2,3-dihydro-1H-indol-3-yl](cyano)acetic acid, intermediate 28 (2.00 g; 6.46 mmol) in anhydrous DMF (15 ml) was heated at 160° C. for 1 hour. After evaporation of the solvent, the residue was taken up in ethyl acetate, extracted with brine, dried (MgSO$_4$) and the solvent removed in vacuo to give the crude [5-chloro-3-(nitromethyl)-2-oxo-2,3-dihydro-1H-indol-3-yl]acetonitrile (1.74 g, quant, HPLC purity 93%). MS (ESI$^-$): 264.1

Intermediate 30: 245-chloro-3-(nitromethyl)-2-oxo-2,3-dihydro-1H-indol-3-yl]acetamide, (cf. Scheme 8, compound XV)

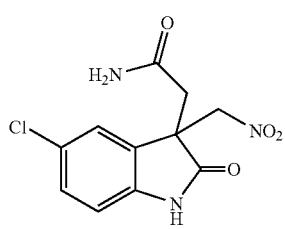

A solution of [5-chloro-3-(nitromethyl)-2-oxo-2,3-dihydro-1H-indol-3-yl]acetonitrile, intermediate 29 (775 mg; 2.92 mmol) in THF (6 ml) and water (2 ml) was treated with acetamide (775 mg; 13.13 mmol) and palladium(II) chloride (51.7 mg; 0.29 mmol) and stirred overnight. Ethyl acetate was added and the organic phase washed with brine, dried (MgSO4) and concentrated in vacuo to give the title compound (740 mg) which was used as such for the next step (HPLC purity 93%). MS (ESI$^+$): 284.1; MS (ESI$^-$): 282.1

Intermediate 31: 5-chloro-5'H-spiro[indole-3,3'-pyrrolidine]-2,5'(1H)-dione, (cf. Scheme 8, compound XVI)

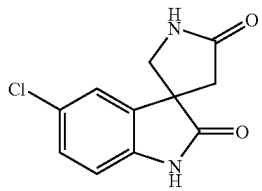

To an ice-cold suspension of 2-[5-chloro-3-(nitromethyl)-2-oxo-2,3-dihydro-1H-indol-3-yl]acetamide, intermediate 30 (1.10 g; 3.88 mmol) in AcOH (25 ml) zinc (2.5 g; 39 mmol) was added in portions over 5 minutes [CAUTION: EXOTHERMIC REACTION]. After 5 minutes stirring the ice bath was removed and the reaction mixture was stirred for 1 hour at room temperature. The reaction mixture was heated up to reflux for 2 h. The solvent was removed in vacuo, the residue was purified by Flash Chromatography (silica) using DCM containing increasing amounts of MeOH (3% to 20%) to give the title compound (420 mg, 45.8%) which was used as such for the next step (HPLC purity 77%). MS (ESI$^+$): 237.1; MS (ESI$^-$): 235.1

Intermediate 32: tert-butyl (5-chloro-2,5'-dioxospiro[indole-3,3'-pyrrolidin]-1(2H)-yl)acetate, (cf. Scheme 8, compound XVII)

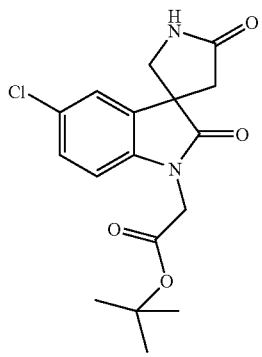

To a solution of 5-chloro-5'H-spiro[indole-3,3'-pyrrolidine]-2,5'(1H)-dione, intermediate 31 (230 mg; 0.97 mmol) in dry DMF (10 ml) was added potassium tert-butoxide (109 mg; 0.97 mmol). The reaction mixture was stirred at RT for 30 min, then cooled to 0° C. and tert-butyl bromoacetate (190 mg; 0.97 mmol) was added dissolved in 3 mL of dry DMF. The reaction mixture was stirred for 1 hour at room temperature. The solvent was evaporated in vacuo and the residue redissolved in ethyl acetate (20 mL), washed with water, dried (MgSO$_4$) and the solvent removed in vacuo. The residue was purified by Flash Chromatography (silica) using cyclohexane containing increasing amounts of ethyl acetate (50% to 100%) to give the title compound (341 mg, 52.4%, HPLC purity 100%). MS (ESI$^+$): 351.1; MS (ESI$^-$): 349.2

Intermediate 33: tert-butyl [1'-benzyl-5-chloro-2,5'-dioxospiro[indole-3,3'-pyrrolidin]-1(2H)-yl]acetate, (cf. Scheme 8, compound XVIII)

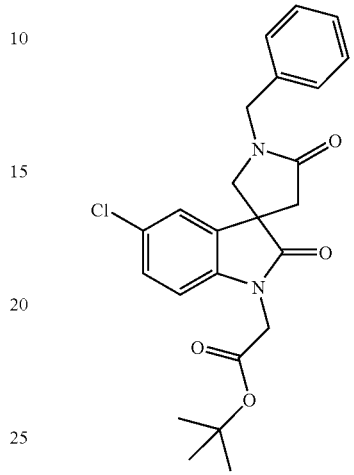

To a solution of tert-butyl (5-chloro-2,5'-dioxospiro[indole-3,3'-pyrrolidin]-1(2H)-yl)acetate, intermediate 32 (175.00 mg; 0.50 mmol) in dry THF (5 mL), sodium hydride (24 mg; 0.60 mmol) was added. The reaction mixture was stirred 15 minutes then benzyl bromide (71.10 µl; 0.60 mmol) was added. After stirring for 10 min, the solvent was evaporated and the residue redissolved in ethyl acetate, washed with water and brine, dried (MgSO$_4$), and removed in vacuo to give a residue which was purified by chromatography (silica) eluting with cyclohexane containing increasing amounts of ethyl acetate (20 to 50%) to give the title compound was obtained (220 g, 52.1%, HPLC purity 96.7%). MS (ESI$^+$): 441.4; MS (ESI$^-$): 439.2

Intermediate 34: tert-butyl [5-chloro-1'-(5-chloro-2-fluorobenzyl)-2,5'-dioxospiro[indole-3,3'-pyrrolidin]-1(2H)-yl]acetate, (cf. Scheme 8, compound XVIII)

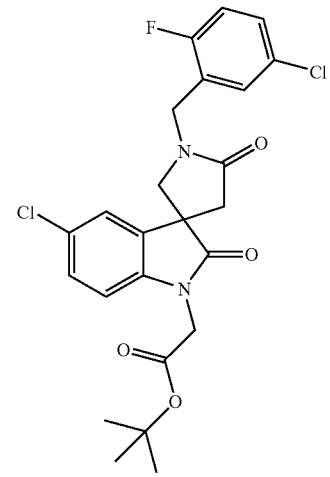

Following the general method as outlined for Intermediate 33, starting from tert-butyl [5-chloro-1'-(2-fluorobenzyl)-2,5'-dioxospiro[indole-3,3'-pyrrolidin]-1(2H)-yl]acetate (intermediate 32) and 5-chloro-2-fluorobenzyl bromide, the title compound was isolated, after purification by chromatography (silica) eluting with cyclohexane containing increasing amounts of ethyl acetate (5 to 40%), as a white solid in 72.7% yield (HPLC purity 94%). MS (ESI$^+$): 493.4; MS (ESI$^-$): 491.0

Intermediate 35: tert-butyl [5-chloro-1'-[(3-methyl-5-phenylisoxazol-4-yl)methyl]-2,5'-dioxospiro[indole-3,3'-pyrrolidin]-1(2H)-yl]acetate, (cf. Scheme 8, compound XVIII)

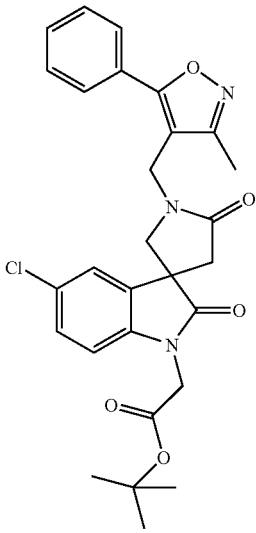

Following the general method as outlined for Intermediate 33, starting from tert-butyl (5-chloro-2,5'-dioxospiro[indole-3,3'-pyrrolidin]-1(2H)-yl)acetate (intermediate 32) and 4-(bromomethyl)-3-methyl-5-phenylisoxazole, the title compound was isolated, after purification by chromatography (silica) eluting with cyclohexane containing increasing amounts of ethyl acetate (10 to 50%), as a white solid in 53% yield (HPLC purity 89%). MS (ESI$^+$): 522.4; MS (ESI$^-$): 520.1

Intermediate 36: tert-butyl [5-chloro-F-(2-fluorobenzyl)-2,5'-dioxospiro[indole-3,3'-pyrrolidin]-1(2H)-yl]acetate,(cf. Scheme 8, compound XVIII)

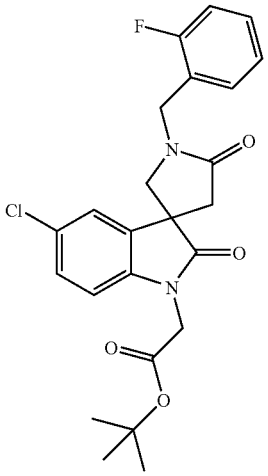

Following the general method as outlined for Intermediate 33, starting from tert-butyl [5-chloro-1'-(2-fluorobenzyl)-2,5'-dioxospiro[indole-3,3'-pyrrolidin]-1(2H)-yl]acetate (intermediate 32) and 2-fluorobenzyl bromide, the title compound was isolated, after purification by chromatography (silica) eluting with cyclohexane containing increasing amounts of ethyl acetate (20 to 50%), as a white solid in 54% yield (HPLC purity 90%). MS (ESI$^+$): 459.3; MS (ESI$^-$): 457.2

Intermediate 37: benzyl 2-{[(benzyloxy)carbonyl]oxy}-5-chloro-1H-indole-1-carboxylate (cf. Scheme 9, compound XX)

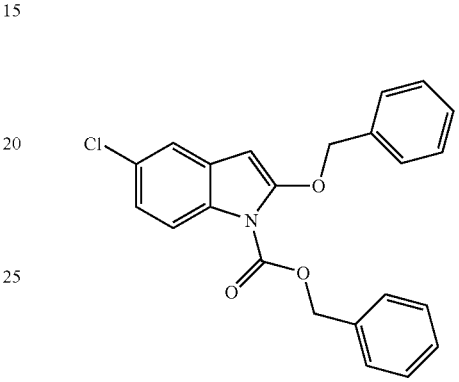

To an ice-cold solution of 5-chlorooxindole (16.75 g; 100 mmol) and triethylamine (30.50 ml; 220 mmol) in THF (360 ml) was added dropwise benzyl chloroformate (37.9 ml; 240 mmol). After stirring at room temperature for 6 h, water was added and the organic phase was separated, washed again with brine, dried (MgSO$_4$) and removed in vacuo to give a solid residue which was purified by recrystallisation (ethyl acetate), to give the title compound in 61% yield (HPLC purity 89%).

Intermediate 38: benzyl 5-chloro-2-oxoindoline-1-carboxylate, (cf. Scheme 9, compound XXI)

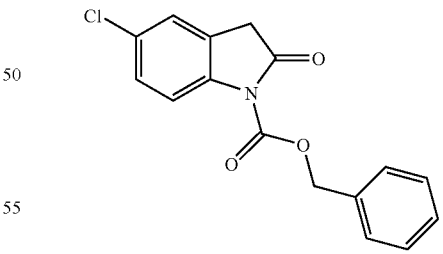

Benzyl 2-{[(benzyloxy)carbonyl]oxy}-5-chloro-1H-indole-1-carboxylate, intermediate 37 (5.00 g; 11.47 mmol) was treated with a solution of ammonia in dioxane (25.2 ml; 0.50 M; 12.6 mmol) and stirred overnight. Brine was added and the mixture extracted with ethyl acetate. The organic phase was dried (MgSO$_4$) and removed in vacuo, to give a solid residue which was purified by recrystallisation (ethyl acetate), to give the title compound in 59% yield (HPLC purity 88%). MS (ESI$^+$): 302.1; MS (ESI$^-$): 300.1

Intermediate 39: benzyl 5-chloro-2,2'-dioxospiro[indole-3,3'-pyrrolidine]-1(2H)-carboxylate, (cf. Scheme 9, compound XXII)

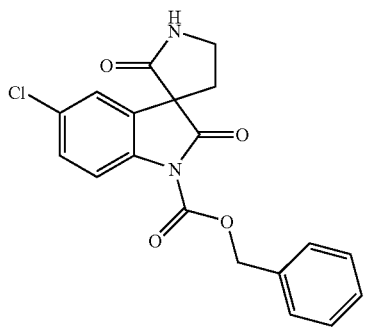

A solution of benzyl 5-chloro-2-oxoindoline-1-carboxylate, intermediate 38 (2.00 g; 6.63 mmol) in dry DMF (30.00 ml) was treated with sodium hydride pract. (265.12 mg; 6.63 mmol). After 10 min, 2-bromoethyl isocyanate (599 µl; 6.63 mmol) was added. After a further 10 minutes, ethyl acetate was added and washed with water. The organic phase was dried (MgSO$_4$) and the solvent removed in vacuo, to give a solid residue which was purified by recrystallisation (ethyl acetate), to give the title compound in 57% yield (HPLC purity 92%). MS (ESI$^+$): 371.1; MS (ESI$^-$): 369.1

Intermediate 40: 5-chloro-2'H-spiro[indole-3,3'-pyrrolidine]-2,2'(1H)-dione, (cf. Scheme 9, compound XXIII)

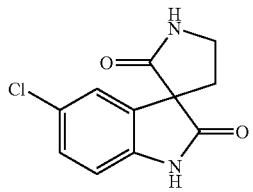

A solution of benzyl 5-chloro-2,2'-dioxospiro[indole-3,3'-pyrrolidine]-1(2H)-carboxylate, intermediate 39 (1.000 g; 2.70 mmol) in DMF (50 ml) was treated with platinum oxide (200 mg; 0.88 mmol). The mixture was placed in a hydrogenation vessel under 20 atm of hydrogen. After stirring overnight, a further quantity of platinum dioxide (2.50 g) was added and hydrogenation continued at 20 atm H$_2$ overnight. The reaction mixture was filtered on a paper filter, then the solvent was removed in vacuo to give the title compound in 96% yield (HPLC purity 85%). MS (ESI$^+$): 237.0; MS (ESI$^-$): 235.0

Intermediate 41: tert-butyl (5-chloro-2,2'-dioxospiro[indole-3,3'-pyrrolidin]-1(2H)-yl)acetate, (cf. Scheme 9, compound XXIV)

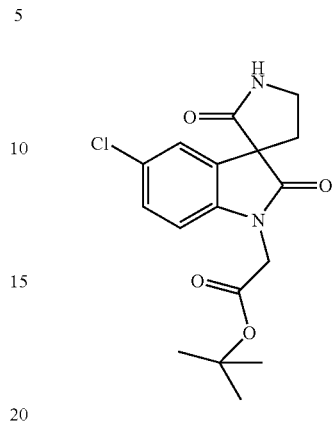

A solution of 5-chloro-5'H-spiro[indole-3,3'-pyrrolidine]-2,5'(1H)-dione, intermediate 40 (600.00 mg; 2.16 mmol) in 30 mL of dry DMF was treated with potassium tert-butoxide (241.82 mg; 2.16 mmol; 1.00 eq.). After 10 min, the reaction mixture was treated with a solution of tert-butyl bromoacetate (420.35 mg; 2.16 mmol) in 6 mL of dry DMF. After 4 h, the solvent was evaporated and the residue dissolved in ethyl acetate. After addition of water, a solid precipitated and was filtered to give the title compound as a grey solid in 30% yield (HPLC purity 89%) MS (ESI$^+$): 351.2; MS (ESI$^-$): 348.9

Intermediate 42: tert-butyl [5-chloro-1'-[(5-methyl-3-phenylisoxazol-4-yl)methyl]-2,2'-dioxospiro[indole-3,3'-pyrrolidin]-1(2H)-yl]acetate, (cf. Scheme 9, compound XXV)

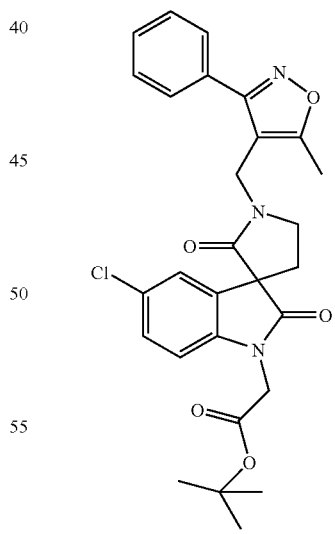

A suspension of tert-butyl (5-chloro-2,5'-dioxospiro[indole-3,3'-pyrrolidin]-1(2H)-yl)acetate, intermediate 41 (100 mg; 0.29 mmol) in dry DMF (5 ml) was treated with sodium hydride pract. (14.8 mg; 0.37 mmol). After stirring for 20 minutes 4-(bromomethyl)-5-methyl-3-phenylisoxazole (86.24 mg; 0.34 mmol) was added. After stirring for 1 h the solvent was evaporated to give a residue, which was dissolved in ethyl acetate. The organic phase was washed with brine, dried (MgSO$_4$) and removed in vacuo, to give a solid residue which was purified by chromatography (silica), eluting with cyclohexane containing increasing amounts of ethyl acetate (30 to 50%), to give the title compound in 58% yield (HPLC purity 99%). MS (ESI$^+$): 522.4; MS (ESI$^-$): 520.2

Intermediate 43: Methyl (5-chloro-2,3-dioxo-2,3-dihydro-1H-indol-1-yl)acetate (cf. Scheme 1b, compound VIIIb)

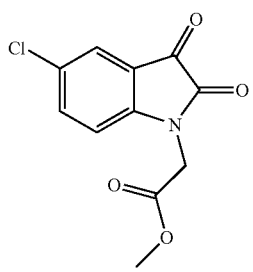

To a solution of 5-chloroisatin, compound VIII, (10.0 g, 55.07 mmol) in anhydrous N,N-dimethylformamide (100 ml) potassium carbonate (9.87 g, 71.59 mmol) was added portionwise at 0-5° C. After stirring at 0-5° C. for further 10 minutes and at ambient temperature for one additional hour methyl bromoacetate (8.25 ml, 60.58 mmol) was added dropwise at such a rate that the internal temperature did not exceed 35° C. The resulting orange suspension was allowed to stir at ambient temperature overnight. Water was added (350 ml) and the product was extracted with ethyl acetate (5×100 ml). The combined organic extracts were washed with brine (100 ml), dried (MgSO$_4$) and evaporated under reduced pressure to give the title compound (10.83 g, 76%) as orange solid (HPLC purity 98%). MS (ESI$^+$): 254.1; MS (ESI$^-$): 252.1

Intermediate 44: tert-Butyl (5-chloro-2,3-dioxo-2,3-dihydro-1H-indol-1-yl)acetate (cf. Scheme 7b, compound VIIIb)

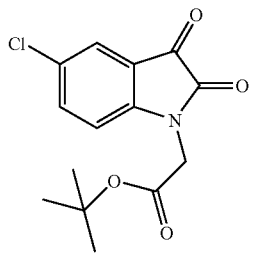

According to the general procedure as outlined above for the synthesis of intermediate 43, f 5-chloroisatin, compound VIII, (10.0 g, 55.07 mmol) was reacted with potassium carbonate (9.89 g, 5.03 mmol) and tert-butyl bromoacetate (8.95 ml, 60.58 mmol) in N,N-dimethylformamide (100 ml) to give the title compound (12.14 g, 75%) as orange solid (HPLC purity: 99%) after precipitation from water. MS (ESI$^-$): 294.2

Intermediate 45: Methyl (2Z)-[5-chloro-1-(2-methoxy-2-oxoethyl)-2-oxo-1,2-dihydro-3H-indol-3-ylidene](cyano)acetate, (cf. Scheme 1b, compound VIIb)

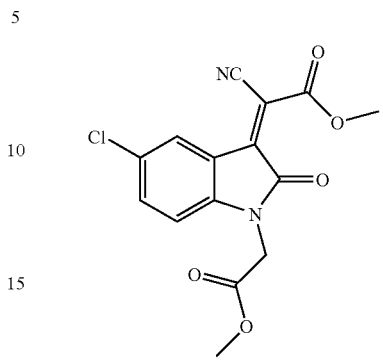

To a suspension of methyl (5-chloro-2,3-dioxo-2,3-dihydro-1H-indol-1-yl)acetate, intermediate 43, (10.17 g, 40.10 mmol) in methanol (200 ml) methyl cyanoacetate (3.55 ml, 40.10 mmol) and piperidine (0.40 ml, 4.01 mmol) were added at ambient temperature. The resulting fine suspension was continuously stirred at ambient temperature overnight. The precipitate was filtered off, washed with methanol (3×20 ml) and dried in vacuo to yield the title compound (11.62 g, 80%) as purple solid (HPLC purity: 92%). MS (ESI$^+$): 335.2; MS (ESI$^-$): 333.2

Intermediate 46: Methyl [5-chloro-3-cyano-1-(2-methoxy-2-oxoethyl)-2-oxo-2,3-dihydro-1H-indol-3-yl](cyano)acetate, (cf. Scheme 1b, compound VIb)

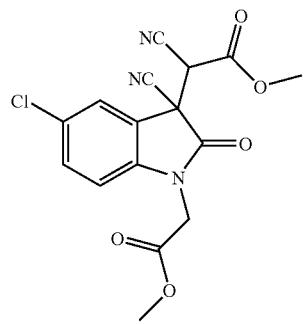

A solution of potassium carbonate (1.39 g, 10.03 mmol) in water (8.2 ml) was treated with acetone cyanohydrine (4.0 ml, 43.5 mmol) at ambient temperature and continuously stirred for 15 min. A fine suspension of methyl (2Z)-[5-chloro-1-(2-methoxy-2-oxoethyl)-2-oxo-1,2-dihydro-3H-indol-3-ylidene](cyano)acetate, intermediate 45, (11.19 g, 33.43 mmol) in tetrahydrofuran (500 ml) was added dropwise and the resulting suspension was heated to reflux for 3 hours. The solid was filtered off, the residue was washed with tetrahydrofuran (3×40 ml) and the collected filtrates were evaporated to dryness. The solid was dissolved in dichloromethane (250 ml), washed with saturated NaHCO$_3$ (2×100 ml), water (100 ml) and dried (MgSO$_4$) to obtain the title compound (10.82 g, 89%) as red-brown solid (HPLC purity: 91%). MS (ESI$^+$): 362.2; MS (ESI$^-$): 360.2

Intermediate 47: Methyl (5-chloro-2,2',5'-trioxospiro[indole-3,3'-pyrrolidin]-1(2H)-yl)acetate (cf. Schemes 1a, 1b, 3, compound of general structure IV)

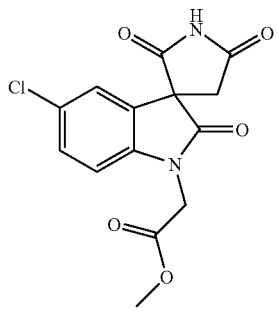

A suspension of methyl [5-chloro-3-cyano-1-(2-methoxy-2-oxoethyl)-2-oxo-2,3-dihydro-1H-indol-3-yl](cyano)acetate, intermediate 46, (10.56 g, 29.19 mmol) in dry methanol (190 ml) was purged with hydrogen chloride at −78° C. for 45 minutes. The suspension was allowed to warm up to ambient temperature and further heated up to reflux for 4 hours. The solvent was removed in vacuo, the remaining solid was suspended in glacial acetic acid (300 ml) and heated up to reflux for 5 hours. Evaporation under reduced pressure gave a red-brown oil, which was redissolved in ethyl acetate (300 ml). The solution was washed with water (2×200 ml), the aqueous washes were once back-extrated with ethyl acetate (200 ml) and the organic extracts were dried (MgSO$_4$) to give the title compound (10.87 g, quant.) as solidified foam (HPLC purity: 91%). MS (ESI$^+$): 323.2; MS (ESI$^-$): 321.1

Intermediate 48: Methyl [5-chloro-1'-(3-chlorobenzyl)-2,2',5'-trioxospiro[indole-3,3'-pyrrolidin]-1(2H)-yl)acetate, (cf. Schemes 1a, 1b, 1c, 3, 4, compound of general structure II)

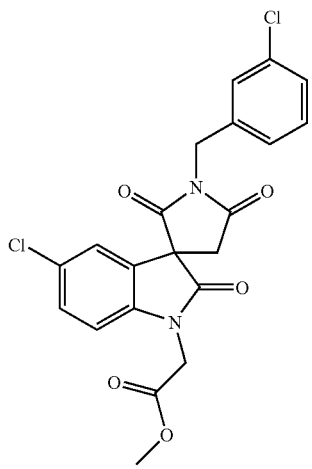

Following the general procedure (Route A) as outlined above for the synthesis of intermediate 16, methyl (5-chloro-2,2',5'-trioxospiro[indole-3,3'-pyrrolidin]-1(2H)-yl)acetate, intermediate 47, (2.94 g, 9.11 mmol) was reacted with potassium tert-butoxide (1.07 g, 9.57 mmol) and 3-chlorobenzyl bromide (1.25 ml, 9.57 mmol) in anhydrous N,N-dimethylformamide (90 ml) at ambient temperature for two hours to give the title compound (2.10 g, 52%) as slightly pink powder after trituration from tetrahydrofuran/diethyl ether. The compound was isolated in several fractions (HPLC purity: 96-99%). MS (ESI$^+$): 447.3; MS (ESI$^-$): 445.3

Intermediate 49: Ethyl-5-chloro-2-[(ethoxycarbonyl)oxy]-1H-indole-1-carboxylate (cf. Schemes 1c, 9, compound XX)

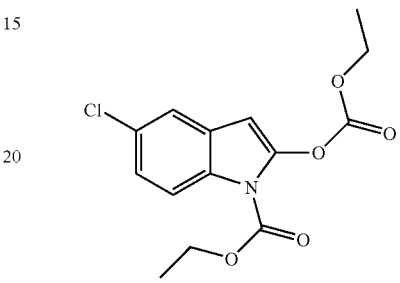

Following the general procedure as outlined above for the synthesis of intermediate 37, 5-chlorooxindole, compound VIII, (20.0 g, 119.34) was treated with triethylamine (36.4 ml, 262.54 mmol) and ethyl chloroformate (25.2 ml, 262, 54 mmol) for 90 min to give the title compound (36.87 g, 99%) as slightly pink crystalline solid after aqueous work-up (HPLC purity: 97%). MS (ESI$^-$): 310.1

Intermediate 50: Diethyl-5-chloro-2-oxoindoline-1,3-dicarboxylate, (cf. Scheme 1c, compound XXVI)

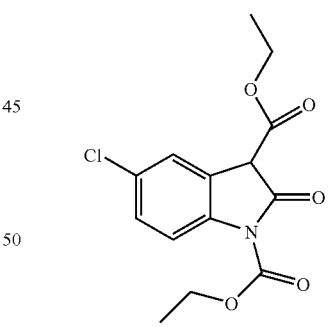

To a solution of ethyl-5-chloro-2-[(ethoxycarbonyl)oxy]-1H-indole-1-carboxylate, intermediate 49, (36.87 g, 118.28 mmol) in N,N-dimethylformamide (100 ml) 4-dimethylaminopyridine (14.45 g, 118.28 mmol) was added portionwise at 0-5° C. such that the internal temperature did not exceed 5° C. A thick suspension was obtained, which was repeatedly diluted with N,N-dimethylformamide (total volume: 350 ml) to ease up stirring. After two hours at 0-5° C. a solution of hydrogen chloride (fuming, 37%; 9.8 ml) in water (480 ml) was added at such a rate that the internal temperature could be kept below 15° C. The precipitate was filtered, washed with water at 0-5° C. (2×100 ml) and dried to yield the title com-

Intermediate 51: Diethyl-3-(2-tert-butoxy-2-oxoethyl)-5-chloro-2-oxoindoline-1,3-dicarboxylate, (cf. Scheme 1c, compound XXVII)

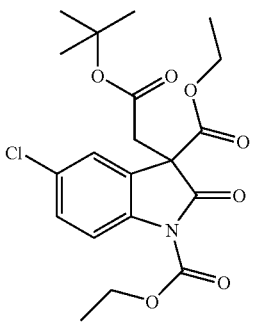

To a solution of diethyl-5-chloro-2-oxoindoline-1,3-dicarboxylate, intermediate 50, (5.0 g, 16.04 mmol) in anhydrous N,N-dimethylformamide (80 ml) 1,8-diazabicyclo[5.4.0]undec-7-ene (2.63 ml, 17.64 mmol) was added dropwise at ambient temperature at such a rate that the internal temperature remained below 30° C. After continuous stirring at ambient temperature for one hour the solution was treated with tert-butyl bromoacetate (2.73 ml, 18.45 mmol) and stirring was allowed to continue for 72 h. Water (100 ml) was added, the product was extracted with tert-butyl methyl ether (2×50 ml), the combined extracts were washed with brine (50 ml) and dried (MgSO$_4$) to give a red solid (7.11 g). Purification by flash chromatography (n-heptane/ethyl acetate=15%; increased up to 20%) yielded the title compound (4.00 g, 59%) as colorless solid (HPLC purity: 99%).MS (ESI$^+$): 426.3

Intermediate 52: [5-Chloro-1,3-bis(ethoxycarbonyl)-2-oxo-2,3-dihydro-1H-indol-3-yl]acetic acid, (cf. Scheme 1c, compound XXVIII)

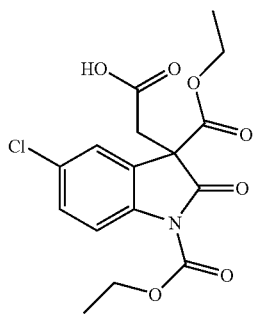

To a solution of diethyl-3-(2-tert-butoxy-2-oxoethyl)-5-chloro-2-oxoindoline-1,3-dicarboxylate, intermediate 51, (1.83 g, 4.30 mmol) in dichloromethane (30 ml) trifluoroacetic acid (3.18 ml, 42.97 mmol) was added at 0-5° C. Stirring was continued at 0-5° C. for 30 minutes and at ambient temperature overnight. Evaporation and drying under high vacuum gave the title compound (1.57 g, 99%) as colorless oil (HPLC purity: 85%). MS (ESI$^+$): 370.2

Intermediate 53: 5-Chloro-1'(2-fluorobenzyl)-2'H, 5'H-spiro[indole-3,3'-pyrrolidine]-2,2',5'(1H)-trione, (cf. Schemes 1a, 1c, 4, 5, compound III)

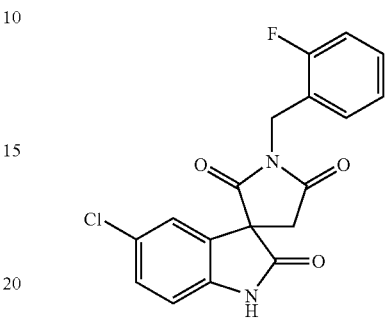

To a solution of [5-chloro-1,3-bis(ethoxycarbonyl)-2-oxo-2,3-dihydro-1H-indol-3-yl]acetic acid, intermediate 52, (1.55 g, 4.1.9 mmol) in tetrahydrofuran (20 ml) 1,1'-carbonyldiimidazole (820 mg, 5.03 mmol) was added at 0-5° C. Stirring was continued at 0-5° C. for 10 minutes and at ambient temperature 3 hours. The solution was treated with 2-fluorobenzylamine (0.57 ml, 5.03 mmol) and continuously stirred at ambient temperature for 24 hours. The solution was heated up to reflux for additional 24 hours prior to the addition of water (25 ml). The product was extracted with tert-butyl methyl ether (3×15 ml) and the collected extracts were dried (MgSO$_4$) to give red-brown solid (1.92 g). Recrystallization from toluene (25 ml) provided the title compound (810 mg, 54%) as off-white solid (HPLC purity 96%). MS (ESI$^+$): 359.0; MS (ESI$^-$): 357.0

Intermediate 54: tert-Butyl (5'-chloro-2,2'5'-trioxospiro[imidazolidine-4,3'-indol]-1'(2'H)-yl)acetate, (cf. Scheme 7b, compound IXb)

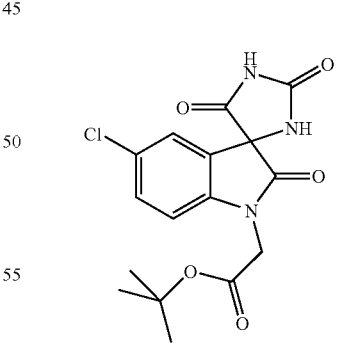

According to the general method outlined above for the synthesis of intermediate 18 tert-butyl (5-chloro-2,3-dioxo-2,3-dihydro-1H-indol-1-yl)acetate, intermediate 44, (8.17 g, 27.64 mmol) was reacted with potassium cyanide (2.39 g, 36.76 mmol) and ammonium carbonate (21.24 g, 221.0 mmol) in ethanol/water=2:1 (300 ml) for 90 minutes to give the title compound (7.38 g, 73%) as dark purple solid (HPLC purity: 63%). MS (ESI$^-$): 364.3

Example 1

[5-chloro-1'-[(2-methyl-1,3-thiazol-4-yl)methyl]-2,2',5'-trioxospiro[indole-3,3'-pyrrolidin]-1(2H)-yl]acetic acid

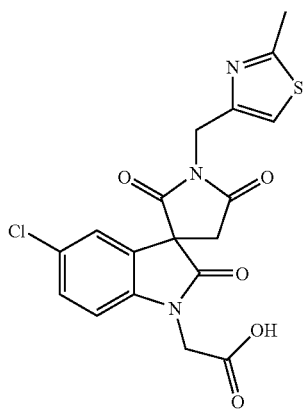

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 60% yield (96% purity by HPLC). MS (ESI$^+$): 420.8; MS (ESI$^-$): 418.7.

Example 2

[5-chloro-1'-(2,4-dichlorobenzyl)-2,2',5'-trioxospiro[indole-3,3'-pyrrolidin]-1(2H)-yl]acetic acid

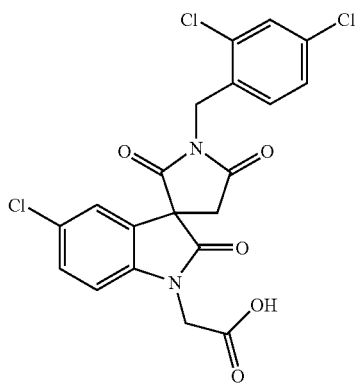

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 65% yield (90% purity by HPLC). MS (ESI$^+$): 468.8; MS (ESI$^-$): 466.7.

Example 3

[5-chloro-2,2',5'-trioxo-1'-(quinolin-2-ylmethyl)spiro[indole-3,3'-pyrrolidin]-1(2H)-yl]acetic acid

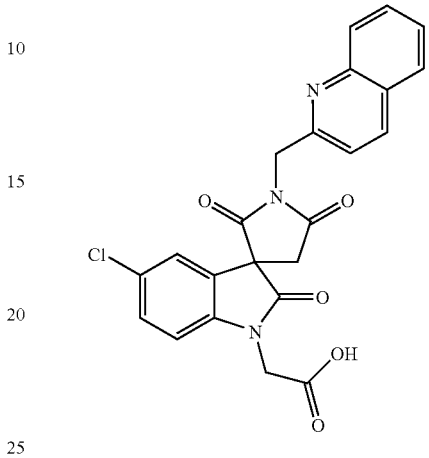

Following the general methods as outlined in Example 12 (Method D), starting from 5-Chloro-1H-spiro[indole-3,3'-pyrrolidine]-2,2',5'-trione (Intermediate 9), the title compound was isolated as a white-brown solid in 55% yield (79.5% purity by HPLC). MS (ESI$^+$): 450.9; MS (ESI$^-$): 448.8.

Example 4

[5-chloro-1'-(4-cyanobenzyl)-2,2',5'-trioxospiro[indole-3,3'-pyrrolidin]-1(2H)-yl]acetic acid

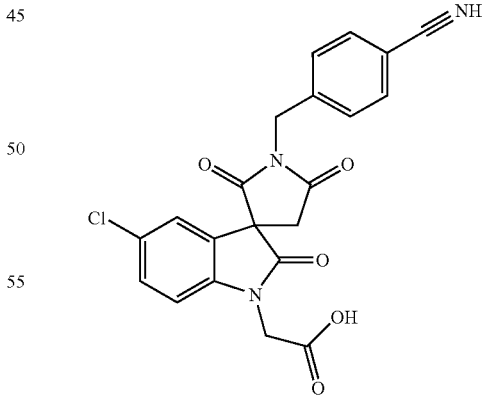

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 66% yield (82% purity by HPLC). MS (ESI$^+$): 424.9; MS (ESI$^-$): 422.8.

Example 5

[5-chloro-1'-(3-chlorobenzyl)-2,2',5'-trioxospiro[indole-3,3'-pyrrolidin]-1(2H)-yl]acetic acid

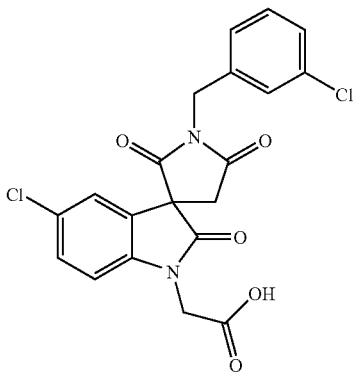

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 61% yield (91% purity by HPLC).

Alternatively, a solution of methyl [5-chloro-1'-(3-chlorobenzyl)-2,2',5'-trioxospiro[indole-3,3'-pyrrolidin]-1(2H)-yl)acetate, intermediate 48, (250 mg, 0.56 mmol) in chloroforme or acetonitrile (10 ml) was treated with iodotrimethylsilane (0.31 ml, 2.24 mmol) and heated up to reflux until completion. Addition of 1.0 N HCl (10 ml), product extraction with ethyl acetate or chloroforme (3×5 ml), washing of the combined extracts with sat. sodium thiosulfate (10 ml) and drying (MgSO$_4$) gave the title compound as in quant.yield as slightly yellow solid (75% purity by HPLC using chloroform; 68% purity by HPLC using acetonitrile). MS (ESI$^+$): 434.3; MS (ESI$^-$): 431.4.

Example 6

[5-chloro-1'-(3,4-dichlorobenzyl)-2,2',5'-trioxospiro[indole-3,3'-pyrrolidin]-1(2H)-yl]acetic acid

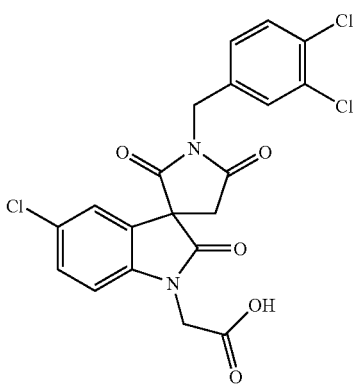

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 70% yield (94% purity by HPLC). MS (ESI$^+$): 468.7; MS (ESI$^-$): 465.6.

Example 7

[5-chloro-1'-(2-fluorobenzyl)-2,2',5'-trioxospiro[indole-3,3'-pyrrolidin]-1(2H)-yl]acetic acid

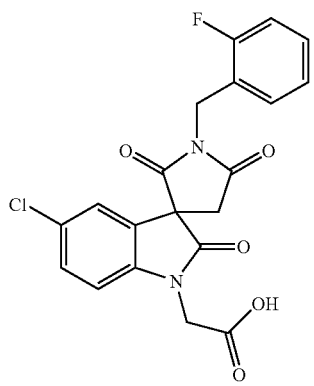

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 72% yield (85% purity by HPLC). MS (ESI$^+$): 417.7; MS (ESI$^-$): 415.6.

Example 8

[5-chloro-1'-(4-fluorobenzyl)-2,2',5'-trioxospiro[indole-3,3'-pyrrolidin]-1(2H)-yl]acetic acid

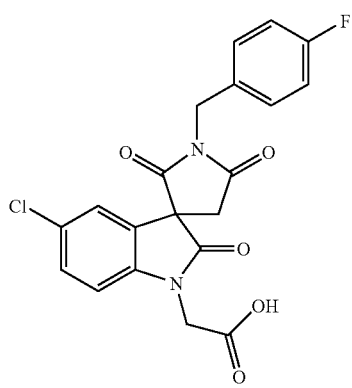

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 73% yield (92% purity by HPLC). MS (ESI$^+$): 417.8; MS (ESI$^-$): 415.6.

Example 9

[5-chloro-1'-(1-naphthylmethyl)-2,2',5'-trioxospiro[indole-3,3'-pyrrolidin]-1(2H)-yl]acetic acid

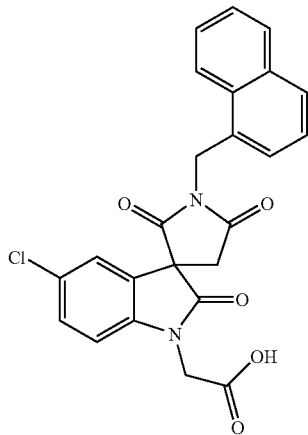

Following the general methods as outlined in Example 12 (Method D), starting from 5-Chloro-1H-spiro[indole-3,3'-pyrrolidine]-2,2',5'-trione (Intermediate 9), the title compound was isolated as a brown foam in 76% yield (93.4% purity by HPLC). MS (ESI$^+$): 449.8; MS (ESI$^-$): 447.6.

Example 10

[5-chloro-2,2',5'-trioxo-1'-(3-phenoxybenzyl)spiro[indole-3,3'-pyrrolidin]-1(2H)-yl]acetic acid

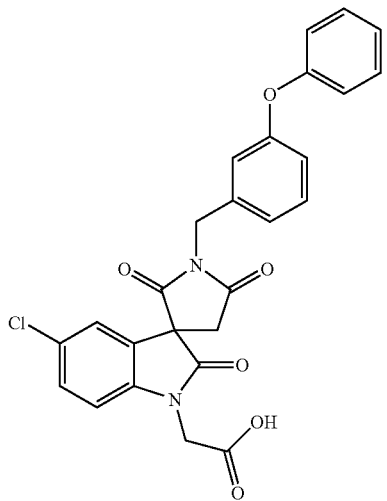

Following the general methods as outlined in Example 12 (Method D), starting from 5-Chloro-1H-spiro[indole-3,3'-pyrrolidine]-2,2',5'-trione (Intermediate 9), the title compound was isolated as a black solid in 72% yield (92% purity by HPLC). MS (ESI$^+$): 491.9; MS (ESI$^-$): 489.8.

Example 11

[5-chloro-1'-(3-fluorobenzyl)-2,2',5'-trioxospiro[indole-3,3'-pyrrolidin]-1(2H)-yl]acetic acid

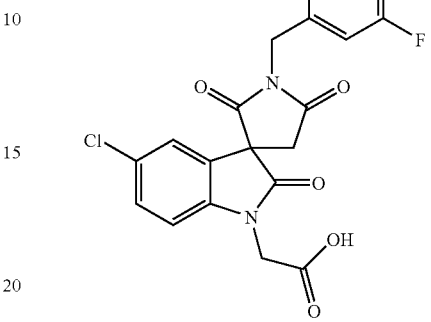

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 69% yield (91% purity by HPLC). MS (ESI$^+$): 417.8; MS (ESI$^-$): 415.6.

Example 12

General procedure for the synthesis of spiroindolinone derivatives of general formula Ia, with R$^1$, R$^2$ and R$^3$ as above defined (Schemes 1, 6): (1'-Benzyl-5-chloro-2,2',5'-trioxo-spiro[indole-3,3'-pyrrolidin]-1-yl)acetic acid

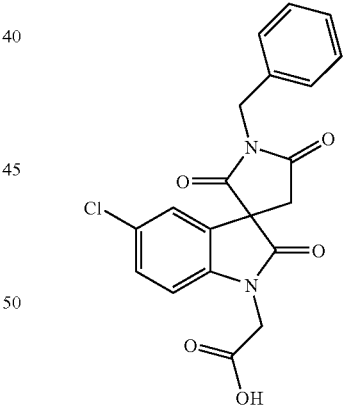

Method A:

A stirred solution of (1'-benzyl-5-chloro-2,2',5'-trioxo-spiro[indole-3,3'-pyrrolidin]-1-yl)-acetic acid tert-butyl ester, intermediate 16 (800 mg, 1.76 mmol) in anhydrous dichloromethane (20 ml) was cooled in an ice-water bath and treated with trifluoroacetic acid (1.0 ml). After stirring in the cold for 30 min the mixture was allowed to come to ambient temperature. After 2 hours, thin layer chromatography (silica; ethyl acetate/petroleum ether (40-60) [1:1]) showed little reaction, so more trifluoroacetic acid (1.0 ml) was added and the reaction mixture stirred at ambient temperature for 48 hours. The solvent was removed in vacuo and toluene (50 ml)

was added. The crude (1'-benzyl-5-chloro-2,2',5'-trioxo-spiro[indole-3,3'-pyrrolidin]-1-yl)acetic acid was removed by filtration and washed with more toluene (25 ml) followed by petroleum ether (40-60) (25 ml). Purification by flash chromatography (silica) eluting with ethyl acetate gave a white solid (401 mg, 57%), m.pt. 205-207° C.

$^1$H NMR (400 MHz, CDCl$_3$+DMSO(d6); Me4Si): 3.06 (d, 1H), 3.32 (d, 1H), 4.30 (d, 1H), 4.60 (d, 1H), 4.75 (s, 2H), 6.83 (d, 1H), 7.11 (d, 1H), 7.33 (m, 5H), 7.43 (s, 1H). MS (ESI+) 399.9, (ESI−) 397.8

Method B: (Route A, Parallel Method 1)

Stage 1: Each tube was charged with (5-Chloro-2,2',5'-trioxo-spiro[indole-3,3'-pyrrolidin]-1-yl)acetic acid tert-butyl ester, intermediate 13 (73 mg, 0.2 mmol), potassium carbonate (83 mg, 0.6 mmol) and anhydrous N,N-dimethylformamide (2 ml). The appropriate alkylating agent (0.24 mmol) was added and the reaction mixtures stirred at 50° C. overnight (except in the cases where it was considered that the alkylating agent might be less stable when the reactions were carried out at ambient temperature). When the alkylating agent was alpha-methyl benzyl bromide or analogues, the reaction was carried out in a CEM Discover Microwave reactor at 150° C. for 30 minutes. In the cases where the alkylating agent was in the form of the hydrochloride salt, twice the normal amount of potassium carbonate was used. Each of the reaction mixtures was worked up by adding water (about 5 ml) and extracting with ethyl acetate (3×5 ml (approx.)). The extracts were evaporated in tubes using a Genevac HT4 for 2 hours at 60° C. They were then taken on to the next stage.

Stage 2: Each of the crude products from Stage 1 were treated with a 10% (v/v) solution of trifluoroacetic acid in anhydrous dichloromethane (3 ml) and stirred at ambient temperature for 72 hours. Toluene (1 ml) was added to each reaction mixture, the magnetic stirrer beads removed and the solvents removed using a Genevac HT4, firstly under "vac ramp" conditions at 45° C. for 1 h50 and secondly at full vacuum at 50° C. for 45 min. N,N-dimethylformamide (1 ml) was added to each tube to dissolve the residues which were transferred to a microtitre plate for automated reverse phase preparative chromatography.

Method C: (Route B, Parallel Method 2)

Stage 1: Reaction vessels were charged with either 6-chloro-1H-spiro[indole-3,3'-pyrrolidine]-2,2',5'-trione, intermediate 12 (300 mg, 1.198 mmol), anhydrous N,N-dimethylformamide (2.5 ml) and potassium tert-butoxide (141 mg, 1.198 mmol) or 5-trifluoromethoxy-1H-spiro[indole-3,3'-pyrrolidine]-2,2',5'-trione, intermediate 11 (400 mg, 1.6 mmol), anhydrous N,N-dimethylformamide (2.5 ml) and potassium tert-butoxide (188 mg, 1.6 mmol). After stirring at ambient temperature for 40 minutes, the appropriate alkylating agent (1 eq) was added and the mixtures stirred at ambient temperature for 18 hours. If the alkylating agent was in the form of the hydrochloride salt, it was mixed with an extra equivalent of potassium tert-butoxide in anhydrous N,N-dimethylformamide (1 ml) before being added to the reaction mixture. Water (25 ml) was added and the mixture extracted with ethyl acetate (3×25 ml). The combined extracts were dried (MgSO$_4$) and the solvent removed in vacuo to give the crude products which were purified by flash chromatography (silica) eluting with petroleum ether (40-60) containing an increasing amount of ethyl acetate. The products were checked by $^1$H NMR and where sufficiently pure were taken on to the next stage.

Stage 2: Each tube was charged with the appropriate product from Stage 2 (0.2 mmol) and dissolved in anhydrous N,N-dimethylformamide (2 ml). Potassium tert-butoxide (25 mg, 0.22 mmol) was added followed by tert-butyl bromoacetate (0.04 ml, 0.22 mmol). After stirring at ambient temperature for 3 hours, the mixtures were left to stand for 18 hours. Each of the reaction mixtures was worked up by adding water (about 5 ml) and extracting with ethyl acetate (3×5 ml (approx.)). The extracts were evaporated in tubes using a Genevac HT4 for 2 hours at 60° C. They were then taken on to the next stage.

Stage 3: the final stage was carried out as in the last stage (Stage 2) of method B.

Method D: (Route B, Parallel Method 3)

Stage 1: Reaction vessels were charged with either 5-chloro-1H-spiro[indole-3,3'-pyrrolidine]-2,2',5'-trione, intermediate 9 (500 mg, 1.9 mmol), anhydrous N,N-dimethylformamide (3 ml) and potassium tert-butoxide (235 mg, 1.9 mmol) or 6-chloro-1H-spiro[indole-3,3'-pyrrolidine]-2,2',5'-trione, intermediate 12 (300 mg, 1.2 mmol), anhydrous N,N-dimethylformamide (2.5 ml) and potassium tert-butoxide (141 mg, 1.2 mmol) or 5-trifluoromethoxy-1H-spiro[indole-3,3'-pyrrolidine]-2,2',5'-trione, intermediate 11 (400 mg, 1.6 mmol), anhydrous N,N-dimethylformamide (2.5 ml) and potassium tert-butoxide (188 mg, 1.6 mmol). After stirring at ambient temperature for 40 minutes, the appropriate alkylating agent (1 eq) was added and the mixtures stirred at ambient temperature for 18 hours. If the alkylating agent was in the form of the hydrochloride salt, it was mixed with an extra equivalent of potassium tert-butoxide in anhydrous N,N-dimethylformamide (1 ml) before being added to the reaction mixture. Water (25 ml) was added and the mixture extracted with ethyl acetate (3×25 ml). The combined extracts were dried (MgSO$_4$) and the solvent removed in vacuo to give the crude products which were purified by flash chromatography (silica) eluting with petroleum ether (40-60) containing an increasing amount of ethyl acetate. The products were checked by $^1$H NMR and where sufficiently pure were taken on to the next stage.

Stage 2: Two different procedures were undertaken and each is described below:

Each tube was charged with the appropriate product from Stage 1 (0.2 mmol) and dissolved in anhydrous N,N-dimethylformamide (2 ml). Potassium tert-butoxide (25 mg, 0.22 mmol) was added followed by tert-butyl 4-bromobutyrate (0.04 ml, 0.22 mmol) and the reaction mixtures heated at 50° C. for 18 hours. The reactions were worked up by adding water (about 5 ml) and extracting with ethyl acetate (3×5 ml (approx.)). The extracts were evaporated in tubes using a Genevac HT4 for 2 hours at 60° C. They were then taken on to the next stage.

Each tube was charged with the appropriate product from Stage 1 (0.2 mmol) and dissolved in anhydrous tetrahydrofuran (2 ml). Sodium hydride (60% dispersion on oil, 9 mg, 0.22 mmol) was added and, after stirring at ambient temperature for 40 minutes, tert-butyl acrylate (0.04 ml, 0.26 mmol) was added and the reaction mixtures heated at 30° C. for 18 hours. The reactions were worked up by adding water (about 5 ml) and extracting with ethyl acetate (3×5 ml (approx.)). The extracts were evaporated in tubes using a Genevac HT4 for 2 hours at 60° C. They were then taken on to the next stage.

Stage 3: the final stage was carried out as in the last stage (Stage 2) of method B.

Example 13

[5-chloro-1'-(4-chlorobenzyl)-2,2',5'-trioxospiro[indole-3,3'-pyrrolidin]-1(2H)-yl]acetic acid

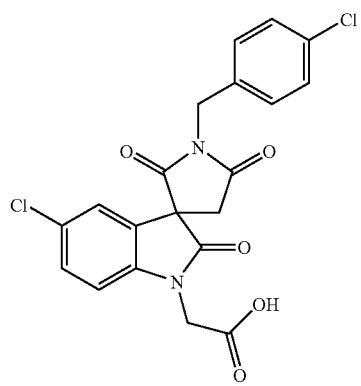

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 58% yield (97% purity by HPLC). MS (ESI$^+$): 434.3; MS (ESI$^-$): 432.4.

Example 14

[5-chloro-1'-(4-methoxybenzyl)-2,2',5'-trioxospiro[indole-3,3'-pyrrolidin]-1(2H)-yl]acetic acid

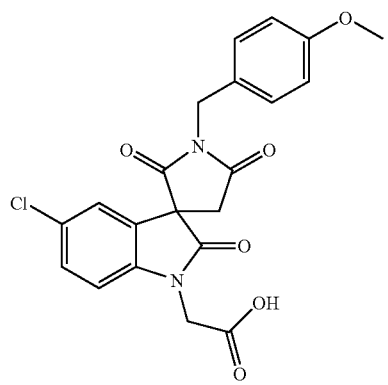

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 80% yield (97% purity by HPLC). MS (ESI$^+$): 429.8; MS (ESI$^-$): 427.8.

Example 15

[5-chloro-1'-(3-methoxybenzyl)-2,2',5'-trioxospiro[indole-3,3'-pyrrolidin]-1(2H)-yl]acetic acid

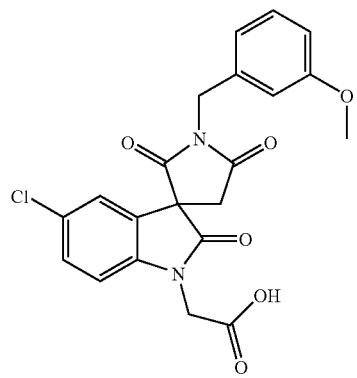

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 75% yield (91% purity by HPLC). MS (ESI$^+$): 429.8; MS (ESI$^-$): 427.8.

Example 16

[5-chloro-1'-(2,3-dihydro-1,4-benzodioxin-2-ylmethyl)-2,2',5'-trioxospiro[indole-3,3'-pyrrolidin]-1(2H)-yl]acetic acid

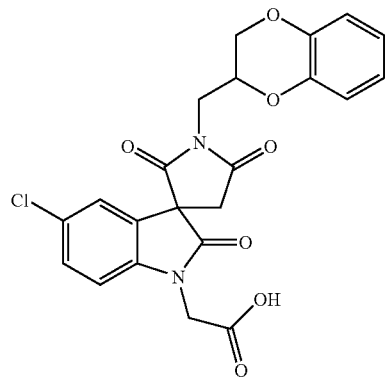

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 70% yield (86% purity by HPLC). MS (ESI$^+$): 434.3; MS (ESI$^-$): 432.4.

Example 17

[5-chloro-2,2',5'-trioxo-1'-(pyridin-2-ylmethyl)spiro[indole-3,3'-pyrrolidin]-1(2H)-yl]acetic acid

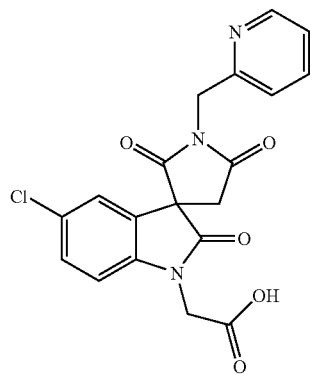

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 69% yield (91.2% purity by HPLC). MS (ESI⁺): 400.8; MS (ESI⁻): 398.9.

Example 18

[5-chloro-2,2',5'-trioxo-1'-{[5-(trifluoromethyl)-2-furyl]methyl}spiro[indole-3,3'-pyrrolidin]-1(2H)-yl]acetic acid

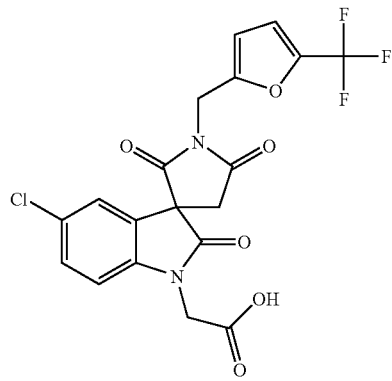

Following the general methods as outlined in Example 12 (Method D), starting from 5-Chloro-1H-spiro[indole-3,3'-pyrrolidine]-2,2',5'-trione (Intermediate 9), the title compound was isolated as a brown solid in 72% yield (96.7% purity by HPLC). MS (ESI⁺): 457.8; MS (ESI⁻): 455.8.

Example 19

[5-chloro-1'-(4-methylbenzyl)-2,2',5'-trioxospiro[indole-3,3'-pyrrolidin]-1(2H)-yl]acetic acid

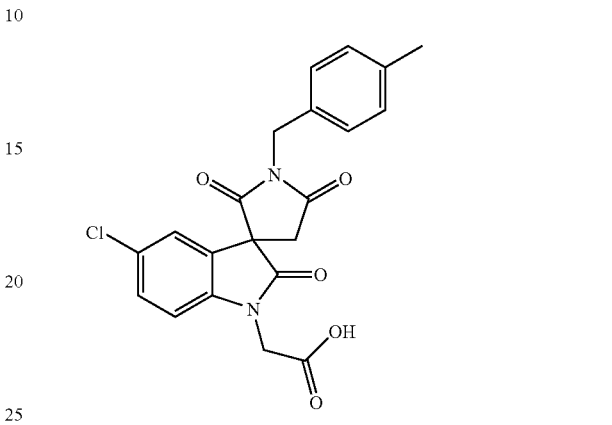

Following the general methods as outlined in Example 12 (Method D), starting from 5-Chloro-1H-spiro[indole-3,3'-pyrrolidine]-2,2',5'-trione (Intermediate 9), the title compound was isolated as a brown solid in 65% yield (88% purity by HPLC). MS (ESI⁺): 413.8; MS (ESI⁻): 411.8.

Example 20

[5-chloro-2,2',5'-trioxo-1'-[3-(trifluoromethyl)benzyl]spiro[indole-3,3'-pyrrolidin]-1(2H)-yl]acetic acid

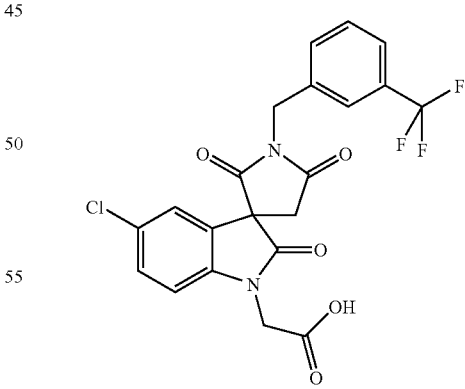

Following the general methods as outlined in Example 12 (Method D), starting from 5-Chloro-1H-spiro[indole-3,3'-pyrrolidine]-2,2',5'-trione (Intermediate 9), the title compound was isolated as a beige oil in 58% yield (92% purity by HPLC). MS (ESI⁺): 467.8; MS (ESI⁻): 465.6.

Example 21

[5-chloro-1'-(2-naphthylmethyl)-2,2',5'-trioxospiro[indole-3,3'-pyrrolidin]-1(2H)-yl]acetic acid

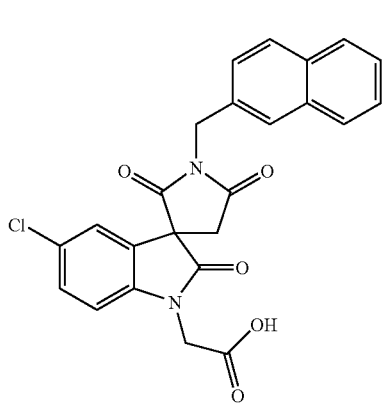

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 74% yield (93% purity by HPLC). MS (ESI$^+$): 449.9; MS (ESI$^-$): 447.9

Example 22

[5-chloro-2,2',5'-trioxo-1'-(1-phenylethyl)spiro[indole-3,3'-pyrrolidin]-1(2H)-yl]acetic acid

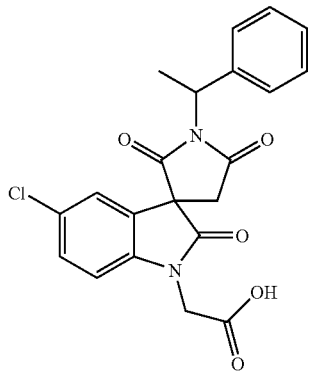

Following the general methods as outlined in Example 12 (Method D), starting from 5-Chloro-1H-spiro[indole-3,3'-pyrrolidine]-2,2',5'-trione (Intermediate 9), the title compound was isolated as a orange solid in 26% yield (94.5% purity by HPLC). MS (ESI$^+$): 413.8; MS (ESI$^-$): 411.7

Example 23

[5-chloro-2,2',5'-trioxo-1'-(2-phenylethyl)spiro[indole-3,3'-pyrrolidin]-1(2H)-yl]acetic acid

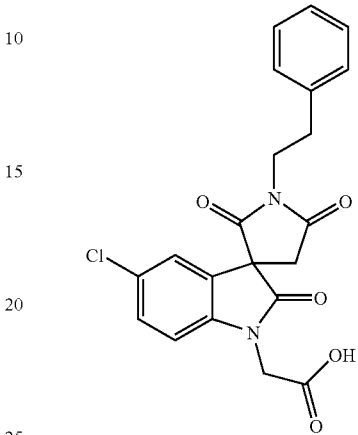

Following the general methods as outlined in Example 12 (Method D), starting from 5-Chloro-1H-spiro[indole-3,3'-pyrrolidine]-2,2',5'-trione (Intermediate 9), the title compound was isolated as a brown solid in 67% yield (96% purity by HPLC). MS (ESI$^+$): 413.8; MS (ESI$^-$): 411.6

Example 24

[5-chloro-1'-(imidazo[1,2-a]pyridin-2-ylmethyl)-2,2',5'-trioxospiro[indole-3,3'-pyrrolidin]-1(2H)-yl]acetic acid

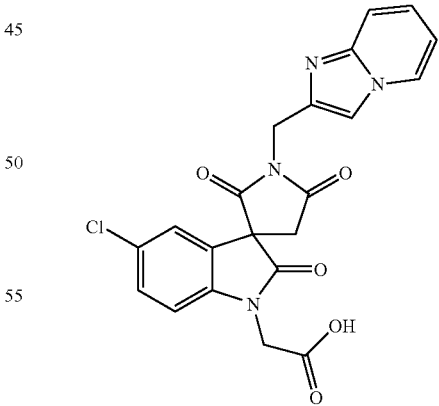

Following the general methods as outlined in Example 12 (Method D), starting from 5-Chloro-1H-spiro[indole-3,3'-pyrrolidine]-2,2',5'-trione (Intermediate 9), the title compound was isolated as a brown solid in 65% yield (95.9% purity by HPLC). MS (ESI$^+$): 439.8; MS (ESI$^-$): 437.8

Example 25

[5-chloro-2,2',5'-trioxo-1'-[(2E)-3-phenylprop-2-en-1-yl]spiro[indole-3,3'-pyrrolidin]-1(2H)-yl]acetic acid

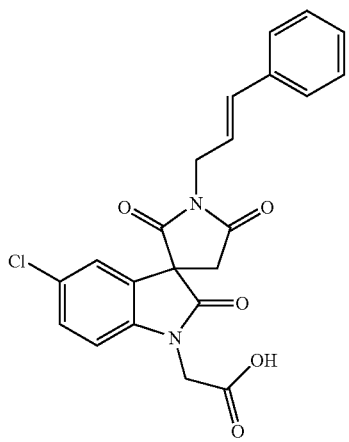

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 60% yield (98% purity by HPLC). MS (ESI$^+$): 425.8; MS (ESI$^-$): 423.6

Example 26

[5-chloro-2,2',5'-trioxo-1'-[4-(trifluoromethyl)benzyl]spiro[indole-3,3'-pyrrolidin]-1(2H)-yl]acetic acid

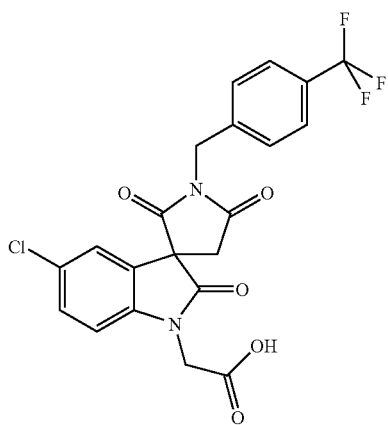

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 63% yield (92% purity by HPLC). MS (ESI$^+$): 467.7; MS (ESI): 465.6

Example 27

4-(1'-benzyl-6-chloro-2,2',5'-trioxospiro[indole-3,3'-pyrrolidin]-1(2H)-yl)butanoic acid

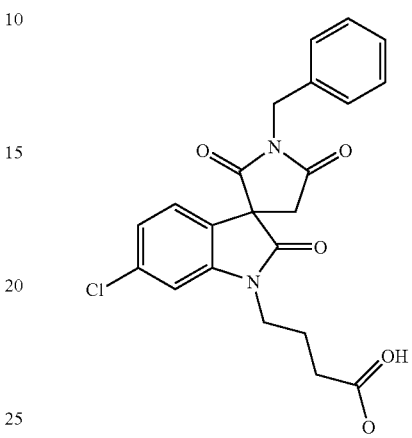

Following the general methods as outlined in Example 12 (Method C), starting from 6-chloro-1H-spiro[indole-3,3'-pyrrolidine]-2,2',5'-trione (intermediate 12), the title compound was isolated as a beige solid in 17% yield (90.4% purity by HPLC). MS (ESI$^+$): 427.9; MS (ESI$^-$): 425.8

Example 28

[5-chloro-1'-(2-ethoxyethyl)-2,2',5'-trioxospiro[indole-3,3'-pyrrolidin]-1(2H)-yl]acetic acid

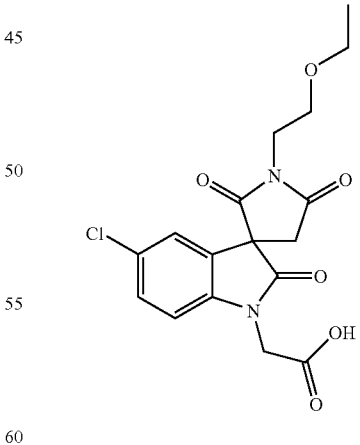

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 69% yield (89% purity by HPLC). MS (ESI$^+$): 381.8; MS (ESI$^-$): 379.8

Example 29

[1'-[2-(benzyloxy)ethyl]-5-chloro-2,2',5'-trioxospiro[indole-3,3'-pyrrolidin]-1(2H)-yl]acetic acid

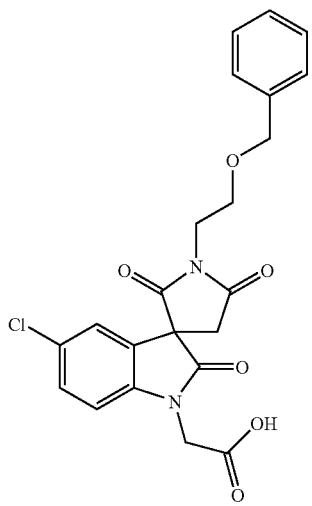

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 65% yield (93% purity by HPLC). MS (ESI$^+$): 443.9; MS (ESI$^-$): 441.8

Example 30

[5-chloro-2,2',5'-trioxo-1'-(2-phenoxyethyl)spiro[indole-3,3'-pyrrolidin]-1(2H)-yl]acetic acid

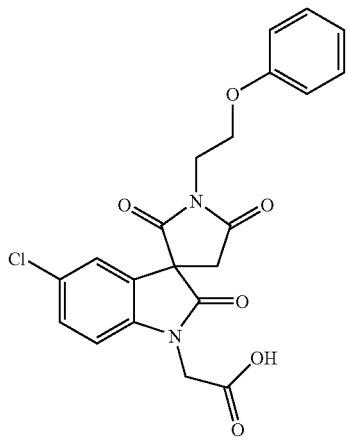

Following the general methods as outlined in Example 12 (Method D), starting from 5-Chloro-1H-spiro[indole-3,3'-pyrrolidine]-2,2',5'-trione (Intermediate 9), the title compound was isolated as a beige solid in 71% yield (91% purity by HPLC). MS (ESI$^+$): 429.8; MS (ESI$^-$): 427.8

Example 31

[5-chloro-2,2',5'-trioxo-1'-(3-phenylprop-2-yn-1-yl)spiro[indole-3,3'-pyrrolidin]-1(2H)-yl]acetic acid

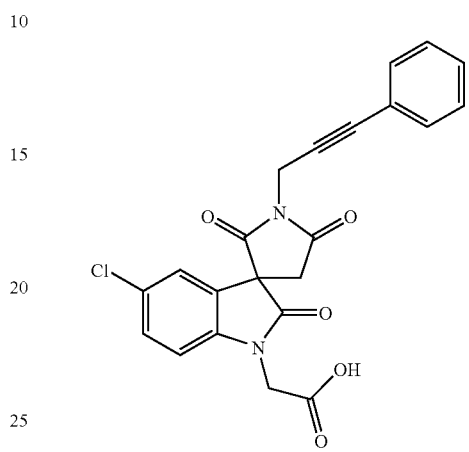

Following the general methods as outlined in Example 12 (Method D), starting from 5-Chloro-1H-spiro[indole-3,3'-pyrrolidine]-2,2',5'-trione (Intermediate 9), the title compound was isolated as a black solid in 56% yield (84.5% purity by HPLC). MS (ESI$^+$): 423.8; MS (ESI$^-$): 421.7

Example 32

(1'-but-2-yn-1-yl-5-chloro-2,2',5'-trioxospiro[indole-3,3'-pyrrolidin]-1(2H)-yl)acetic acid

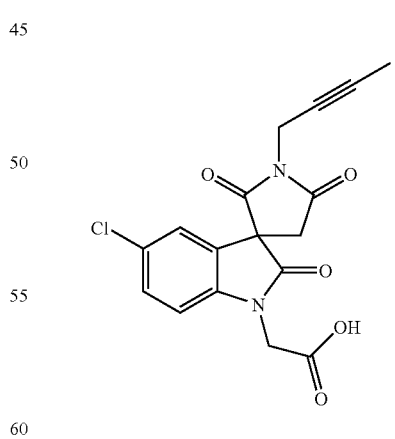

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 69% yield (94% purity by HPLC). MS (ESI$^+$): 361.7; MS (ESI$^-$): 359.8

Example 33

[5-chloro-1'-[(1-methyl-1H-imidazol-2-yl)methyl]-2,2',5'-trioxospiro[indole-3,3'-pyrrolidin]-1(2H)-yl] acetic acid

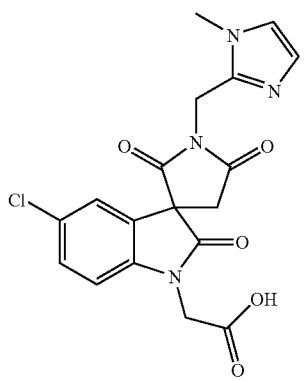

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 51% yield (87% purity by HPLC). MS (ESI+): 403.7; MS (ESI−): 401.8

Example 34

4-[5-chloro-1'-(4-fluorobenzyl)-2,2',5'-trioxospiro[indole-3,3'-pyrrolidin]-1(2H)-yl]butanoic acid

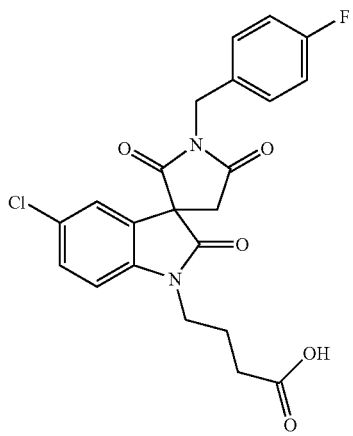

Following the general methods as outlined in Example 12 (Method D), starting from 5-Chloro-1H-spiro[indole-3,3'-pyrrolidine]-2,2',5'-trione (Intermediate 9), the title compound was isolated as a yellow solid in 64% yield (82.2% purity by HPLC). MS (ESI+): 445.7; MS (ESI−): 443.8

Example 35

4-[5-chloro-1'-(4-chlorobenzyl)-2,2',5'-trioxospiro[indole-3,3'-pyrrolidin]-1(2H)-yl]butanoic acid

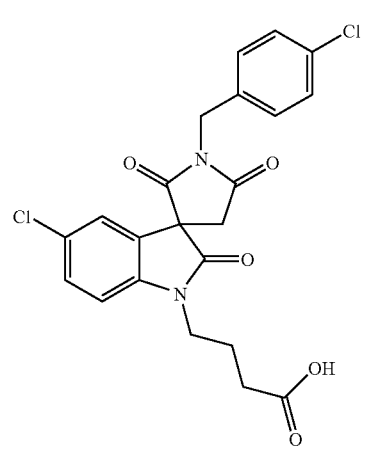

Following the general methods as outlined in Example 12 (Method D), starting from 5-Chloro-1H-spiro[indole-3,3'-pyrrolidine]-2,2',5'-trione (Intermediate 9), the title compound was isolated as a white solid in 62% yield (90% purity by HPLC). MS (ESI+): 462.3; MS (ESI−): 460.2

Example 36

4-[5-chloro-2,2',5'-trioxo-1'-[4-(trifluoromethyl)benzyl]spiro[indole-3,3'-pyrrolidin]-1(2H)-yl]butanoic acid

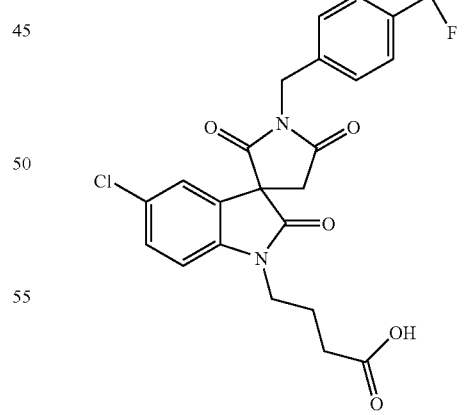

Following the general methods as outlined in Example 12 (Method D), starting from 5-Chloro-1H-spiro[indole-3,3'-pyrrolidine]-2,2',5'-trione (Intermediate 9), the title compound was isolated as a pale-yellow solid in 60% yield (74.3% purity by HPLC). MS (ESI+): 495.9; MS (ESI−): 493.8

Example 37

[1'-benzyl-2,2',5'-trioxo-5-(trifluoromethoxy)spiro[indole-3,3'-pyrrolidin]-1(2H)-yl]acetic acid

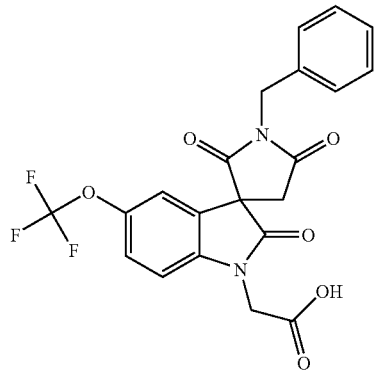

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a white solid in 67% yield (96% purity by HPLC). MS (ESI$^+$): 449.5; MS (ESI$^-$): 447.3

Example 38

[1'-(4-methoxybenzyl)-2,2',5'-trioxo-5-(trifluoromethoxy)spiro[indole-3,3'-pyrrolidin]-1(2H)-yl] acetic acid

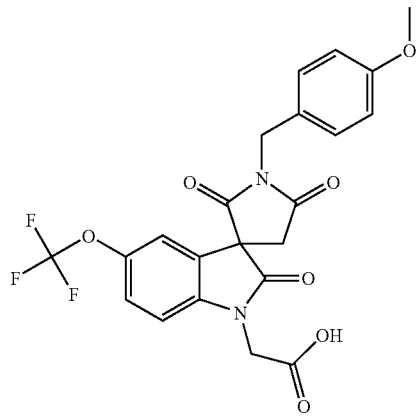

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a pale-brown solid in 74% yield (79% purity by HPLC). MS (ESI$^+$): 479.4; MS (ESI$^-$): 477.3

Example 39

[1'-(3-fluorobenzyl)-2,2',5'-trioxo-5-(trifluoromethoxy)spiro[indole-3,3'-pyrrolidin]-1(2H)-yl] acetic acid

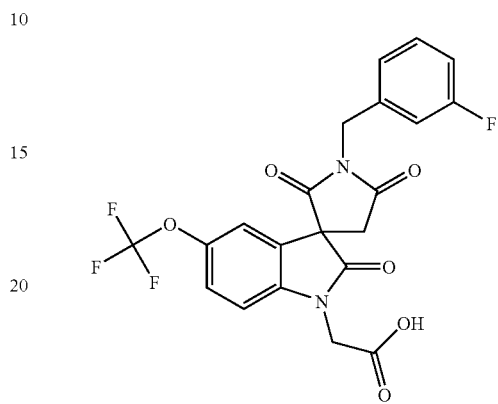

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a white solid in 73% yield (96.9% purity by HPLC). MS (ESI$^+$): 467.4; MS (ESI$^-$): 465.3

Example 40

[1'-(2-fluorobenzyl)-2,2',5'-trioxo-5-(trifluoromethoxy)spiro[indole-3,3'-pyrrolidin]-1(2H)-yl] acetic acid

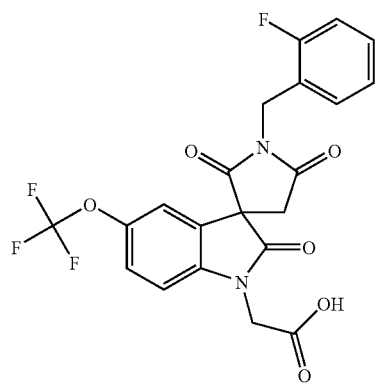

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a white solid in 58% yield (97.3% purity by HPLC). MS (ESI$^+$): 467.4; MS (ESI$^-$): 465.3

Example 41

[2,2',5'-trioxo-5-(trifluoromethoxy)-1'-[3-(trifluoromethyl)benzyl]-spiro[indole-3,3'-pyrrolidin]-1(2H)-yl]acetic acid

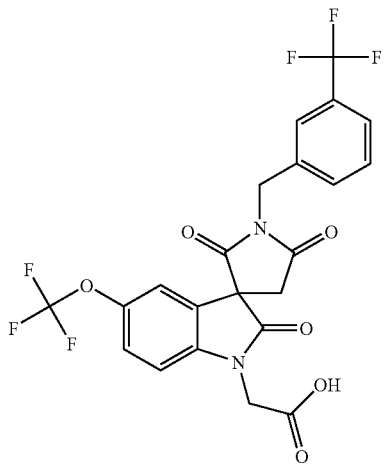

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a pale-brown solid in 68% yield (98.9% purity by HPLC). MS (ESI+): 517.3; MS (ESI−): 515.3

Example 42

[1'-(1-naphthylmethyl)-2,2',5'-trioxo-5-(trifluoromethoxy)spiro[indole-3,3'-pyrrolidin]-1(2H)-yl]acetic acid

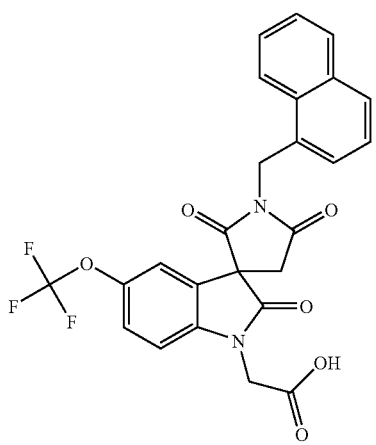

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a white solid in 65% yield (98.9% purity by HPLC). MS (ESI+): 499.5; MS (ESI−): 497.3

Example 43

[1'-(4-chlorobenzyl)-2,2',5'-trioxo-5-(trifluoromethoxy)spiro[indole-3,3'-pyrrolidin]-1(2H)-yl]acetic acid

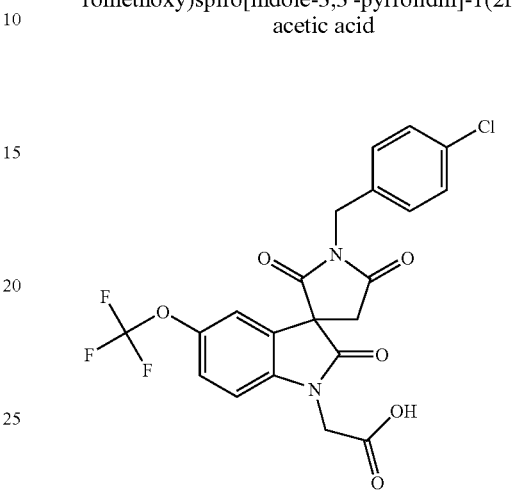

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a pale-brown solid in 56% yield (71.8% purity by HPLC). MS (ESI+): 483.8; MS (ESI−): 481.7

Example 44

[1'-(4-fluorobenzyl)-2,2',5'-trioxo-5-(trifluoromethoxy)spiro[indole-3,3'-pyrrolidin]-1(2H)-yl]acetic acid

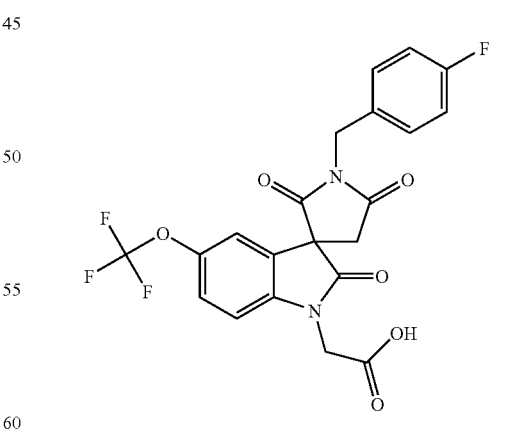

Following the general methods as outlined in Example 12 (Method C), starting from 5-trifluoromethoxy-1H-spiro[indole-3,3'-pyrrolidine]-2,2',5'-trione (Intermediate 11), the title compound was isolated as a white solid in 66% yield (82.7% purity by HPLC). MS (ESI+): 467.5; MS (ESI−): 465.2

Example 45

4-[5-chloro-1'-(4-methoxybenzyl)-2,2',5'-trioxospiro[indole-3,3'-pyrrolidin]-1(2M-yl]butanoic acid

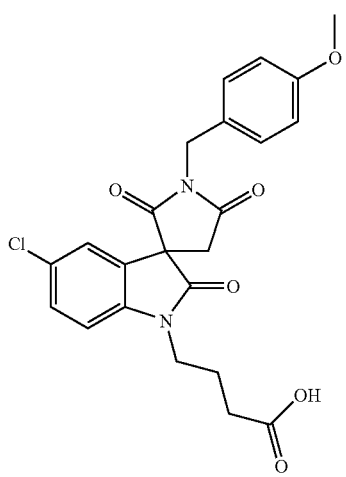

Following the general methods as outlined in Example 12 (Method C), starting from 5-Chloro-1H-spiro[indole-3,3'-pyrrolidine]-2,2',5'-trione (Intermediate 9), the title compound was isolated as a pale-yellow solid in 61% yield (100% purity by HPLC). MS (ESI+): 457.9; MS (ESI−): 455.8

Example 46

4-[5-chloro-1'-(2-fluorobenzyl)-2,2',5'-trioxospiro[indole-3,3'-pyrrolidin]-1(2H)-yl]butanoic acid

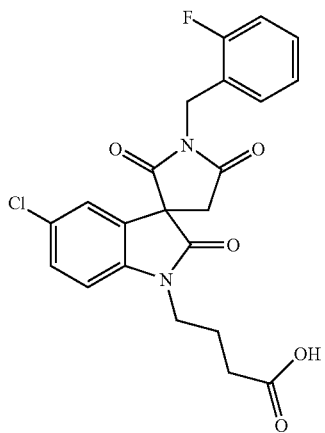

Following the general methods as outlined in Example 12 (Method C), starting from 5-Chloro-1H-spiro[indole-3,3'-pyrrolidine]-2,2',5'-trione (Intermediate 9), the title compound was isolated as a pale-yellow solid in 54% yield (96.5% purity by HPLC). MS (ESI+): 445.9; MS (ESI−): 443.6

Example 47

[(3S)-1'-benzyl-5-chloro-2,2',5'-trioxospiro[indole-3,3'-pyrrolidin]-1(2H)-yl]acetic acid

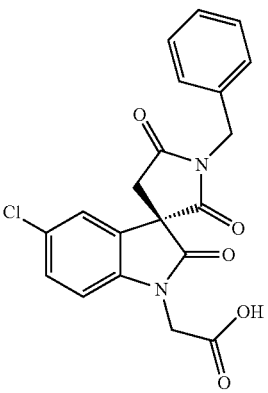

Following purification on chiral column ChiralPak-AD-H, eluting with Ethanol: 0.5% formic acid, of example 12 the title compound was isolated as a white solid (100% purity by HPLC). MS (ESI+): 399.8; MS (ESI−): 397.7; Retention time (chiral HPLC): 8.30 min

Example 48

[(3R)-1'-benzyl-5-chloro-2,2',5'-trioxospiro[indole-3,3'-pyrrolidin]-1(2H)-yl]acetic acid

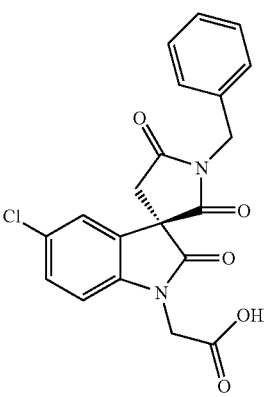

Following purification on chiral column ChiralPak-AD-H, eluting with Ethanol: 0.5% formic acid, of example 12, the title compound was isolated as a white solid (100% purity by HPLC). MS (ESI+): 399.8; MS (ESI−): 397.7; Retention time (chiral HPLC): 5.62 min

Examples 49-108

Following the general methods as outlined in Example 12 (Method C), the following compounds were also prepared. Some compounds are single enantiomers, obtained following purification on chiral column ChiralPak-AD-H, eluting with Ethanol plus 0.5% formic acid.

| Example. | Name | Structure | HPLC purity (%) | MS |
|---|---|---|---|---|
| 49 | [6-chloro-1'-(2-fluorobenzyl)-2,2',5'-trioxospiro[indole-3,3'-pyrrolidin]-1(2H)-yl]acetic acid | 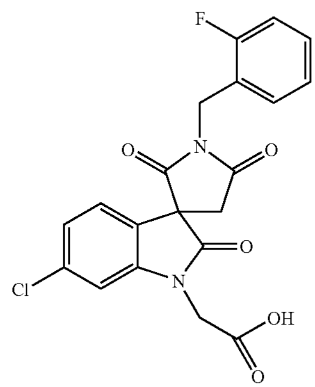 | 91.5 | 417.2 (ESI+) 415.1 (ESI−) |
| 50 | [6-chloro-1'-(3-fluorobenzyl)-2,2',5'-trioxospiro[indole-3,3'-pyrrolidin]-1(2H)-yl]acetic acid | 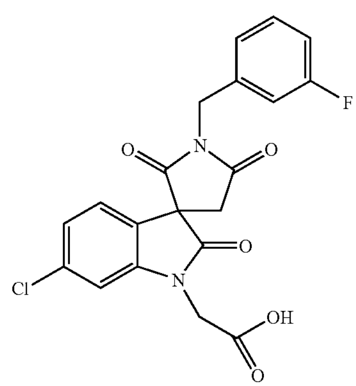 | 93.1 | 417.1 (ESI+) 415.1 (ESI−) |
| 51 | [6-chloro-1'-(4-fluorobenzyl)-2,2',5'-trioxospiro[indole-3,3'-pyrrolidin]-1(2H)-yl]acetic acid | 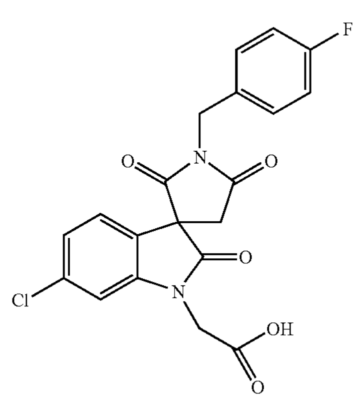 | 77.6 | 417.1 (ESI+) 415.1 (ESI−) |

-continued

| Example. | Name | Structure | HPLC purity (%) | MS |
|---|---|---|---|---|
| 52 | 4-[5-chloro-2,2',5'-trioxo-1'-(2-phenylethyl)spiro[indole-3,3'-pyrrolidin]-1(2H)-yl]butanoic acid | 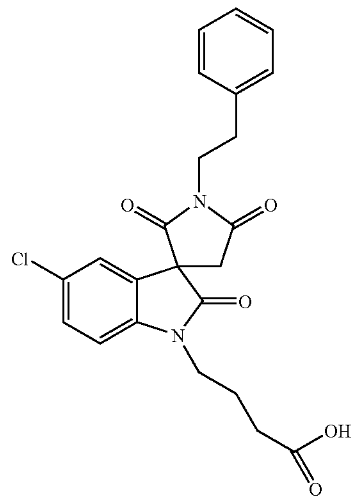 | 74.5 | 441.2 (ESI+) 439.2 (ESI−) |
| 53 | [5-chloro-1'-(3,5-dichlorobenzyl)-2,2',5'-trioxospiro[indole-3,3'-pyrrolidin]-1(2H)-yl]acetic acid | 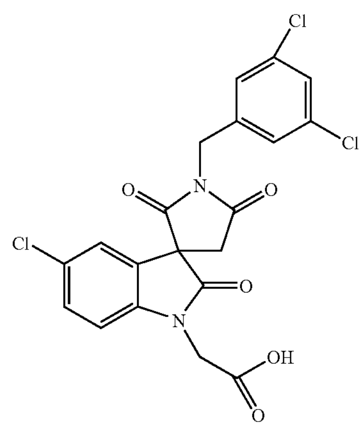 | 95.7 | 466 (ESI+) 464 (ESI−) |
| 54 | [5-chloro-2,2',5'-trioxo-1'-(4-phenoxybenzyl)spiro[indole-3,3'-pyrrolidin]-1(2H)-yl]acetic acid | 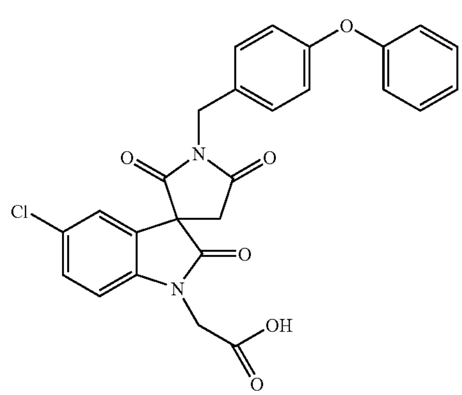 | 97.8 | 491 (ESI+) 489 (ESI−) |

| Example. | Name | Structure | HPLC purity (%) | MS |
|---|---|---|---|---|
| 55 | [5-chloro-1'-(2-methoxybenzyl)-2,2',5'-trioxospiro[indole-3,3'-pyrrolidin]-1(2H)-yl]acetic acid | 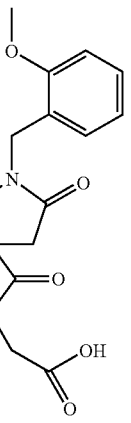 | 98.8 | 429 (ESI+)<br>427 (ESI−) |
| 56 | [5-chloro-1'-[4-(methylsulfonyl)benzyl]-2,2',5'-trioxospiro[indole-3,3'-pyrrolidin]-1(2H)-yl]acetic acid | 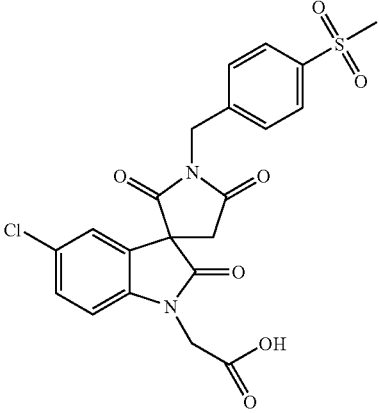 | 96.2 | 477 (ESI+)<br>475 (ESI−) |
| 57 | [1'-[4-(aminocarbonyl)benzyl]-5-chloro-2,2',5'-trioxospiro[indole-3,3'-pyrrolidin]-1(2H)-yl]acetic acid | 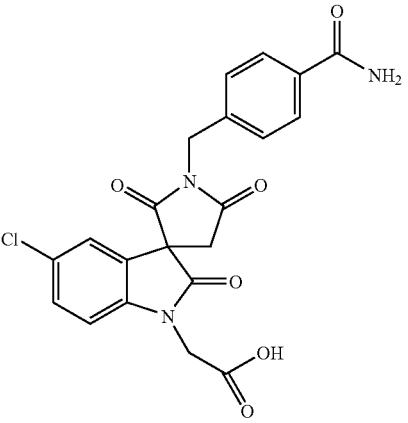 | 87.1 | 442 (ESI+)<br>440 (ESI−) |

-continued

| Example. | Name | Structure | HPLC purity (%) | MS |
|---|---|---|---|---|
| 58 | [5-chloro-1'-(3-cyanobenzyl)-2,2',5'-trioxospiro[indole-3,3'-pyrrolidin]-1(2H)-yl]acetic acid | 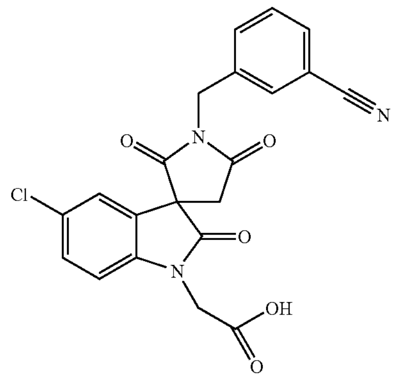 | 84 | 442 (ESI+) 440 (ESI−) |
| 59 | [5-chloro-1'-[(5-methylisoxazol-3-yl)methyl]-2,2',5'-trioxospiro[indole-3,3'-pyrrolidin]-1(2H)-yl]acetic acid | 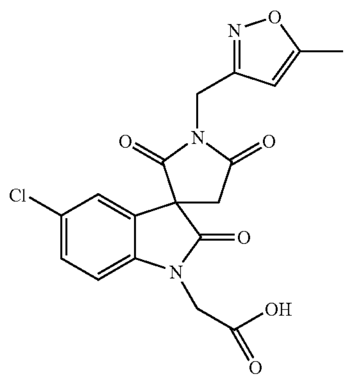 | 83.6 | 404 (ESI+) 402 (ESI−) |
| 60 | [1'-(1,3-benzothiazol-2-ylmethyl)-5-chloro-2,2',5'-trioxospiro[indole-3,3'-pyrrolidin]-1(2H)-yl]acetic acid | 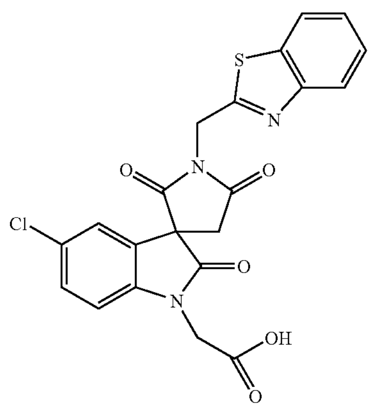 | 83.5 | 456 (ESI+) 454 (ESI−) |
| 61 | [5-chloro-1'-[(5-chloro-2-thienyl)methyl]-2,2',5'-trioxospiro[indole-3,3'-pyrrolidin]-1(2H)-yl]acetic acid | 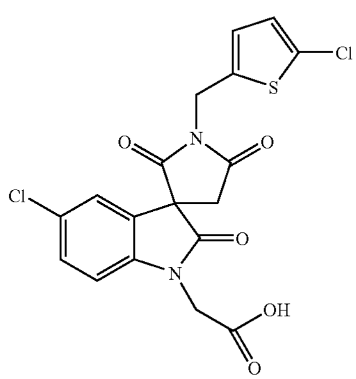 | 82.1 | 439 (ESI+) 437 (ESI−) |

-continued

| Example. | Name | Structure | HPLC purity (%) | MS |
|---|---|---|---|---|
| 62 | [5-chloro-1'-[(5-chloro-1,2,4-thiadiazol-3-yl)methyl]-2,2',5'-trioxospiro[indole-3,3'-pyrrolidin]-1(2H)-yl]acetic acid | 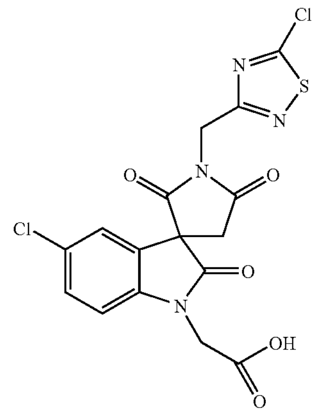 | 84.3 | 441 (ESI+) 439 (ESI−) |
| 63 | [5-chloro-2,2',5'-trioxo-1'-[(2-phenyl-1,3-thiazol-4-yl)methyl]spiro[indole-3,3'-pyrrolidin]-1(2H)-yl]acetic acid | 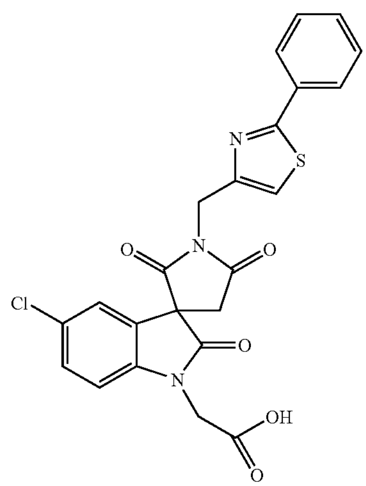 | 87.6 | 482 (ESI+) 480 (ESI−) |
| 64 | [5-chloro-1'-(2-chloro-4-fluorobenzyl)-2,2',5'-trioxospiro[indole-3,3'-pyrrolidin]-1(2H)-yl]acetic acid | 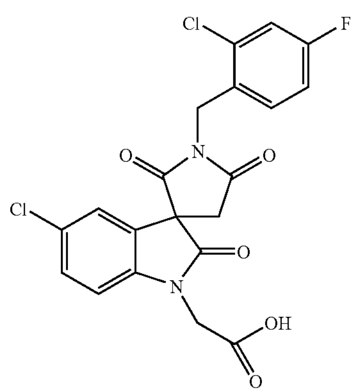 | 85.1 | 451 (ESI+) 449 (ESI−) |

-continued
| Example. | Name | Structure | HPLC purity (%) | MS |
|---|---|---|---|---|
| 65 | [5-chloro-1'-(2,5-dichlorobenzyl)-2,2',5'-trioxospiro[indole-3,3'-pyrrolidin]-1(2H)-yl]acetic acid | 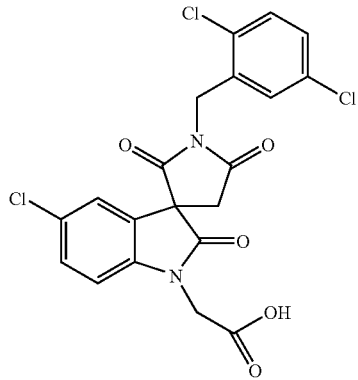 | 89.1 | 467 (ESI+) 465 (ESI−) |
| 66 | [1'-[4-(acetylamino)benzyl]-5-chloro-2,2',5'-trioxospiro[indole-3,3'-pyrrolidin]-1(2H)-yl]acetic acid | 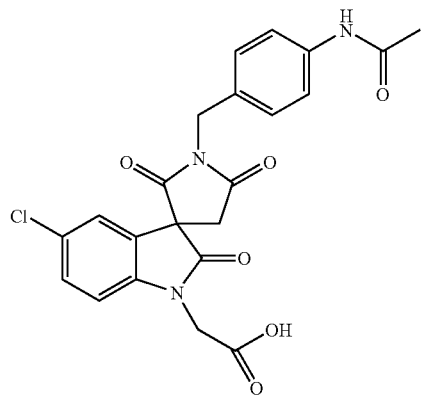 | 85.6 | 456 (ESI+) 454 (ESI−) |
| 67 | [5-chloro-1'-[(6-chloropyridin-3-yl)methyl]-2,2',5'-trioxospiro[indole-3,3'-pyrrolidin]-1(2H)-yl]acetic acid | 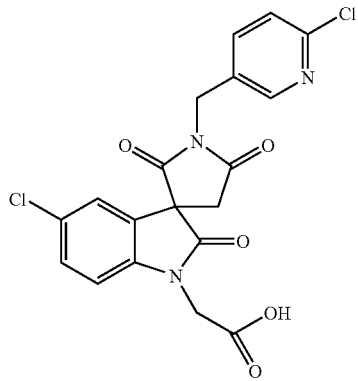 | 88.5 | 434 (ESI+) 432 (ESI−) |

-continued

| Example. | Name | Structure | HPLC purity (%) | MS |
|---|---|---|---|---|
| 68 | [5-chloro-1'-(1H-indol-3-ylmethyl]-2,2',5'-trioxospiro[indole-3,3'-pyrrolidin]-1(2H)-yl]acetic acid | 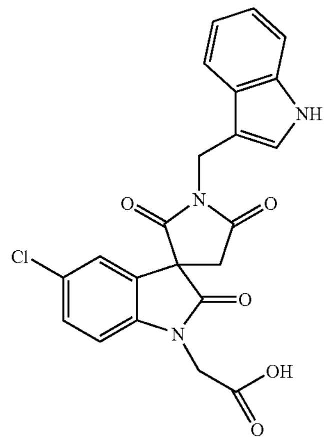 | 95.3 | 438 (ESI+)<br>436 (ESI−) |
| 69 | [5-chloro-1'-(5-chloro-2-fluorobenzyl)-2,2',5'-trioxospiro[indole-3,3'-pyrrolidin]-1(2H)-yl]acetic acid | 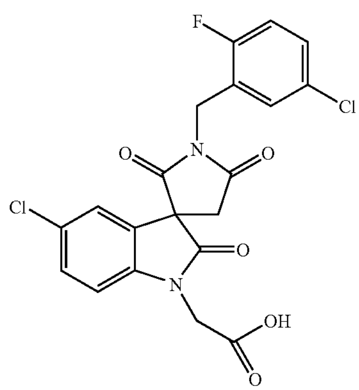 | 98.9 | 451.3 (ESI+)<br>449.3 (ESI−) |
| 70 | [5-chloro-2,2',5'-trioxo-1'-(1,3-thiazol-4-ylmethyl)spiro[indole-3,3'-pyrrolidin]-1(2H)-yl]acetic acid | 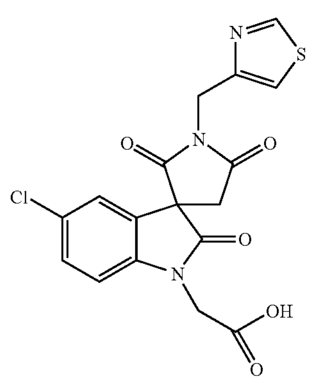 | 93.9 | 406 (ESI+)<br>404 (ESI−) |

-continued

| Example. | Name | Structure | HPLC purity (%) | MS |
|---|---|---|---|---|
| 71 | [5-chloro-1'-[(4-chloropyridin-3-yl)methyl]-2,2',5'-trioxospiro[indole-3,3'-pyrrolidin]-1(2H)-yl]acetic acid | 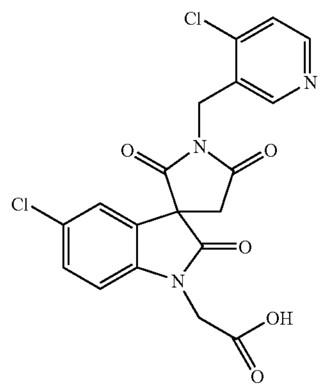 | 87.3 | 434 (ESI+) 432 (ESI−) |
| 72 | [5-chloro-2,2',5'-trioxo-1'-(pyridin-3-ylmethyl)spiro[indole-3,3'-pyrrolidin]-1(2H)-yl]acetic acid | 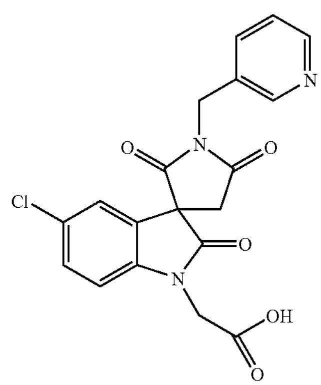 | 90.4 | 400 (ESI+) 398 (ESI−) |
| 73 | [5-chloro-1'-[(3,5-dimethylisoxazol-4-yl)methyl]-2,2',5'-trioxospiro[indole-3,3'-pyrrolidin]-1(2H)-yl]acetic acid | 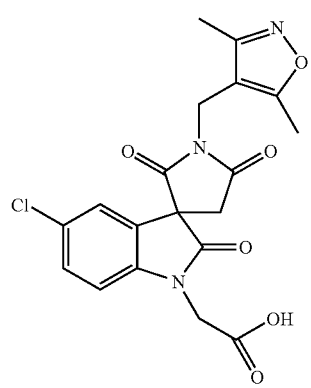 | 98.9 | 418 (ESI+) 416 (ESI−) |

-continued

| Example. | Name | Structure | HPLC purity (%) | MS |
|---|---|---|---|---|
| 74 | [1'-[(5-tert-butyl-1,2,4-oxadiazol-3-yl)methyl]-5-chloro-2,2',5'-trioxospiro[indole-3,3'-pyrrolidin]-1(2H)-yl]acetic acid | 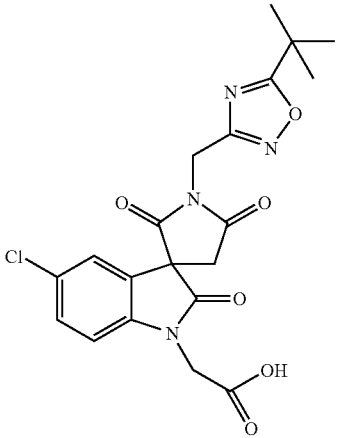 | 98.5 | 447 (ESI+) |
| 75 | [5-chloro-1'-[(5-cyclopropyl-1,3,4-thiadiazol-2-yl)methyl]-2,2',5'-trioxospiro[indole-3,3'-pyrrolidin]-1(2H)-yl]acetic acid | 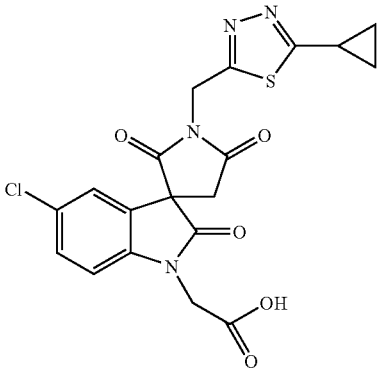 | 98.2 | 447 (ESI+)<br>445 (ESI−) |
| 76 | [5-chloro-1'-[(4-methoxy-3,5-dimethylpyridin-2-yl)methyl]-2,2',5'-trioxospiro[indole-3,3'-pyrrolidin]-1(2H)-yl]acetic acid | 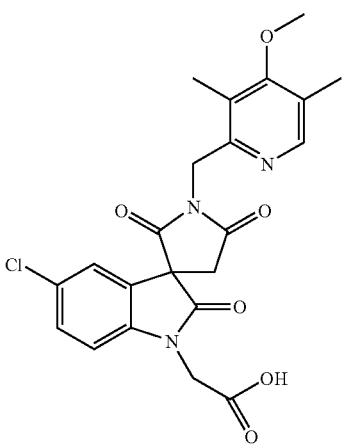 | 96.2 | 458 (ESI+)<br>456 (ESI−) |

-continued

| Example. | Name | Structure | HPLC purity (%) | MS |
|---|---|---|---|---|
| 77 | [5-chloro-1'-[(4,6-dichloropyridin-3-yl)methyl]-2,2',5'-trioxospiro[indole-3,3'-pyrrolidin]-1(2H)-yl]acetic acid | 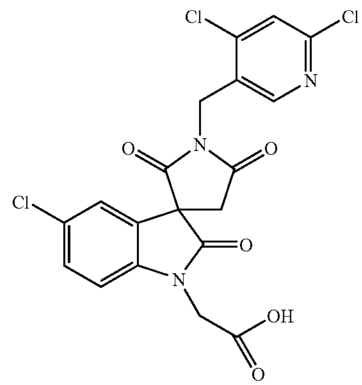 | 97.5 | 468 (ESI+) 466 (ESI−) |
| 78 | [5-chloro-2,2',5'-trioxo-1'-(2-thienylmethyl)spiro[indole-3,3'-pyrrolidin]-1(2H)-yl]acetic acid | 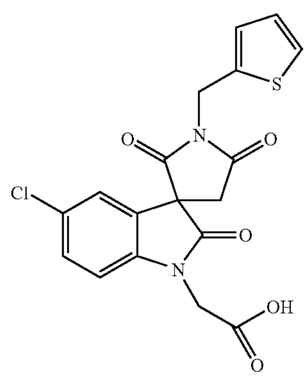 | 85.3 | 405 (ESI+) 403 (ESI−) |
| 79 | [5-chloro-1'-[(3,4-dimethoxypyridin-2-yl)methyl]-2,2',5'-trioxospiro[indole-3,3'-pyrrolidin]-1(2H)-yl]acetic acid | 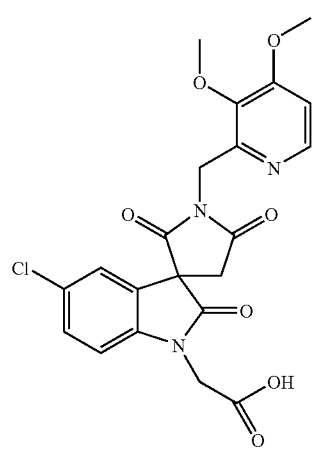 | 87.5 | 460 (ESI+) 458 (ESI−) |

-continued

| Example. | Name | Structure | HPLC purity (%) | MS |
|---|---|---|---|---|
| 80 | [5-chloro-1'-(isoquinolin-1-ylmethyl)-2,2',5'-trioxospiro[indole-3,3'-pyrrolidin]-1(2H)-yl]acetic acid | 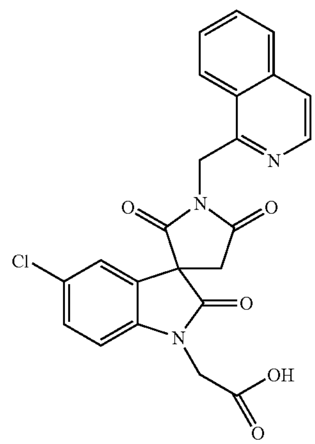 | 87.5 | 450 (ESI+) 448 (ESI−) |
| 81 | [5-chloro-2,2',5'-trioxo-1'-[(5-phenyl-1,2,4-oxadiazol-3-yl)methyl]spiro[indole-3,3'-pyrrolidin]-1(2H)-yl]acetic acid | 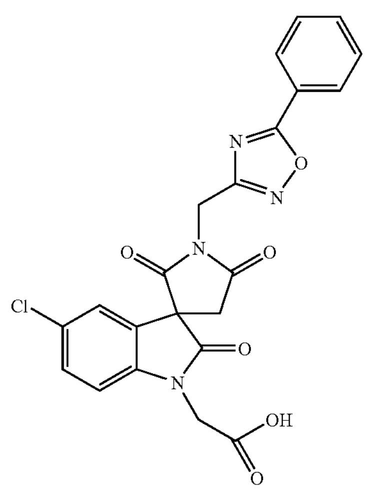 | 96.3 | 467 (ESI+) 465 (ESI−) |
| 82 | 1'-benzyl-5-chloro-1-(1H-tetrazol-5-ylmethyl)-2'H,5'H-spiro[indole-3,3'-pyrrolidine]-2,2',5'(1H)-trione | 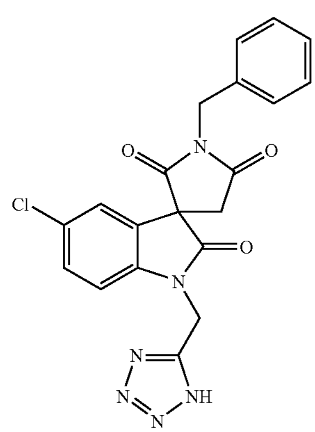 | 79.3 | 423 (ESI+) 421 (ESI−) |

| Example. | Name | Structure | | HPLC purity (%) | MS |
|---|---|---|---|---|---|
| 83 | (3R)-[5-chloro-1'-(3-chlorobenzyl)-2,2',5'-trioxospiro[indole-3,3'-pyrrolidin]-1(2H)-yl]acetic acid | 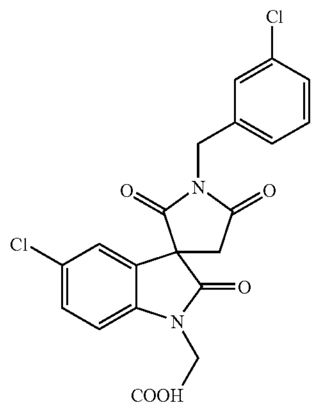 | ABS | 99.1 (retention time chiral HPLC 7.21 min) | 433.3 (ESI+) 431.1 (ESI−) |
| 84 | (3S)-[5-chloro-1'-(3-chlorobenzyl)-2,2',5'-trioxospiro[indole-3,3'-pyrrolidin]-1(2H)-yl]acetic acid | 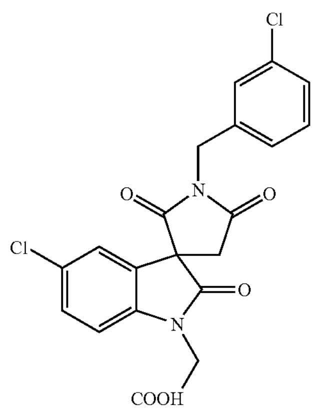 | ABS | 99.7 (retention time chiral HPLC 10.98 min) | 433.5 (ESI+) 431.3 (ESI−) |
| 85 | (3R)-[5-chloro-1'-(3-methoxybenzyl)-2,2',5'-trioxospiro[indole-3,3'-pyrrolidin]-1(2H)-yl]acetic acid | 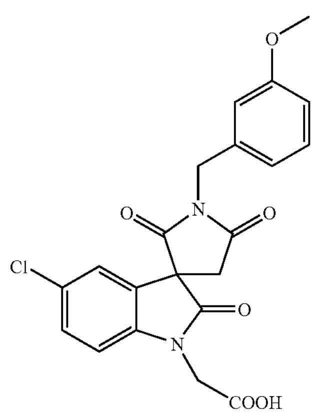 | ABS | 99.8 (retention time chiral HPLC 5.88 min) | 429.4 (ESI+) 427.3 (ESI−) |

-continued

| Example. | Name | Structure | HPLC purity (%) | MS |
|---|---|---|---|---|
| 86 | (3S)-[5-chloro-1'-(3-methoxybenzyl)-2,2',5'-trioxospiro[indole-3,3'-pyrrolidin]-1(2H)-yl]acetic acid | ABS | 99 (retention time chiral HPLC 9.66 min) | 429.4 (ESI+)<br>427.2 (ESI−) |
| 87 | [5-chloro-1'-(2,4-difluorobenzyl)-2,2',5'-trioxospiro[indole-3,3'-pyrrolidin]-1(2H)-yl]acetic acid | 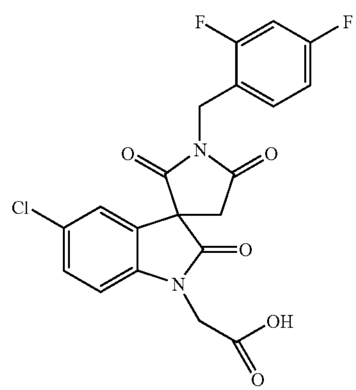 | 93.6 | 435 (ESI+)<br>433 (ESI−) |
| 88 | [5-chloro-1'-(1,3-oxazol-2-ylmethyl)-2,2',5'-trioxospiro[indole-3,3'-pyrrolidin]-1(2H)-yl]acetic acid | 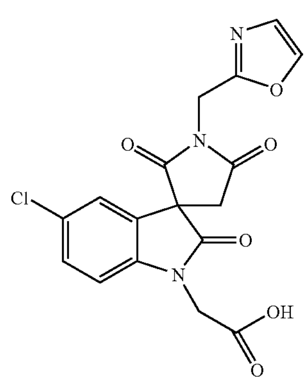 | 97 | 390 (ESI+)<br>388 (ESI−) |

-continued

| Example. | Name | Structure | HPLC purity (%) | MS |
|---|---|---|---|---|
| 89 | [5-chloro-1'-[(4-methoxy-3-methylpyridin-2-ylmethyl)-2,2',5'-trioxospiro[indole-3,3'-pyrrolidin]-1(2H)-yl]acetic acid | 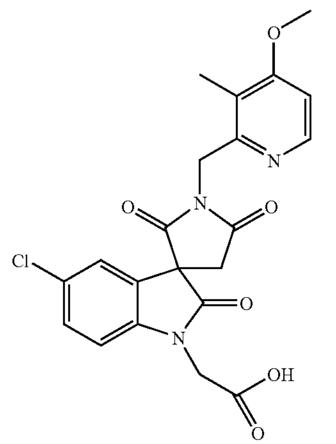 | 97.4 | 444 (ESI+) 442 (ESI−) |
| 90 | [5-chloro-1'-{[2-(4-chlorophenyl)-1,3-thiazol-4-yl]methyl}-2,2',5'-trioxospiro[indole-3,3'-pyrrolidin]-1(2H)-yl]acetic acid | 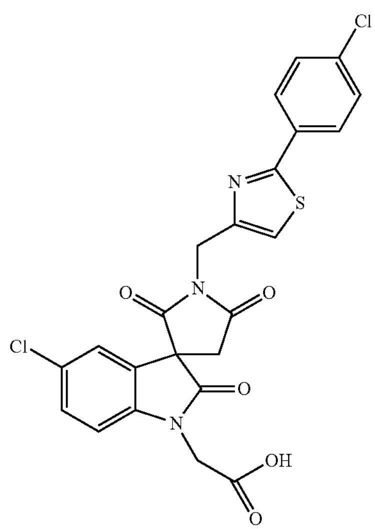 | 99.1 | 516 (ESI+) 514 (ESI−) |
| 91 | [5-chloro-1'-{[5-(4-methoxyphenyl)-1,2,4-oxadiazol-3-yl]methyl}-2,2',5'-trioxospiro[indole-3,3'-pyrrolidin]-1(2H)-yl]acetic acid | 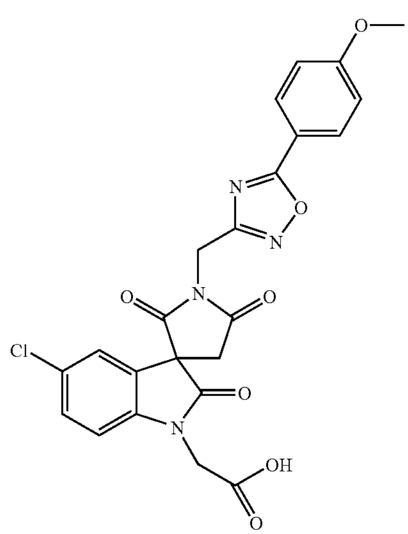 | 98.9 | 497 (ESI+) 495 (ESI−) |

-continued
| Example. | Name | Structure | HPLC purity (%) | MS |
|---|---|---|---|---|
| 92 | [5-chloro-1'-[(1-methyl-1H-1,2,3-benzotriazol-5-yl)methyl-2,2',5'-pyrrolidin]-1(2H)-yl]acetic acid | 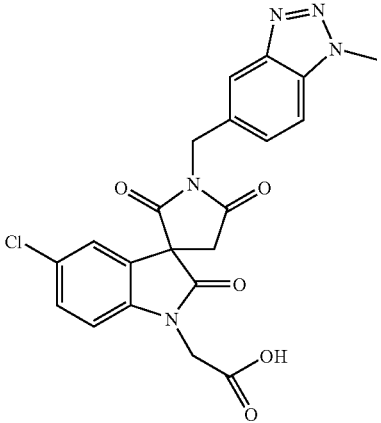 | 98.2 | 454 (ESI+) 452 (ESI−) |
| 93 | [5-chloro-1'-(3-furylmethyl)-2,2',5'-trioxospiro[indole-3,3'-pyrrolidin]-1(2H)-yl]acetic acid | 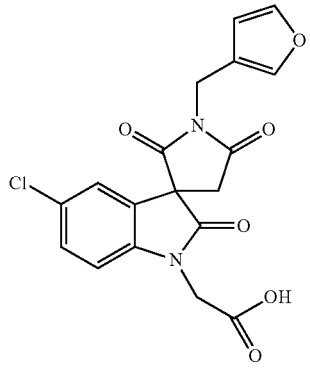 | 94.7 | 389 (ESI+) 387 (ESI−) |
| 94 | [5-chloro-1'-(2-chloro-5-fluorobenzyl)-2,2',5'-trioxospiro[indole-3,3'-pyrrolidin]-1(2H)-yl]acetic acid | 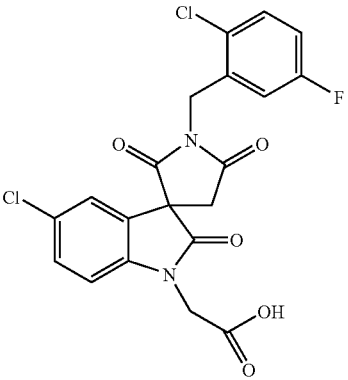 | 97.8 | 451 (ESI+) 449 (ESI−) |

-continued
| Example. | Name | Structure | HPLC purity (%) | MS |
|---|---|---|---|---|
| 95 | [5-chloro-1'-(2,5-difluorobenzyl)-2,2',5'-trioxospiro[indole-3,3'-pyrrolidin]-1(2H)-yl]acetic acid | 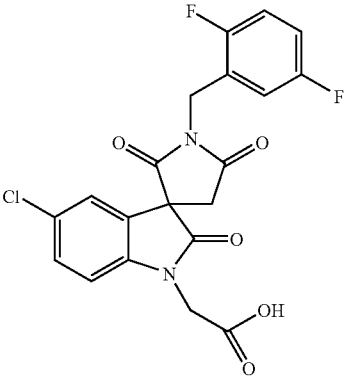 | 98.8 | 435 (ESI+) 433 (ESI−) |
| 96 | [5-chloro-1'-(2,3-difluorobenzyl)-2,2',5'-trioxospiro[indole-3,3'-pyrrolidin]-1(2H)-yl]acetic acid | 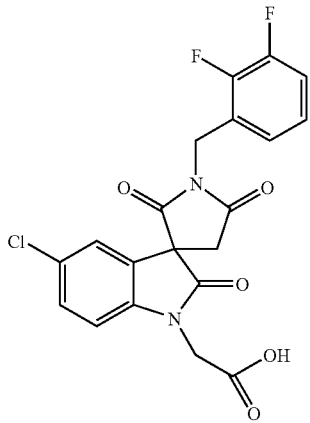 | 98.3 | 435 (ESI+) 433 (ESI−) |
| 97 | [5-chloro-1'-(3,5-difluorobenzyl)-2,2',5'-trioxospiro[indole-3,3'-pyrrolidin]-1(2H)-yl]acetic acid | 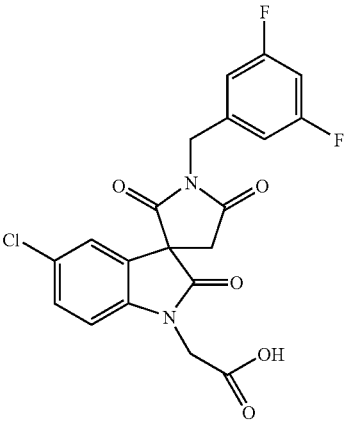 | 98.5 | 435 (ESI+) 433 (ESI−) |

-continued

| Example. | Name | Structure | HPLC purity (%) | MS |
|---|---|---|---|---|
| 98 | [5-chloro-1'-(3,4-difluorobenzyl)-2,2',5'-trioxospiro[indole-3,3'-pyrrolidin]-1(2H)-yl]acetic acid | 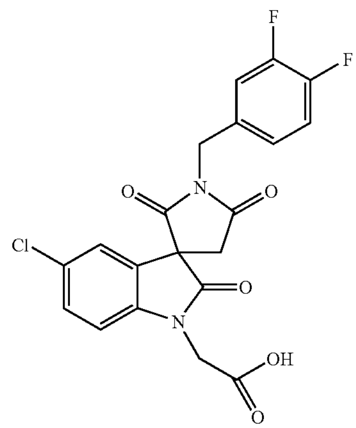 | 99.5 | 435 (ESI+)<br>433 (ESI−) |
| 99 | [5-chloro-1'-[(1-methyl-1H-benzimidazol-2-yl)methyl]-2,2',5'-trioxospiro[indole-3,3'-pyrrolidin]-1(2H)-yl]acetic acid | 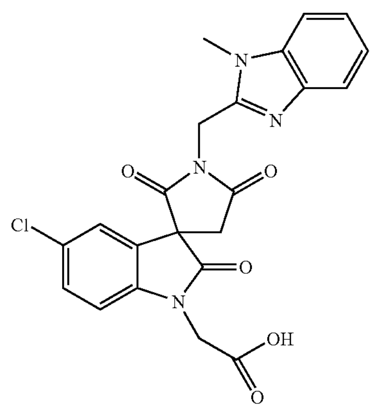 | 97.9 | 453 (ESI+)<br>451 (ESI−) |
| 100 | [5-chloro-1'-(3-fluoro-4-methoxybenzyl)-2,2',5'-trioxospiro[indole-3,3'-pyrrolidin]-1(2H)-yl]acetic acid | 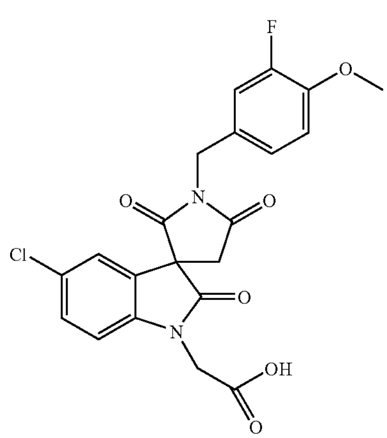 | 99.7 | 447 (ESI+)<br>445 (ESI−) |

-continued

| Example. | Name | Structure | HPLC purity (%) | MS |
|---|---|---|---|---|
| 101 | [5-chloro-1'-(3-chloro-5-fluorobenzyl)-2,2',5'-trioxospiro[indole-3,3'-pyrrolidin]-1(2H)-yl]acetic acid | 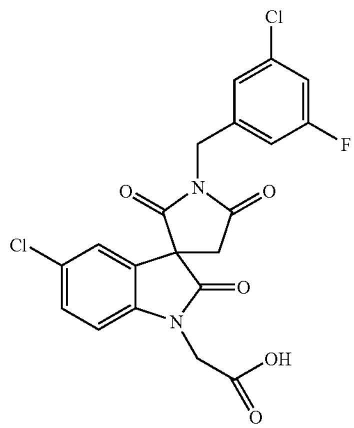 | 99.2 | 451 (ESI+) 449 (ESI−) |
| 102 | [5-chloro-1'-[(5-methyl-3-phenylisoxazol-4-yl)methyl]-2,2',5'-trioxospiro[indole-3,3'-pyrrolidin]-1(2H)-yl]acetic acid | 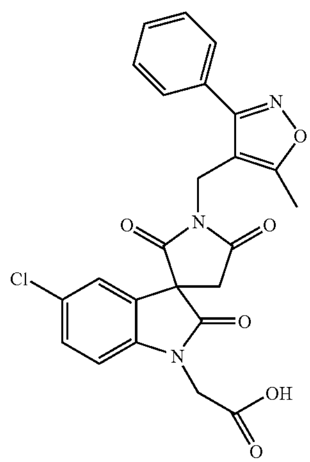 | 99.5 | 480 (ESI+) 478 (ESI−) |
| 103 | [5-chloro-1'-[(3-methyl-5-phenylisoxazol-4-yl)methyl]-2,2',5'-trioxospiro[indole-3,3'-pyrrolidin]-1(2H)-yl]acetic acid | 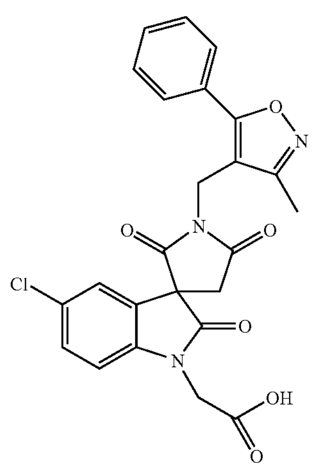 | 99.6 | 480 (ESI+) 478 (ESI−) |

| Example. | Name | Structure | HPLC purity (%) | MS |
|---|---|---|---|---|
| 104 | [5-chloro-1'-{[2-(3-chlorophenyl)-1,3-thiazol-4-yl]methyl}-2,2',5'-trioxospiro[indole-3,3'-pyrrolidin]-1(2H)-yl]acetic acid | 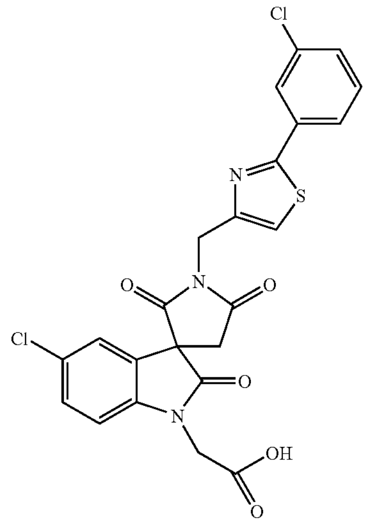 | 99 | 516 (ESI+) 514 (ESI−) |
| 105 | (3R)-[5-chloro-1'-(2-fluorobenzyl)-2,2',5'-trioxospiro[indole-3,3'-pyrrolidin]-1(2H)-yl]acetic acid | ABS | 99.5 (retention time chiral HPLC 5.10 min) | 417.2 (ESI+) 414.9 (ESI−) |
| 106 | (3S)-[5-chloro-1'-(2-fluorobenzyl)-2,2',5'-trioxospiro[indole-3,3'-pyrrolidin]-1(2H)-yl]acetic acid | ABS | 98.8 (retention time chiral HPLC 6.60 min) | 417.3 (ESI+) 415.3 (ESI−) |

| Example. | Name | Structure | HPLC purity (%) | MS |
|---|---|---|---|---|
| 107 | (3S)-[5-chloro-1'-(2-fluoro-5-chlorobenzyl)-2,2',5'-trioxospiro[indole-3,3'-pyrrolidin]-1(2H)-yl]acetic acid | ABS | 95.8 (retention time chiral HPLC 6.27 min) | 451.3 (ESI+) 449.3 (ESI−) |
| 108 | (3R)-[5-chloro-1'-(2-fluoro-5-chlorobenzyl)-2,2',5'-trioxospiro[indole-3,3'-pyrrolidin]-1(2H)-yl]acetic acid | ABS | 98.2 (retention time chiral HPLC 6.68) | 451.3 (ESI+) 449.3 (ESI−) |

Example 109

[5'-chloro-1-(5-chloro-2-fluorobenzyl)-2,2',5-trioxospiro[imidazolidine-4,3'-indol]-1'(2'H)-yl]acetic acid

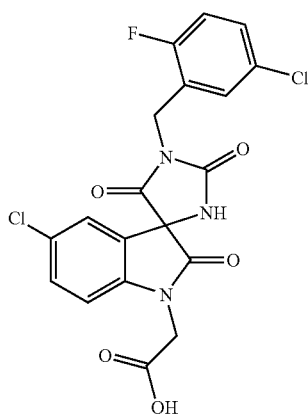

An ice-cold solution of tert-butyl [5'-chloro-1-(5-chloro-2-fluorobenzyl)-2,2',5-trioxospiro[imidazolidine-4,3'-indol]-1'(2'H)-yl]acetate (168.00 mg; 0.33 mmol) in DCM (4.00 ml) was treated with trifluoroacetic acid (1.00 ml). After stirring for 4 hours the reaction the solvents were evaporated. Toluene was added twice and evaporated to give the titla compound as a beige solid in 67.5% yield (96.1% purity by HPLC). MS (ESI$^+$): 452.1; MS (ESI$^−$): 454.4

Examples 110-112

Following the general methods as outlined in Example 109, the following compounds were also prepared starting from the appropriate intermediates:

| Example | Name | Structure | HPLC purity (%) | MS |
|---|---|---|---|---|
| 110 | [5'-chloro-1-[(5-methyl-3-phenylisoxazol-4-yl)methyl]-2,2',5-trioxospiro[imidazolidine-4,3'-indol]-1'(2'H)-yl]acetic acid | 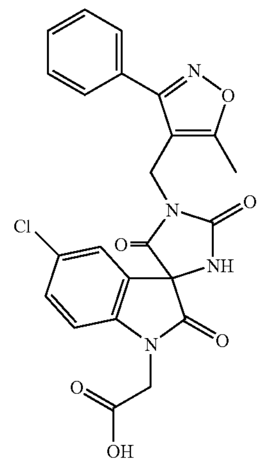 | 96.3 | 481.2 (ESI+) 479.9 (ESI−) |
| 111 | (1-benzyl-5'-chloro-2,2',5-trioxospiro[imidazolidine-4,3'-indol]-1'(2'H)-yl)acetic acid | 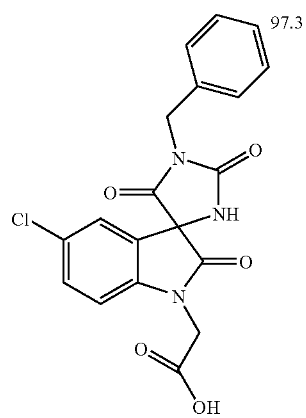 | 97.3 | 400 (ESI+) 398 (ESI−) |
| 112 | [5'-chloro-1-[(2-fluorobenzyl)-2,2',5-trioxospiro[imidazolidine-4,3'-indol]-1'(2'H)-yl]acetic acid | 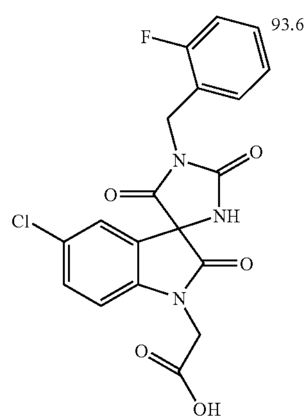 | 93.6 | 417.9 (ESI+) 416.1 (ESI−) |

Example 113

[5-chloro-1'-fluorobenzyl-2,5'-dioxospiro[indole-3,3'-pyrrolidin]-1(2H)-yl]acetic acid

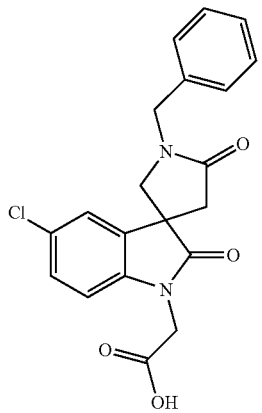

An ice-cold solution of tert-butyl [5-chloro-1'-(5-chloro-2-fluorobenzyl)-2,5'-dioxospiro[indole-3,3'-pyrrolidin]-1(2H)-yl]acetate, intermediate 33 (110 mg; 0.25 mmol) in DCM (8.00 ml) was treated with trifluoroacetic acid (2.00 ml). After stirring at room temperature for 4 h, the solvents were removed in vacuo. Toluene was added twice and removed in vacuo to give the titla compound as a white solid in 95% yield (99.8% purity by HPLC). MS (ESI$^+$): 358.3; MS (ESI$^-$): 356.3

Examples 114-116

Following the general methods as outlined in Example 113, the following compounds were also prepared starting from the appropriate intermediate:

| Example | Name | Structure | HPLC purity (%) | MS |
|---|---|---|---|---|
| 114 | [5-chloro-1'-[(3-methyl-5-phenylisoxazol-4-yl)methyl]-2,5'-dioxospiro[indole-3,3'-pyrrolidin]-1(2H)-yl]acetic acid | 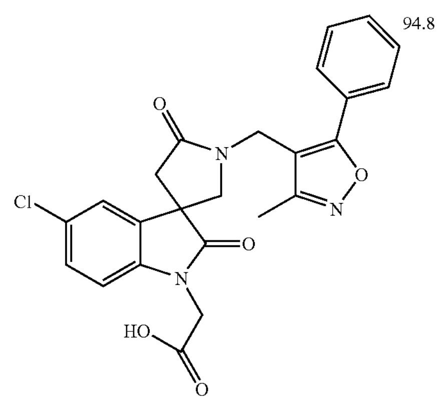 | 94.8 | 466.3 (ESI+) 464.5 (ESI−) |
| 115 | [5-chloro-1'-[(2-fluorobenzyl-2,5'-dioxospiro[indole-3,3'-pyrrolidin]-1(2H)-yl]acetic acid | 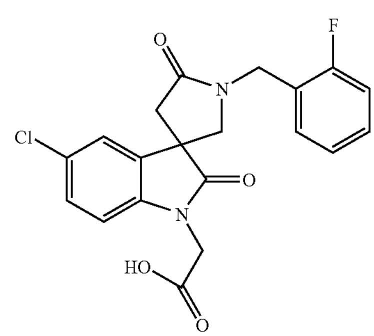 | 91.5 | 403.2 (ESI+) 401.0 (ESI−) |

| Example | Name | Structure | HPLC purity (%) | MS |
|---|---|---|---|---|
| 116 | [5-chloro-1'-(5-chloro-2-fluorobenzyl-2,5'-dioxospiro[indole-3,3'-pyrrolidin]-1(2H)-yl]acetic acid | 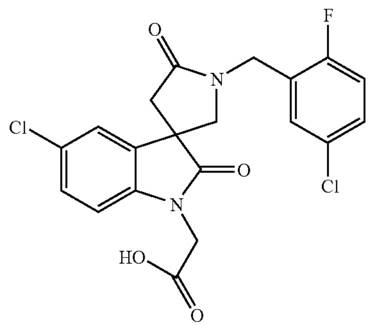 | 96.3 | 437.1 (ESI+)<br>435.1 (ESI−) |

Example 117

[5-chloro-1'-[(5-methyl-3-phenylisoxazol-4-yl)methyl]-2,2'-dioxospiro[indole-3,3'-pyrrolidin]-1(2H)-yl]acetic acid

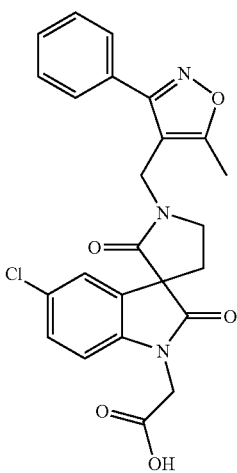

An ice-cold solution of tert-butyl [5-chloro-1'-[(5-methyl-3-phenylisoxazol-4-yl)methyl]-2,2'-dioxospiro[indole-3,3'-pyrrolidin]-1(2H)-yl]acetate, intermediate 42 (80.00 mg; 0.15 mmol) in DCM (8.00 ml) was treated with trifluoroacetic acid (2.00 ml). After stirring at room temperature for 5 h, the solvents were removed in vacuo. Toluene was added twice and removed in vacuo to give the titla compound as a white solid in 91% yield (96.3% purity by HPLC). MS (ESI+): 466.3; MS (ESI−): 464.4

Example 118

Preparation of a Pharmaceutical Formulation

The following formulation examples illustrate representative pharmaceutical compositions according to the present invention being not restricted thereto.

Formulation 1—Tablets

A spiro-indolinone of Formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active spiro-indolinone compound per tablet) in a tablet press.

Formulation 2—Capsules

A spiro-indolinone of Formula (I) is admixed as a dry powder with a starch diluent in an approximate 1:1 weight ratio. The mixture is filled into 250 mg capsules (125 mg of active spiro-indolinone compound per capsule).

Formulation 3—Liquid

A spiro-indolinone of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Tablets

A spiro-indolinone of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active spiro-indolinone compound) in a tablet press.

Formulation 5—Injection

A spiro-indolinone of Formula (I) is dissolved in a buffered sterile saline injectable aqueous medium to a concentration of approximately 5 mg/ml.

Biological Assays

Example 119

Construction of pCEP4-hCRTH2 Mammalian Expression Vector

Human CRTH2 cDNA was amplified by PCR using a human urinary bladder cDNA library as a template and specific primers containing HindIII and BamHI restriction sites for cloning into the pCEP4 vector (Invitrogen). The vector construction is described in detail in Sawyer et al., Br. J. Pharmocol 2002, 137, 1163-72. The nucleotide sequence of the cloned cDNA was identical the previously reported hCRTH2 sequence (Nagata et al, 1999, J. Immunol. 162, 1278-1286).

Example 120

Establishment of a pCEP4-hCRTH2-HEK293 (EBNA) Cell Line

HEK293 (EBNA) cells were transfected with the pCEP4-hCRTH2 construct using the calcium phosphate technique. Cells were maintained in culture at 37° C. in an atmosphere of 5% $CO_2$ in Dulbecco's modified Eagle's F12 medium (Invitrogen), containing 10% heat-inactivated foetal calf serum (TerraCell International, Canada), 2 mM Glutamine, 100 units/ml of penicillin and 100 µg/ml streptomycin (Invitrogen). 48 hours after the transfection, cells were grown in presence of 300 µg/ml of Hygromycin B (Invitrogen) for 4 weeks and antibiotic resistant cells were amplified for cell membrane preparation.

Example 121

Preparation of hCRTH2-Expressing Membranes

Adherent HEK293 (EBNA) cells expressing hCRTH2 were cultured in 225 cm² cell culture flasks (Corning, USA) in 30 ml of medium. After two rinses of phosphate buffered saline (PBS), cells were harvested in 10 ml of PBS containing 1 mM EDTA, centrifuged at 500×g for 5 min at 4° C. and frozen at −80° C. The pellet was re-suspended in 50 mM Tris-HCl, pH 7.4, 2 mM EDTA, 250 mM Sucrose, containing protease inhibitor cocktail tablets, (Complete EDTA-free, Roche, Germany) and incubated 30 min at 4° C. Cells were disrupted by nitrogen cavitation (Parr Instruments, USA) at 4° C. (800 p.s.i. for 30 min), and centrifuged at 500×g for 10 min at 4° C. Pellet containing nuclei and cellular debris was discarded and supernatant was centrifuged 60 min at 4° C. at 45000×g. Membrane pellet was re-suspended in storage buffer (10 mM HEPES/KOH pH 7.4, 1 mM EDTA, 250 mM sucrose, protease inhibitor cocktail tablets) using Dounce homogenization and frozen in liquid nitrogen, and stored at −80° C.

Example 122

Radioligand Binding Assay

The compounds of the present invention inhibit the binding of PGD2 to its receptor CRTH2. The inhibitory activity can be investigated by a radioligand binding assay (Sawyer et al., Br. J. Pharmacol 2002, 137, 1163-72). The radioligand binding assay was performed at room temperature in binding buffer (10 mM HEPES/KOH pH 7.4, mM $MnCl_2$, with protease inhibitor cocktail tablets), containing 1.5 nM [$^3$H]$PGD_2$ (Amersham, 156 Cie/mmol), and 10 µg of hCRTH2 HEK293 (EBNA) cell membrane protein in a final volume of 100 µl in 96 well plates (Corning, USA). Non-specific binding was determined in the presence of 1 µM $PGD_2$ (Cayman, USA). Competing spiro-indolinones were diluted in dimethylsulphoxide so that the total volume of dimethylsulfoxide was kept constant at 1% dimethylsulphoxide ($Me_2SO$) Serial dilutions of 100 µM and 100 µm were prepared. 10 µl each of these spiro-indolinone stock solutions were added. Incubation (60 min at room temperature) was terminated by rapid filtration through 96 wells hydrophobic GF/C Unifilter plates (Whatman, USA). Filters were washed twice with 250 µl of Tris-HCl pH 7.4, 10 mM MnCl2, and residual radioligand bound to the filters was mixed to 100 µl of liquid scintillation cocktail (Optiphase Supermix, Perkin Elmer, USA) and binding activity was determined by counting residual radioligand using a 1450 Micro-beta scintillation counter (Wallac, UK). The following representative compounds were tested. All inhibited the binding of PGD2 to CRTH2 by more than 70%.

(1'-benzyl-5-chloro-2,2',5'-trioxospiro[indole-3,3'-pyrrolidin]-1(2H)-yl)acetic acid (1'-benzyl-5-fluoro-2,2',5'-trioxospiro[indole-3,3'-pyrrolidin]-1(2H)-yl)acetic acid 4-(1'-allyl-5-chloro-2,2',5'-trioxospiro[indole-3,3'-pyrrolidin]-1(2H)-yl)butanoic acid

[5-chloro-1'-(2-methoxyethyl)-2,2',5'-trioxospiro[indole-3, 3'-pyrrolidin]-1(2H)-yl]acetic acid 4-(1'-benzyl-5-chloro-2,2',5'-trioxospiro[indole-3,3'-pyrrolidin]-1(2H)-yl)butanoic acid (1'-benzyl-5-methoxy-2,2',5'-trioxospiro[indole-3,3'-pyrrolidin]-1(2H)-yl)acetic acid

[5-fluoro-1'-[(2-methoxyethoxy)methyl]-2,2',5'-trioxospiro[indole-3,3'-pyrrolidin]-1(2H)-yl]acetic acid 4-(1'-allyl-5-fluoro-2,2',5'-trioxospiro[indole-3,3'-pyrrolidin]-1(2H)-yl)butanoic acid 4-(1'-benzyl-5-fluoro-2,2',5'-trioxospiro[indole-3,3'-pyrrolidin]-1(2H)-yl)butanoic acid

Example 123

Determination of K, (Radioligand Binding Assay)

$K_i$ values were determined by equilibrium competition binding experiments against [$^3$H]$PGD_2$. $K_i$ values were calculated from the formula below and represent the average of at least three independent dose response experiments. The $K_i$ values give the ligand concentrations necessary to inhibit 50% of the binding of [$^3$H]$PGD_2$ to CRTH2.

$$K_i = IC_{50}/(1+[\text{Concentration of Ligand}]/K_d)]$$

All experiments were performed in 96 well plates, in a final volume of 100 µl according to the above described filtration assay. The concentration of membranes and 3 [H]$PGD_2$, as well as the positive and negative controls were identical to the conditions described above.

In one embodiment, the Spiro derivatives of the present invention inhibit CRTH2 at a concentration of <10 µM. In another embodiment, the spiro derivatives of the present invention inhibit CRTH2 at a concentration of <1 µM. In a preferred embodiment, the spiro-indolinone of the present invention inhibit CRTH2 at a concentration of <0.1 µM.

$K_i$ values of representative compounds are shown in Table 1. It can be derived that said compounds according to Formula (I) showed a significant inhibition of the binding of PGD2 to CRTH2.

TABLE 1

| Compound No. | Name | $K_i$ (nM) |
|---|---|---|
| 1 | [5-chloro-1'-[(2-methyl-1,3-thiazol-4-yl)methyl]-2,2',5'-trioxospiro[indole-3,3'-pyrrolidin]-1(2H)-yl]acetic acid | 39 |
| 3 | [5-chloro-2,2',5'-trioxo-1'-(quinolin-2-ylmethyl)spiro[indole-3,3'-pyrrolidin]-1(2H)-yl]acetic acid | 93 |

TABLE 1-continued

| Compound No. | Name | $K_i$ (nM) |
|---|---|---|
| 4 | [5-chloro-1'-(4-cyanobenzyl)-2,2',5'-trioxospiro[indole-3,3'-pyrrolidin]-1(2H)-yl]acetic acid | 89 |
| 5 | [5-chloro-1'-(3-chlorobenzyl)-2,2',5'-trioxospiro[indole-3,3'-pyrrolidin]-1(2H)-yl]acetic acid | 73 |
| 6 | [5-chloro-1'-(3,4-dichlorobenzyl)-2,2',5'-trioxospiro[indole-3,3'-pyrrolidin]-1(2H)-yl]acetic acid | 100 |
| 10 | [5-chloro-2,2',5'-trioxo-1'-(3-phenoxybenzyl)spiro[indole-3,3'-pyrrolidin]-1(2H)-yl]acetic acid | 148 |
| 16 | [5-chloro-1'-(2,3-dihydro-1,4-benzodioxin-2-ylmethyl)-2,2',5'-trioxospiro[indole-3,3'-pyrrolidin]-1(2H)-yl]acetic acid | 213 |
| 17 | [5-chloro-2,2',5'-trioxo-1'-(pyridin-2-ylmethyl)spiro[indole-3,3'-pyrrolidin]-1(2H)-yl]acetic acid | 170 |
| 18 | [5-chloro-2,2',5'-trioxo-1'-{[5-(trifluoromethyl)-2-furyl]methyl}spiro[indole-3,3'-pyrrolidin]-1(2H)-yl]acetic acid | 270 |
| 23 | [5-chloro-2,2',5'-trioxo-1'-(2-phenylethyl)spiro[indole-3,3'-pyrrolidin]-1(2H)yl]acetic acid | 267 |
| 24 | [5-chloro-1'-(imidazo[1,2-a]pyridin-2-ylmethyl)-2,2',5'-trioxospiro[indole-3,3'-pyrrolidin]-1(2H)-yl]acetic acid | 705 |
| 25 | [5-chloro-2,2',5'-trioxo-1'-[(2E)-3-phenylprop-2-en-1-yl]spiro[indole-3,3'-pyrrolidin]-1(2H)-yl]acetic acid | 768 |
| 28 | [5-chloro-1'-(2-ethoxyethyl)-2,2',5'-trioxospiro[indole-3,3'-pyrrolidin]-1(2H)-yl]acetic acid | 1031 |
| 29 | [1'-[2-(benzyloxy)ethyl]-5-chloro-2,2',5'-trioxospiro[indole-3,3'-pyrrolidin]-1(2H)-yl]acetic acid | 1129 |
| 32 | [5-chloro-1'-[(1-methyl-1H-imidazol-2-yl)methyl]-2,2',5'-trioxospiro[indole-3,3'-pyrrolidin]-1(2H)-yl]acetic acid | 1817 |
| 35 | 4-[5-chloro-2,2',5'-trioxo-1'-[4-trifluoromethyl)benzyl]spiro[indole-3,3'-pyrrolidin]-1(2H)-yl]butanoic acid | 681 |
| 54 | [5-chloro-1'-(2-methoxybenzyl)2,2',5'-trioxospiro[indole-3,3'-pyrrolidin]-1(2H)-yl]acetic acid | 153 |
| 75 | [5-chloro-1'-[(4-methoxy-3,5-dimethylpyridin-2-yl)methyl]-2,2',5'-trioxospiro[indole-3,3'-pyrrolidin]-1(2H)-yl]acetic acid | 510 |
| 76 | [5-chloro-1'-[(4,6-dichloropyridin-3-yl)methyl]-2,2',5'-trioxospiro[indole-3,3'-pyrrolidin]-1(2H)-yl]acetic acid | 12 |
| 77 | [5-chloro-2,2',5'-trioxo-1'-(2-thienylmethyl)spiro[indole-3,3'-pyrrolidin]-1(2H)-yl]acetic acid | 75 |
| 78 | [5-chloro-1'-[(3,4-dimethoxypyridin-2-yl)methyl]-2,2',5'-trioxospiro[indole-3,3'-pyrrolidin]-1(2H)-yl]acetic acid | 101 |
| 103 | [5-chloro-1'-{[2-(3-chlorophenyl)1,3-thiazol-4-yl]methyl}-2,2',5'-trioxospiro[indole-3,3'-pyrrolidin]-1(2H)-yl]acetic acid | 6 |
| 104 | [5-chloro-1'-(2-fluorobenzyl)-2,2',5'-trioxospiro[indole-3,3'-pyrrolidin]-1(2H)-yl]acetic acid | 24 |
| 105 | [5'-chloro-1-(5-chloro-2-fluorobenzyl)-2,2',5-trioxospiro[imidazolidine-4,3'-indol]-1'(2'H)-yl]acetic acid | 16 |
| 106 | [5'-chloro-1-[(5-methyl-3-phenylisoxazol-4-yl)methyl]-2,2',5-trioxospiro[imidazolidine-4,3'-indol]-1'(2'H)-yl]acetic acid | 1120 |
| 107 | (1-benzyl-5'-chloro-2,2',5-trioxospiro[imidazolidine-4,3'-indol]-1'(2'H)-yl)acetic acid | 300 |
| 108 | [5'-chloro-1-(2-fluorobenzyl)-2,2',5-trioxospiro[imidazolidine-4,3'-indol]-1'(2'H)-yl]acetic acid | 4.8 |
| 109 | (3R)-[5-chloro-1'-(2-fluorobenzyl)-2,2',5'-trioxospiro[indole-3,3'-pyrrolidin]-1(2H)-yl]acetic acid | 28 |
| 110 | (3S)-[5-chloro-1'-(2-fluorobenzyl)-2,2',5'-trioxospiro[indole-3,3'-pyrrolidin]-1(2H)-yl]acetic acid | 8.4 |
| 111 | (3S)-[5-chloro-1'-(2-fluoro-5-chlorobenzyl)-2,2',5'-trioxospiro[indole-3,3'-pyrrolidin]-1(2H)-yl]acetic acid | 470 |
| 112 | (3R)-[5-chloro-1'-(2-fluoro-5-chlorobenzyl)-2,2',5'-trioxospiro[indole-3,3'-pyrrolidin]-1(2H)-yl]acetic acid | 150 |
| 113 | (1'-benzyl-5-chloro-2,5'-dioxospiro[indole-3,3'-pyrrolidin]-1(2H)-yl)acetic acid | 630 |
| 114 | [5-chloro-1'-[(3-methyl-5-phenylisoxazol-4-yl)methyl]-2,5'-dioxospiro[indole-3,3'-pyrrolidin]-1(2H)-yl]acetic acid | 3.4 |
| 115 | [5-chloro-1'-(2-fluorobenzyl)-2,5'-dioxospiro[indole-3,3'-pyrrolidin]-1(2H)-yl]acetic acid | 140 |
| 116 | [5-chloro-1'-(5-chloro-2-fluorobenzyl)-2,5'-dioxospiro[indole-3,3'-pyrrolidin]-1(2H)-yl]acetic acid | 22 |

Example 124

[$^{35}$S]GTPγS Binding Assay

The [$^{35}$S]GTPγS assay measures the increase in guanine nucleotide exchange at G-proteins in cell membranes, resulting from agonist (PGD2) binding to CRTH2. This process can be monitored in vitro by incubating cell membranes containing G-proteins and CRTH2 with GDP and [$^{35}$S]GTPγS, a radiolabeled, hydrolysis-resistant analogue of GTP (see, Harrison et al., Life Sciences 74, 489-508, 2003). The addition of a spiro-indolinone results in binding to CRTH2 and thus in an inhibition of agonist binding, which can be monitered as inhibition of the stimulation of GTP/GDP exchange.

Assay conditions were identical to conditions of radioligand binding assay as described in Example 21. The [$^{35}$S] GTPγS binding assay was performed at 30° C. with gentle agitation in 96-well scintillating white polystyrene plates (Perkin Elmer, USA), in a final volume of 200 μl, containing 2% of dimethylsulphoxide (Me$_2$SO). The spiro derivatives were incubated in 20 mM HEPES/KOH pH 7.4, 10 mM MgCl$_2$, 10 μg/ml Saponin, 3 μM GDP, 150 mM NaCl containing 10 μg of membranes expressing the hCRTH2 receptor (Euroscreen, Belgium) for 10 min. Non-specific binding was determined in the presence of 10 μM of GTPγS. Samples were incubated for 30 min in the presence of increasing concentrations of PGD$_2$ for the determination of agonist activity, or with 80 nM of PGD$_2$ for determination of antagonist activity, respectively. 0.15 nM of [$^{35}$S]GTPγS were subsequently added to each sample and after incubation of 30 min reactions were stopped by centrifugation at 1000×g, at 4° C. for 10 min.

Supernatant was removed and [$^{35}$S]GTPγS binding was determined using a 1450 Micro-beta scintillation counter. Data were analysed using "Prism" (GraphPad Software, Inc. San Diego, USA). The determination of the IC$_{50}$ values (i.e. the amount necessary to achieve 50% inhibition of binding (in μM)) were performed in 96 well plates, in a final volume of 100 μl according to the above described filtration assay. The concentration of membranes and radioactive ligand, as well as the positive and negative controls were identical to the conditions used and described above Examples 122 and 123.

IC$_{50}$ values of representative compounds are shown in Table 2. It can be derived that said compounds according to Formula (I) showed a significant inhibition of the binding of PGD2 to CRTH2.

TABLE 2

| Compound No. | Name | K$_i$ (nM) |
|---|---|---|
| 1 | [5-chloro-1'-[(2-methyl-1,3-thiazol-4-yl)methyl]-2,2',5'-trioxospiro[indole-3,3'-pyrrolidin]-1(2H)-yl]acetic acid | 198 |
| 2 | [5-chloro-1'-(2,4-dichlorobenzyl)-2,2',5'-trioxospiro[indole-3,3'-pyrrolidin]-1(2H)-yl]acetic acid | 80 |
| 3 | [5-chloro-2,2',5'-trioxo-1'-(quinolin-2-ylmethyl)spiro[indole-3,3'-pyrrolidin]-1(2H)-yl]acetic acid | 200 |
| 4 | [5-chloro-1'-(4-cyanobenzyl)-2,2',5'-trioxospiro[indole-3,3'-pyrrolidin]-1(2H)-yl]acetic acid | 305 |
| 5 | [5-chloro-1'-(3-chlorobenzyl)-2,2',5'-trioxospiro[indole-3,3'-pyrrolidin]-1(2H)-yl]acetic acid | 90 |
| 10 | [5-chloro-2,2',5'-trioxo-1'-(3-phenoxybenzyl)spiro[indole-3,3'-pyrrolidin]-1(2H)-yl]acetic acid | 95 |
| 16 | [5-chloro-1'-(2,3-dihydro-1,4-benzodioxin-2-ylmethyl)-2,2',5'-trioxospiro[indole-3,3'-pyrrolidin]-1(2H)-yl]acetic acid | 370 |
| 17 | [5-chloro-2,2',5'-trioxo-1'-(pyridin-2-ylmethyl)spiro[indole-3,3'-pyrrolidin]-1(2H)-yl]acetic acid | 980 |
| 18 | [5-chloro-2,2',5'-trioxo-1'-{[5-(trifluoromethyl)-2-furyl]methyl}spiro[indole-3,3'-pyrrolidin]-1(2H)-yl]acetic acid | 420 |
| 76 | [5-chloro-1'-[(4,6-dichloropyridin-3-yl)methyl]-2,2',5'-trioxospiro[indole-3,3'-pyrrolidin]-1(2H)-yl]acetic acid | 1300 |
| 103 | [5-chloro-1'-{[2-(3-chlorophenyl)-1,3-thiazol-4-yl]methyl}-2,2',5'-trioxospiro[indole-3,3'-pyrrolidin]-1(2H)-yl]acetic acid | 46 |
| 104 | [5-chloro-1'-(2-fluorobenzyl)-2,2',5'-trioxospiro[indole-3,3'-pyrrolidin]-1(2H)-yl]acetic acid | 190 |
| 107 | (1-benzyl-5'-chloro-2,2',5-trioxospiro[imidazolidine-4,3'-indol]-1'(2'H)-yl)acetic acid | 72 |

Example 125

CHS Model

The contact hypersensitivity model can be used to evaluate the therapeutic efficacy of spiro derivatives on skin inflammation mediated by T cells. The model is well established for characterization of compound for dermatological indications like psoriasis and allergic contact dermatitis (Xu et al. J Exp Med. 183, 1001-12, 1996). It involves a sensitization phase and a subsequent challenge with an antigen (DNFB, 2,4-dinitrofluorbenzene). This results in skin inflammation with formation of edema and cellular infiltrates in the skin. The edema can be measured by caliper at the challenged site (ear of the mice). Intravenous or oral administration with 10% Labrasol as vehicle of the compounds of the invention 30 min before challenge with DNFB results in a decrease of the swelling and therefore reduces inflammation in the skin compared to positive controls treated with vehicle only before challenge with the antigen. Negative control mice are not sensitized, but challenged with DNFB, therefore no T cell dependent inflammation occurs and no edema is formed. Balb/c mice were obtained from CharlesRiver (Calcco, Italy). Animals were housed in a conventional animal facility. Treatment started at an average age of 8-12 weeks. DNFB (2,4-dinitrofluorbenzene) was purchased from Sigma-Aldrich (St. Louis, Mo. USA).

Sensitization and Challenge of CHS by DNFB

Mice were sensitized and challenged to elicit CHS to DNFB. The sensitization phase was followed by a challenge phase. DNFB was diluted in acetone/olive oil (4/1) immediately before use. Mice were sensitized to DNFB by applying 25 ml of 0.5% DNFB solution onto the shaved dorsal skin. Five days later, 10 µl of 0.2% DNFB were applied onto both sides of the right ear (challenge). Ear thickness was monitored on day 6 (1 day after challenge) using a caliper (Mitutoyo, Milan, Italy). Ear swelling was calculated as ((Tn−T5) right ear−(Tn−T5)left ear), wherein Tn and T5 represent values of ear thickness at day n of investigation and day 5 prior to challenge, respectively.

Results for two representative compounds are given below.

Compound 83 (administration of 60 mg/kg; po) caused a reduction in ear swelling of 40%.

Compound 105 (administration of 60 mg/kg; po) caused a reduction in ear swelling of 55%.

Example 126

Model of DK-PGD2-Induced Vascular Leakage in Mice

This test is described in Takeshita et al. (2004). Balb/c mice (Elevage Janvier) (8 week old) received an intradermal injection of DK-PGD$_2$ (10 µg in 30 µl) on their shaved backs and an intravenous injection of Evans blue solution (25 mg/kg) 30 min after administration of the test molecules (spiro derivative). Ninety minutes after the challenge, the animals were sacrificed. The skin of the back was removed and blood was sampled. The extravasated dye (punch diameter: 5 mm) was extracted by 0.2 ml of formamide and was quantified by fluorescence (E1: 585 nm, E2: 660 nm). The Evans Blue extravasation ratio was expressed as the following: skin/serum×1000.

Inhibition percentages of vascular leakage for representative compounds (at a dose of 30 mg/kg) are shown in Table 3.

TABLE 3

| Compound No. | Inhibition (%) |
|---|---|
| 83 | 77 |
| 105 | 60 |
| 109 | 38 |
| 111 | 65 |
| 112 | 61 |
| 113 | 55 |
| 114 | 44 |
| 115 | 45 |
| 116 | 51 |

REFERENCE LIST

Cosmi et al. (2000) Eur. J. Immunol. 30, 2972-2979
Bush, R. K., Georgitis J. W., Handbook of asthma and rhinitis. 1st ed. (1997), Abingdon: Blackwell Science. 270
Harrison et al. (2003) Life Sciences 74, 489-508
Hirai et al. (2001) J. Exp. Med. 193, 255-261
Lewis et al. (1982) J. Immunol. 129, 1627
Matsuoka et al. (2000) Science 287, 2013-2017
Nagata et al. (1999) J. Immunol. 162, 1278-1286
Sawyer et al. (2002) Br. J. Pharmacol. 137, 1163-1172
Takeshita et al (2004) International Immunol, 16, 947-959.
Woodward et al. (1990) Invest. Ophthalomol. Vis. Sci. 31, 138-146
Woodward et al. (1993) Eur. J. Pharmacol. 230, 327-333
Xu et al. (1996) J Exp Med. 183, 1001-12
WO 04/106302
WO 04/096777
WO 04/035543
WO 04/032848
WO 05/007094
WO 04/108692
WO 04/108717
WO 05/102338

The invention claimed is:

1. A compound according to Formula (I')

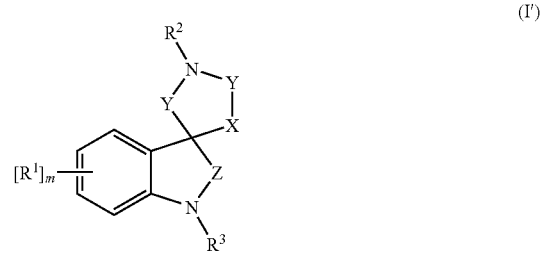

wherein:

$R^1$ is selected from the group consisting of hydrogen, $C_1$-$C_6$-alkyl, $C_1$-$C_6$-alkoxy, halo-$C_1$-$C_6$-alkyl, halo-$C_1$-$C_6$-alkoxy, halogen, aryl and heteroaryl;

m is an integer selected from 0, 1, 2, 3 or 4;

$R^2$ is either $C_3$-$C_6$-alkyl or A; wherein

A is selected from the group consisting of A1, A2, A3, A4, A5 and A6:

A1

A2

A3

A4

A5

A6 with each n being an integer independently selected from 1, 2, 3 or 4; wherein $R^4$ is selected from the group consisting of $C_2$-$C_6$ alkyl, $C_2$-$C_6$ alkenyl, $C_3$-$C_8$-cycloalkyl, $C_3$-$C_8$-heterocycloalkyl, aryl and heteroaryl;

each $R^4$ may optionally be substituted independently with one or more groups $R^6$;

each $R^6$ is independently selected from the group consisting of $C_1$-$C_6$-alkyl, alkoxy, alkoxycarbonyl, aryl, aryl $C_1$-$C_6$-alkyl, heteroaryl, substituted or unsubstituted heteroaryl $C_1$-$C_6$-alkyl, $C_3$-$C_8$-cycloalkyl, $C_3$-$C_8$-heterocycloalkyl, carboxyl, cyano, halogen, hydroxy, amino, aminocarbonyl, acylamino, nitro, sulfoxy, sulfonyl, sulfonylamine, aminosulfonyl and trihalo-$C_1$-$C_6$-alkyl;

$R^7$ is either hydrogen or $C_1$-$C_6$-alkyl;

$R^3$ is B, wherein

B is:

←(CH$_2$)$n$-R$^5$ with n being an integer independently selected from 1, 2, 3 or 4; wherein
R$^5$ is carboxy;
X is either CH$_2$ or NH;
each Y is independently either C(O) or CH$_2$; and
z is either C(O) or CHR$^7$;
as well as its geometrical isomers, optically active forms as enantiomers, diastereomers, its racemate forms, or pharmaceutically acceptable salts thereof.

2. The compounds according to claim 1, wherein R$^1$ is either halogen or halo-C$_1$-C$_6$-alkoxy.

3. The compound according to claim 2, wherein R$^1$ is halogen and m is either 1 or 2.

4. The compound according to claim 1, wherein R$^2$ is A1, and n is 1.

5. The compound according to claim 1, wherein X is CH.

6. The compound according to claim 1, wherein X is NH.

7. The compound according to claim 1, wherein Z is C(O).

8. A compound selecting from the group consisting of:
[5-chloro-1'-[(2-methyl-1,3-thiazol-4-yl)methyl]-2,2',5'-trioxospiro[indole-3,3'-pyrrolidin]-1(2H)-yl]acetic acid,
[5-chloro-1'-(2,4-dichlorobenzyl)-2,2',5'-trioxospiro[indole-3,3'-pyrrolidin]-1(2H)-yl]acetic acid,
[5-chloro-2,2',5'-trioxo-1'-(quinolin-2-ylmethyl)spiro[indole-3,3'-pyrrolidin]-1(2H)-yl]acetic acid,
[5-chloro-1'-(4-cyanobenzyl)-2,2',5'-trioxospiro[indole-3,3'-pyrrolidin]-1(2H)-yl]acetic acid,
[5-chloro-1'-(3-chlorobenzyl)-2,2',5'-trioxospiro[indole-3,3'-pyrrolidin]-1(2H)-yl]acetic acid,
[5-chloro-1'-(3,4-dichlorobenzyl)-2,2',5'-trioxospiro[indole-3,3'-pyrrolidin]-1(2H)-yl]acetic acid,
[5-chloro-1'-(2-fluorobenzyl)-2,2',5'-trioxospiro[indole-3,3'-pyrrolidin]-1(2H)-yl]acetic acid,
[5-chloro-1'-(4-fluorobenzyl)-2,2',5'-trioxospiro[indole-3,3'-pyrrolidin]-1(2H)-yl]acetic acid,
[5-chloro-1'-(1-naphthylmethyl)-2,2',5'-trioxospiro[indole-3,3'-pyrrolidin]-1(2H)-yl]acetic acid,
[5-chloro-2,2',5'-trioxo-1'-(3-phenoxybenzyl)spiro[indole-3,3'-pyrrolidin]-1(2H)-yl]acetic acid,
[5-chloro-1'-(3-fluorobenzyl)-2,2',5'-trioxospiro[indole-3,3'-pyrrolidin]-1(2H)-yl]acetic acid,
[5-chloro-1'-(4-chlorobenzyl)-2,2',5'-trioxospiro[indole-3,3'-pyrrolidin]-1(2H)-yl]acetic acid,
[5-chloro-1'-(4-methoxybenzyl)-2,2',5'-trioxospiro[indole-3,3'-pyrrolidin]-1(2H)-yl]acetic acid,
[5-chloro-1'-(3-methoxybenzyl)-2,2',5'-trioxospiro[indole-3,3'-pyrrolidin]-1(2H)-yl]acetic acid,
[5-chloro-1'-(2,3-dihydro-1,4-benzodioxin-2-ylmethyl)-2,2',5'-trioxospiro[indole-3,3'-pyrrolidin]-1(2H)-yl]acetic acid,
[5-chloro-2,2',5'-trioxo-1'-(pyridin-2-ylmethyl)spiro[indole-3,3'-pyrrolidin]-1(2H)-yl]acetic acid,
[5-chloro-2,2',5'-trioxo-1'-{[5-(trifluoromethyl)-2-furyl]methyl}spiro [indole-3,3'-pyrrolidin]-1(2H)-yl]acetic acid,
[5-chloro-1'-(4-methylbenzyl)-2,2',5'-trioxospiro[indole-3,3'-pyrrolidin]-1(2H)-yl]acetic acid,
[5-chloro-2,2',5'-trioxo-1'-[3-(trifluoromethyl)benzyl]spiro[indole-3,3'-pyrrolidin]-1(2H)-yl]acetic acid,
[5-chloro-1'-(2-naphthylmethyl)-2,2',5'-trioxospiro[indole-3,3'-pyrrolidin]-1(2H)-yl]acetic acid,
[5-chloro-2,2',5'-trioxo-1'-(1-phenylethyl)spiro[indole-3,3'-pyrrolidin]-1(2H)-yl]acetic acid,
[5-chloro-2,2',5'-trioxo-1'-(2-phenylethyl)spiro[indole-3,3'-pyrrolidin]-1(2H)-yl]acetic acid,
[5-chloro-1'-(imidazo[1,2-a]pyridin-2-ylmethyl)-2,2',5'-trioxospiro[indole-3,3'-pyrrolidin]-1(2H)-yl]acetic acid,
[5-chloro-2,2',5'-trioxo-1'-[(2E)-3-phenylprop-2-en-1-yl]spiro[indole-3,3'-pyrrolidin]-1(2H)-yl]acetic acid,
[5-chloro-2,2',5'-trioxo-1'-[4-(trifluoromethyl)benzyl]spiro[indole-3,3'-pyrrolidin]-1(2H)-yl]acetic acid,
4-(1'-benzyl-6-chloro-2,2',5'-trioxospiro[indole-3,3'-pyrrolidin]-1(2H)-yl)butanoic acid,
[5-chloro-1'-(2-ethoxyethyl)-2,2',5'-trioxospiro[indole-3,3'-pyrrolidin]-1(2H)-yl]acetic acid,
[1'-[2-(benzyloxy)ethyl]-5-chloro-2,2',5'-trioxospiro[indole-3,3'-pyrrolidin]-1(2H)-yl]acetic acid,
[5-chloro-2,2',5'-trioxo-1'-(2-phenoxyethyl)spiro[indole-3,3'-pyrrolidin]-1(2H)-yl]acetic acid,
[5-chloro-2,2',5'-trioxo-1'-(3-phenylprop-2-yn-1-yl)spiro[indole-3,3'-pyrrolidin]-1(2H)-yl]acetic acid,
(1'-but-2-yn-1-yl-5-chloro-2,2',5'-trioxospiro[indole-3,3'-pyrrolidin]-1(2H)-yl)acetic acid,
[5-chloro-1'-[(1-methyl-1H-imidazol-2-yl)methyl]-2,2',5'-trioxospiro[indole-3,3'-pyrrolidin]-1(2H)-yl]acetic acid,
4-[5-chloro-1'-(4-fluorobenzyl)-2,2',5'-trioxospiro[indole-3,3'-pyrrolidin]-1(2H)-yl]butanoic acid,
4-[5-chloro-1'-(4-chlorobenzyl)-2,2',5'-trioxospiro[indole-3,3'-pyrrolidin]-1(2H)-yl]butanoic acid,
4-[5-chloro-2,2',5'-trioxo-1'-[4-(trifluoromethyl)benzyl]spiro[indole-3,3'-pyrrolidin]-1(2H)-yl]butanoic acid,
[1'-benzyl-2,2',5'-trioxo-5-(trifluoromethoxy)spiro[indole-3,3'-pyrrolidin]-1(2H)-yl]acetic acid,
[1'-(4-methoxybenzyl)-2,2',5'-trioxo-5-(trifluoromethoxy)spiro[indole-3,3'-pyrrolidin]-1(2H)-yl]acetic acid,
[1'43-fluorobenzyl)-2,2',5'-trioxo-5-(trifluoromethoxy)spiro[indole-3,3'-pyrrolidin]-1(2H)-yl]acetic acid,
[1'-(2-fluorobenzyl)-2,2',5'-trioxo-5-(trifluoromethoxy)spiro[indole-3,3'-pyrrolidin]-1(2H)-yl]acetic acid,
[2,2',5'-trioxo-5-(trifluoromethoxy)-1'-[3-(trifluoromethyl)benzyl]spiro[indole-3,3'-pyrrolidin]-1(2H)-yl]acetic acid,
[1'-(1-naphthylmethyl)-2,2',5'-trioxo-5-(trifluoromethoxy)spiro[indole-3,3'-pyrrolidin]-1(2H)-yl]acetic acid,
[1'-(4-chlorobenzyl)-2,2',5'-trioxo-5-(trifluoromethoxy)spiro[indole-3,3'-pyrrolidin]-1(2H)-yl]acetic acid,
[1'-(4-fluorobenzyl)-2,2',5'-trioxo-5-(trifluoromethoxy)spiro[indole-3,3'-pyrrolidin]-1(2H)-yl]acetic acid,
4-[5-chloro-1'-(4-methoxybenzyl)-2,2',5'-trioxospiro[indole-3,3'-pyrrolidin]-1(2H)-yl]butanoic acid,
4-[5-chloro-1'-(2-fluorobenzyl)-2,2',5'-trioxospiro[indole-3,3'-pyrrolidin]-1(2H)-yl]butanoic acid,
4-[5-chloro-1'-(2-fluorobenzyl)-2,2',5'-trioxospiro[indole-3,3'-pyrrolidin]-1(2H)-yl]butanoic acid,
[(3S)-1'-benzyl-5-chloro-2,2',5'-trioxospiro[indole-3,3'-pyrrolidin]-1(2H)-yl]acetic acid,
[(3R)-1'-benzyl-5-chloro-2,2',5'-trioxospiro[indole-3,3'-pyrrolidin]-1(2H)-yl]acetic acid,
[6-chloro-1'-(2-fluorobenzyl)-2,2',5'-trioxospiro[indole-3,3'-pyrrolidin]-1(2H)-yl]acetic acid,
[6-chloro-1'-(3-fluorobenzyl)-2,2',5'-trioxospiro[indole-3,3'-pyrrolidin]-1(2H)-yl]acetic acid,
[6-chloro-1'-(4-fluorobenzyl)-2,2',5'-trioxospiro[indole-3,3'-pyrrolidin]-1(2H)-yl]acetic acid,
4-[5-chloro-2,2',5'-trioxo-1'-(2-phenylethyl)spiro[indole-3,3'-pyrrolidin]-1(2H)-yl]butanoic acid,

[5-chloro-1'-(3,5-dichlorobenzyl)-2,2',5'-trioxospiro[indole-3,3'-pyrrolidin]-1(2H)-yl]acetic acid,
[5-chloro-2,2',5'-trioxo-1'-(4-phenoxybenzyl)spiro[indole-3,3'-pyrrolidin]-1(2H)-yl]acetic acid,
[5-chloro-1'-(2-methoxybenzyl)-2,2',5'-trioxospiro[indole-3,3'-pyrrolidin]-1(2H)-yl]acetic acid,
[5-chloro-1'-[4-(methylsulfonyl)benzyl]-2,2',5'-trioxospiro[indole-3,3'-pyrrolidin]-1(2H)-yl]acetic acid,
[1'-[4-(aminocarbonyl)benzyl]-5-chloro-2,2',5'-trioxospiro[indole-3,3'-pyrrolidin]-1(2H)-yl]acetic acid,
[5-chloro-1'-(3-cyanobenzyl)-2,2',5'-trioxospiro[indole-3,3'-pyrrolidin]-1(2H)-yl]acetic acid,
[5-chloro-1'-[(5-methylisoxazol-3-yl)methyl]-2,2',5'-trioxospiro[indole-3,3'-pyrrolidin]-1(2H)-yl]acetic acid,
[1'-(1,3-benzothiazol-2-ylmethyl)-5-chloro-2,2',5'-trioxospiro[indole-3,3'-pyrrolidin]-1(2H)-yl]acetic acid,
[5-chloro-1'-[(5-chloro-2-thienyl)methyl]-2,2',5'-trioxospiro[indole-3,3'-pyrrolidin]-1(2H)-yl]acetic acid,
[5-chloro-1'-[(5-chloro-1,2,4-thiadiazol-3-yl)methyl]-2,2',5'-trioxospiro[indole-3,3'-pyrrolidin]-1(2H)-yl]acetic acid,
[5-chloro-2,2',5'-trioxo-1'-[(2-phenyl-1,3-thiazol-4-yl)methyl]spiro[indole-3,3'-pyrrolidin]-1(2H)-yl]acetic acid,
[5-chloro-1'-(2-chloro-4-fluorobenzyl)-2,2',5'-trioxospiro[indole-3,3'-pyrrolidin]-1(2H)-yl]acetic acid,
[5-chloro-1'-(2,5-dichlorobenzyl)-2,2',5'-trioxospiro[indole-3,3'-pyrrolidin]-1(2H)-yl]acetic acid,
[1'-[4-(acetylamino)benzyl]-5-chloro-2,2',5'-trioxospiro[indole-3,3'-pyrrolidin]-1(2H)-yl]acetic acid,
[5-chloro-1'-[(6-chloropyridin-3-yl)methyl]-2,2',5'-trioxospiro[indole-3,3'-pyrrolidin]-1(2H)-yl]acetic acid,
[5-chloro-1'-(1H-indol-3-ylmethyl)-2,2',5'-trioxospiro[indole-3,3'-pyrrolidin]-1(2H)-yl]acetic acid,
[5-chloro-1'-(5-chloro-2-fluorobenzyl)-2,2',5'-trioxospiro[indole-3,3'-pyrrolidin]-1(2H)-yl]acetic acid,
[5-chloro-2,2',5'-trioxo-1'-(1,3-thiazol-4-ylmethyl)spiro[indole-3,3'-pyrrolidin]-1(2H)-yl]acetic acid,
[5-chloro-1'-[(4-chloropyridin-3-yl)methyl]-2,2',5'-trioxospiro[indole-3,3'-pyrrolidin]-1(2H)-yl]acetic acid,
[5-chloro-2,2',5'-trioxo-1'-(pyridin-3-ylmethyl)spiro[indole-3,3'-pyrrolidin]-1(2H)-yl]acetic acid,
[5-chloro-1'-[(3,5-dimethylisoxazol-4-yl)methyl]-2,2',5'-trioxospiro[indole-3,3'-pyrrolidin]-1(2H)-yl]acetic acid,
[1'-[(5-tert-butyl-1,2,4-oxadiazol-3-yl)methyl]-5-chloro-2,2',5'-trioxospiro[indole-3,3'-pyrrolidin]-1(2H)-yl]acetic acid,
[5-chloro-1'-[(5-cyclopropyl-1,3,4-thiadiazol-2-yl)methyl]-2,2',5'-trioxospiro[indole-3,3'-pyrrolidin]-1(2H)-yl]acetic acid,
[5-chloro-1'-[(4-methoxy-3,5-dimethylpyridin-2-yl)methyl]-2,2',5'-trioxospiro[indole-3,3'-pyrrolidin]-1(2H)-yl]acetic acid,
[5-chloro-1'-[(4,6-dichloropyridin-3-yl)methyl]-2,2',5'-trioxospiro[indole-3,3'-pyrrolidin]-1(2H)-yl]acetic acid,
[5-chloro-2,2',5'-trioxo-1'-(2-thienylmethyl)spiro[indole-3,3'-pyrrolidin]-1(2H)-yl]acetic acid,
[5-chloro-1'-[(3,4-dimethoxypyridin-2-yl)methyl]-2,2',5'-trioxospiro[indole-3,3'-pyrrolidin]-1(2H)-yl]acetic acid,
[5-chloro-1'-(isoquinolin-1-ylmethyl)-2,2',5'-trioxospiro[indole-3,3'-pyrrolidin]-1(2H)-yl]acetic acid,
[5-chloro-2,2',5'-trioxo-1'-[(5-phenyl-1,2,4-oxadiazol-3-yl)methyl]spiro[indole-3,3'-pyrrolidin]-1(2H)-yl]acetic acid,
(3R)-[5-chloro-1'-(3-chlorobenzyl)-2,2',5'-trioxospiro[indole-3,3'-pyrrolidin]-1(2H)-yl]acetic acid,
(3S)-[5-chloro-1'-(3-chlorobenzyl)-2,2',5'-trioxospiro[indole-3,3'-pyrrolidin]-1(2H)-yl]acetic acid,
(3R)-[5-chloro-1'-(3-methoxybenzyl)-2,2',5'-trioxospiro[indole-3,3'-pyrrolidin]-1(2H)-yl]acetic acid,
(3S)-[5-chloro-1'-(3-methoxybenzyl)-2,2',5'-trioxospiro[indole-3,3'-pyrrolidin]-1(2H)-yl]acetic acid,
[5-chloro-1'-(2,4-difluorobenzyl)-2,2',5'-trioxospiro[indole-3,3'-pyrrolidin]-1(2H)-yl]acetic acid,
[5-chloro-1'-(1,3-oxazol-2-ylmethyl)-2,2',5'-trioxospiro[indole-3,3'-pyrrolidin]-1(2H)-yl]acetic acid,
[5-chloro-1'-[(4-methoxy-3-methylpyridin-2-yl)methyl]-2,2',5'-trioxospiro[indole-3,3'-pyrrolidin]-1(2H)-yl]acetic acid,
[5-chloro-1'-{[2-(4-chlorophenyl)-1,3-thiazol-4-yl]methyl}-2,2',5'-trioxospiro[indole-3,3'-pyrrolidin]-1(2H)-yl]acetic acid,
[5-chloro-1'-{[5-(4-methoxyphenyl)-1,2,4-oxadiazol-3-yl]methyl}-2,2',5'-trioxospiro[indole-3,3'-pyrrolidin]-1(2H)-yl]acetic acid,
[5-chloro-1'-[(1-methyl-1H-1,2,3-benzotriazol-5-yl)methyl]-2,2',5'-trioxospiro[indole-3,3'-pyrrolidin]-1(2H)-yl]acetic acid,
[5-chloro-1'-(3-furylmethyl)-2,2',5'-trioxospiro[indole-3,3'-pyrrolidin]-1(2H)-yl]acetic acid,
[5-chloro-1'-(2-chloro-5-fluorobenzyl)-2,2',5'-trioxospiro[indole-3,3'-pyrrolidin]-1(2H)-yl]acetic acid,
[5-chloro-1'-(2,5-difluorobenzyl)-2,2',5'-trioxospiro[indole-3,3'-pyrrolidin]-1(2H)-yl]acetic acid,
[5-chloro-1'-(2,3-difluorobenzyl)-2,2',5'-trioxospiro[indole-3,3'-pyrrolidin]-1(2H)-yl]acetic acid,
[5-chloro-1'-(3,5-difluorobenzyl)-2,2',5'-trioxospiro[indole-3,3'-pyrrolidin]-1(2H)-yl]acetic acid,
[5-chloro-1'-(3,4-difluorobenzyl)-2,2',5'-trioxospiro[indole-3,3'-pyrrolidin]-1(2H)-yl]acetic acid,
[5-chloro-1'-[(1-methyl-1H-benzimidazol-2-yl)methyl]-2,2',5'-trioxospiro[indole-3,3'-pyrrolidin]-1(2H)-yl]acetic acid,
[5-chloro-1'-(3-fluoro-4-methoxybenzyl)-2,2',5'-trioxospiro[indole-3,3'-pyrrolidin]-1(2H)-yl]acetic acid,
[5-chloro-1'-(3-chloro-5-fluorobenzyl)-2,2',5'-trioxospiro[indole-3,3'-pyrrolidin]-1(2H)-yl]acetic acid,
[5-chloro-1'-[(5-methyl-3-phenylisoxazol-4-yl)methyl]-2,2',5'-trioxospiro[indole-3,3'-pyrrolidin]-1(2H)-yl]acetic acid,
[5-chloro-1'-[(3-methyl-5-phenylisoxazol-4-yl)methyl]-2,2',5'-trioxospiro[indole-3,3'-pyrrolidin]-1(2H)-yl]acetic acid,
[5-chloro-1'-{[2-(3-chlorophenyl)-1,3-thiazol-4-yl]methyl}-2,2',5'-trioxospiro[indole-3,3'-pyrrolidin]-1(2H)-yl]acetic acid,
[5-chloro-1'-(2-fluorobenzyl)-2,2',5'-trioxospiro[indole-3,3'-pyrrolidin]-1(2H)-yl]acetic acid,
[5'-chloro-1-(5-chloro-2-fluorobenzyl)-2,2',5-trioxospiro[imidazolidine-4,3'-indol]-1'(2'H)-yl]acetic acid,
[5'-chloro-1-[(5-methyl-3-phenylisoxazol-4-yl)methyl]-2,2',5-trioxospiro[imidazolidine-4,3'-indol]-1'(2'H)-yl]acetic acid,
(1-benzyl-5'-chloro-2,2',5-trioxospiro[imidazolidine-4,3'-indol]-1'(2'H)-yl)acetic acid,
[5'-chloro-1-(2-fluorobenzyl)-2,2',5-trioxospiro[imidazolidine-4,3'-indol]-1'(2'H)-yl]acetic acid,
(3R)-[5-chloro-1'-(2-fluorobenzyl)-2,2',5'-trioxospiro[indole-3,3'-pyrrolidin]-1(2H)-yl]acetic acid,
(3S)-[5-chloro-1'-(2-fluorobenzyl)-2,2',5'-trioxospiro[indole-3,3'-pyrrolidin]-1(2H)-yl]acetic acid, (3S)-[5-chloro-1'-(2-fluoro-5-chlorobenzyl)-2,2',5'-triox-ospiro[indole-3,3'-pyrrolidin]-1(2H)-yl]acetic acid,
(3R)-[5-chloro-1'-(2-fluoro-5-chlorobenzyl)-2,2',5'-triox-ospiro[indole-3,3'-pyrrolidin]-1(2H)-yl]acetic acid,
(1'-benzyl-5-chloro-2,5'-dioxospiro[indole-3,3'-pyrrolidin]-1(2H)-yl)acetic acid,
[5-chloro-1'-[(3-methyl-5-phenylisoxazol-4-yl)methyl]-2,5'-dioxospiro[indole-3,3'-pyrrolidin]-1(2H)-yl]acetic acid,
[5-chloro-1'-(2-fluorobenzyl)-2,5'-dioxospiro[indole-3,3'-pyrrolidin]-1(2H)-yl]acetic acid, and
[5-chloro-1'-(5-chloro-2-fluorobenzyl)-2,5-dioxospiro[indole-3,3'-pyrrolidin]-1(2H)-yl]acetic acid.

9. A compound according to Formula (I),

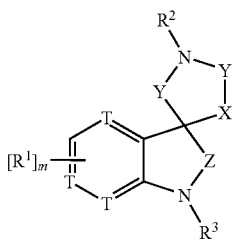

as well as its geometrical isomers, its optically active forms as enantiomers, diastereomers and its racemate forms, and tautomers, or a pharmaceutically acceptable salts thereof, wherein $R^1$ is selected from the group consisting of hydrogen, $C_1$-$C_6$-alkyl, $C_1$-$C_6$-alkoxy, halo-$C_1$-$C_6$-alkyl, halo-$C_1$-$C_6$-alkoxy, halogen, aryl and heteroaryl;
m is an integer selected from 0, 1, 2, 3 or 4;
$R^2$ is either $C_1$-$C_6$-alkyl or A;
$R^3$ is B;
$R^4$ is selected from the group consisting of $C_1$-$C_6$-alkyl, $C_2$-$C_6$-alkenyl, $C_2$-$C_6$-alkynyl, $C_3$-$C_8$-cycloalkyl, $C_3$-$C_8$-heterocycloalkyl, aryl, heteroaryl, sulfonylamine, amine, halo-$C_1$-$C_6$-alkyl, hydroxylamine and hydroxyl; wherein each $R^4$ may be substituted independently with one or more groups $R^6$;
$R^5$ is carboxy;
$R^6$ is selected from the group consisting of $C_1$-$C_6$-alkyl, alkoxy, alkoxycarbonyl, aryl, aryl $C_1$-$C_6$-alkyl, heteroaryl, heteroaryl $C_1$-$C_6$-alkyl, $C_3$-$C_8$-cycloalkyl, $C_3$-$C_8$-heterocycloalkyl, carboxyl, cyano, halogen, hydroxy, amino, amino carbonyl, nitro, sulfoxy, sulfonyl, sulfonamide and trihalo-$C_1$-$C_6$-alkyl;
$R^7$ is either hydrogen or $C_1$-$C_6$-alkyl;
A is selected from the group consisting of A1, A2, A3, A4, A5 and A6:

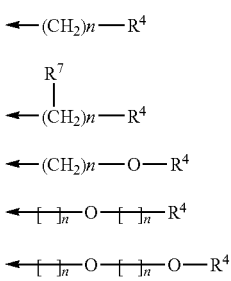

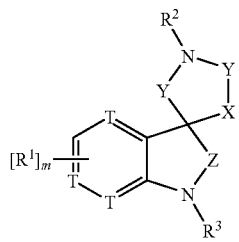

wherein each n is an integer independently selected from 0, 1, 2, 3, 4;
B is:

←(CH$_2$)$_n$-R$^5$;

wherein n is an integer selected from 1, 2, 3 or 4
T is CH;
each Y is independently either C(O), or CH2;
X is either CH$_2$ or NH; and
z is either C(O) or CHHR$^7$.

10. The compound according to claim 9, wherein $R^1$ is either halogen or halo-$C_1$-$C_6$-alkoxy.

11. The compound according to claim 10, wherein $R^1$ is halogen.

12. The compound according to claim 9, wherein $R^2$ is A1, and n is 1.

13. The compound according to claim 9, wherein $R^2$ is A5, and n is 2.

14. The compound according to claim 9, wherein $R^4$ is either aryl or heteroaryl.

15. The compound according to claim 9, wherein $R^3$ is B, and n is either 1 or 3.

16. A method for treating allergic disease, inflammatory dermatoses, rheumatoid arthritis, inflammatory bowel disease and multiple sclerosis comprising administering to a subject a compound, wherein said compound is a modulator of CRTH2 activity, according to Formula (I):

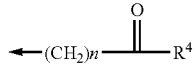

$R^1$ is selected from the group consisting of hydrogen, $C_1$-$C_6$-alkyl, $C_1$-$C_6$-alkoxy, halo-$C_1$-$C_6$-alkyl, halo-$C_1$-$C_6$-alkoxy, halogen, aryl and heteroaryl;
m is an integer selected from 0, 1, 2, 3 or 4;
$R^2$ is either $C_1$-$C_6$-alkyl or A;
$R^3$ is either $C_1$-$C_6$-alkyl or B;
$R^4$ is selected from the group consisting of $C_1$-$C_6$-alkyl, $C_2$-$C_6$-alkenyl, $C_2$-$C_6$-alkynyl, $C_3$-$C_8$-cycloalkyl, $C_3$-$C_8$-heterocycloalkyl, aryl, heteroaryl, sulfonylamine, amine, halo-$C_1$-$C_6$-alkyl, hydroxylamine and hydroxyl; wherein each $R^4$ may be substituted independently with one or more groups $R^6$;
$R^5$ is carboxy;
$R^6$ is selected from the group consisting of $C_1$-$C_6$-alkyl, alkoxy, alkoxycarbonyl, aryl, aryl $C_1$-$C_6$-alkyl, heteroaryl, heteroaryl $C_1$-$C_6$-alkyl, $C_3$-$C_8$-cycloalkyl, $C_3$-$C_8$-heterocycloalkyl, carboxyl, cyano, halogen, hydroxy, amino, amino carbonyl, nitro, sulfoxy, sulfonyl, sulfonamide and trihalo-$C_1$-$C_6$-alkyl;
$R^7$ is either hydrogen or $C_1$-$C_6$-alkyl;

A is selected from the group consisting of A1, A2, A3, A4, A5 and A6:

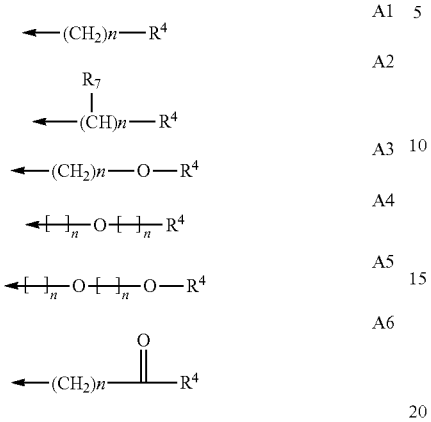

wherein each n is an integer independently selected from 0, 1, 2, 3 or 4;

B is:

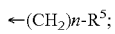

wherein n is an integer selected from 1, 2, 3 or 4

T is CH;

each Y is independently either C(O), or CH2;

X is either $CH_2$ or NH; and z is either C(O) or $CHR^7$;

as well as geometrical isomers, enantiomers, diastereomers, racemate forms and pharmaceutically acceptable salts of said compounds for the preparation of a medicament.

17. The method according to claim 16, wherein said allergic disease is selected from the group consisting of allergic asthma, allergic rhinitis, allergic conjunctivitis, systemic anaphylaxis or hypersensitivity responses.

18. The method according to claim 16, wherein said inflammatory dermatosis is selected from the group consisting of atopic dermatitis, contact hypersensitivity, allergic contact dermatitis, chronic urticaria/chronic, idiopathic/autoimmune urticaria, drug-induced exanthems, photodermatosis or polymorphous light eruption and myositis.

19. A pharmaceutical composition containing at least one compound according to claim 1 or 9 and a pharmaceutically acceptable carrier, diluent or excipient thereof.

20. Process for the manufacture of the compound of Formula (I') wherein intermediate II:

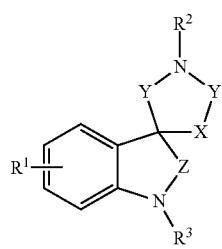

where:

$R^3$ is $(CH_2)n\text{-}CO_2R$ wherein R is either $C_1$-$C_6$-alkyl or benzyl and n is an integer selected from 1, 2, 3 or 4;

$R^1$ is selected from the group consisting of hydrogen, $C_1$-$C_6$-alkyl, $C_1$-$C_6$-alkoxy, halo-$C_1$-$C_6$-alkyl, halo-$C_1$-$C_6$-alkoxy, halogen, aryl and heteroaryl;

$R^2$ is either $C_3$-$C_6$-alkyl or A; wherein

A is selected from the group consisting of A1, A2, A3, A4, A5 and A6:

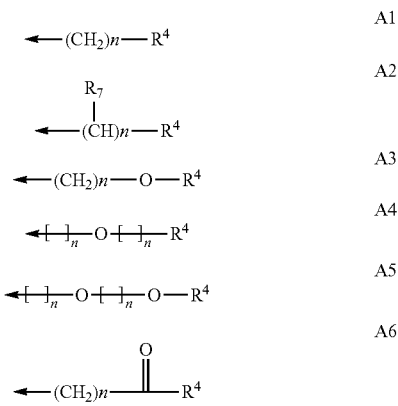

with each n being an integer independently selected from 1, 2, 3 or 4; wherein $R^4$ is selected from the group consisting of $C_2$-$C_6$ alkyl, $C_2$-$C_6$ alkenyl, $C_3$-$C_8$-cycloalkyl, $C_3$-$C_8$-heterocycloalkyl, aryl and heteroaryl; each $R^4$ may optionally be substituted independently with one or more groups $R^6$; each $R^6$ is independently selected from the group consisting of $C_1$-$C_6$-alkyl, alkoxy, alkoxycarbonyl, aryl, aryl $C_1$-$C_6$-alkyl, heteroaryl, substituted or unsubstituted heteroaryl $C_1$-$C_6$-alkyl, $C_3$-$C_8$-cycloalkyl, $C_3$-$C_8$-heterocycloalkyl, carboxyl, cyano, halogen, hydroxy, amino, aminocarbonyl, acylamino, nitro, sulfoxy, sulfonyl, sulfonylamine, aminosulfonyl and trihalo-$C_1$-$C_6$-alkyl;

$R^7$ is either hydrogen or $C_1$-$C_6$-alkyl;

X is either $CH_2$ or NH;

each Y is independently either C(O) or $CH_2$; and z is either C(O) or $CHR^7$; is hydrolized under conditions such that Formula I' is formed:

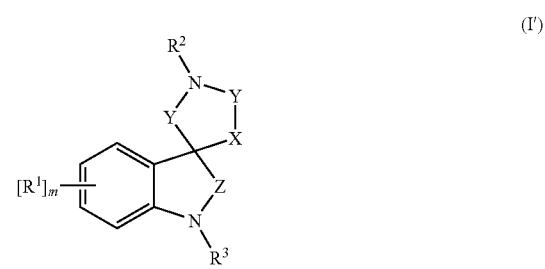

where:

$R^3$ is $(CH_2)n\text{-}CO_2H$ wherein n is an integer selected from 1,2,3 of 4;

$R^1$ is selected from the group consisting of hydrogen, $C_1$-$C_6$-alkyl, $C_1$-$C_6$-alkoxy, halo-$C_1$-$C_6$-alkyl, halo-$C_1$-$C_6$-alkoxy, halogen, aryl and heteroaryl;

m is an integer selected from 0, 1, 2, 3 or 4;

$R^2$ is either $C_3$-$C_6$-alkyl or A; wherein

A is selected from the group consisting of A1, A2, A3, A4, A5 and A6:

| | A1 |
|---|---|
| ←—(CH₂)n—R⁴ | |

| | A2 |
|---|---|
| R₇<br>\|<br>←—(CH)n—R⁴ | |

| | A3 |
|---|---|
| ←—(CH₂)n—O—R⁴ | |

| | A4 |
|---|---|
| ←—[ ]n—O—[ ]n—R⁴ | |

| | A5 |
|---|---|
| ←—[ ]n—O—[ ]n—O—R⁴ | |

| | A6 |
|---|---|
| ←—(CH₂)n—C(=O)—R⁴ | | with each n being an integer independently selected from 1, 2, 3 or 4; wherein $R^4$ is selected from the group consisting of $C_2$-$C_6$ alkyl, $C_2$-$C_6$ alkenyl, $C_3$-$C_8$-cycloalkyl, $C_3$-$C_8$-heterocycloalkyl, aryl and heteroaryl; each $R^4$ may optionally be substituted independently with one or more groups $R^6$; each $R^6$ is independently selected from the group consisting of $C_1$-$C_6$-alkyl, alkoxy, alkoxycarbonyl, aryl, aryl $C_1$-$C_6$-alkyl, heteroaryl, substituted or unsubstituted heteroaryl $C_1$-$C_6$-alkyl, $C_3$-$C_8$-cycloalkyl, $C_3$-$C_8$-heterocycloalkyl, carboxyl, cyano, halogen, hydroxy, amino, aminocarbonyl, acylamino, nitro, sulfoxy, sulfonyl, sulfonylamine, aminosulfonyl and trihalo-$C_1$-$C_6$-alkyl;

$R^7$ is either hydrogen or $C_1$-$C_6$-alkyl;

X is either $CH_2$ or NH;

each Y is independently either C(O) or $CH_2$; and z is either C(O) or $CHR^7$.

21. The process according to claim 20, wherein said intermediate II:

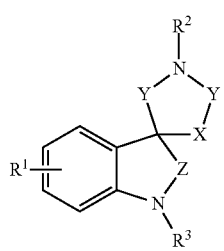

II is formed by means of an alkylation of intermediate III:

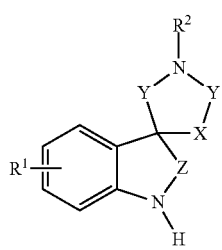

III where:

$R^1$ is selected from the group consisting of hydrogen, $C_1$-$C_6$-alkyl, $C_1$-$C_6$-alkoxy, halo-$C_1$-$C_6$-alkyl, halo-$C_1$-$C_6$-alkoxy, halogen, aryl and heteroaryl;

$R^2$ is either $C_3$-$C_6$-alkyl or A; wherein:

A is selected from the group consisting of A1, A2, A3, A4, A5 and A6:

| | A1 |
|---|---|
| ←—(CH₂)n—R⁴ | |

| | A2 |
|---|---|
| R₇<br>\|<br>←—(CH)n—R⁴ | |

| | A3 |
|---|---|
| ←—(CH₂)n—O—R⁴ | |

| | A4 |
|---|---|
| ←—[ ]n—O—[ ]n—R⁴ | |

| | A5 |
|---|---|
| ←—[ ]n—O—[ ]n—O—R⁴ | |

| | A6 |
|---|---|
| ←—(CH₂)n—C(=O)—R⁴ | | with each n being an integer independently selected from 1, 2, 3 or 4; wherein $R^4$ is selected from the group consisting of $C_2$-$C_6$ alkyl, $C_2$-$C_6$ alkenyl, $C_3$-$C_8$-cycloalkyl, $C_3$-$C_8$-heterocycloalkyl, aryl and heteroaryl;

each $R^4$ may optionally be substituted independently with one or more groups $R^6$;

each $R^6$ is independently selected from the group consisting of $C_1$-$C_6$-alkyl, alkoxy, alkoxycarbonyl, aryl, aryl $C_1$-$C_6$-alkyl, heteroaryl, substituted or unsubstituted heteroaryl $C_1$-$C_6$-alkyl, $C_3$-$C_8$-cycloalkyl, $C_3$-$C_8$-heterocycloalkyl, carboxyl, cyano, halogen, hydroxy, amino, aminocarbonyl, acylamino, nitro, sulfoxy, sulfonyl, sulfonylamine, aminosulfonyl and trihalo-$C_1$-$C_6$-alkyl;

$R^7$ is either hydrogen or $C_1$-$C_6$-alkyl;

X is either $CH_2$ or NH;

each Y is independently either C(O) or $CH_2$; and z is either C(O) or $CHR^7$.

22. The process according to claim 20 wherein said intermediate II:

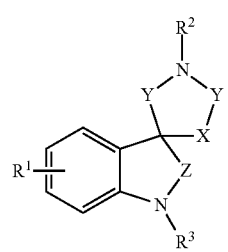

II is formed by means of an alkylation of intermediate IV:

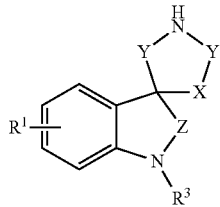

IV where:
R¹ is selected from the group consisting of hydrogen, $C_1$-$C_6$-alkyl, $C_1$-$C_6$-alkoxy, halo-$C_1$-$C_6$-alkyl, halo-$C_1$-$C_6$-alkoxy, halogen, aryl and heteroaryl;

R³ is B, wherein
B is:

←$(CH_2)n$-$R^5$ with n being an integer independently selected from 1, 2, 3 or 4; wherein
$R^5$ is carboxy;
X is either $CH_2$ or NH;
each Y is independently either C(O) or $CH_2$; and
z is either C(O) or $CHR^7$.

* * * * *

UNITED STATES PATENT AND TRADEMARK OFFICE
CERTIFICATE OF CORRECTION

PATENT NO. : 8,236,963 B2
APPLICATION NO. : 11/919471
DATED : August 7, 2012
INVENTOR(S) : Schwarz et al.

It is certified that error appears in the above-identified patent and that said Letters Patent is hereby corrected as shown below:

Column 148, Line 35 (Claim 8), which reads "[1'43-fluorobenzyl)-2,2',5'-trioxo-5-(trifluoromethoxy)spiro[indole-3,3'-pyrrolidin]-1(2H)-yl]acetic acid,"
-should read "[1'-(3-fluorobenzyl)-2,2',5'-trioxo-5-(trifluoromethoxy)spiro[indole-3,3'-pyrrolidin]-1(2H)-yl]acetic acid,"

Signed and Sealed this
Ninth Day of October, 2012

David J. Kappos
*Director of the United States Patent and Trademark Office*